US011589882B2

(12) United States Patent
Gamba et al.

(10) Patent No.: US 11,589,882 B2
(45) Date of Patent: *Feb. 28, 2023

(54) DEVICES AND METHODS FOR REMOVING MATERIAL FROM A PATIENT

(71) Applicant: Xtract Medical, Inc., Louisville, CO (US)

(72) Inventors: Jorge Gamba, Jacksonville, FL (US); Eric Sauvageau, Jacksonville, FL (US); Michael Schaller, Louisville, CO (US)

(73) Assignee: XTRACT MEDICAL, INC., Louisville, CO (US)

( * ) Notice: Subject to any disclaimer, the term of this patent is extended or adjusted under 35 U.S.C. 154(b) by 578 days.

This patent is subject to a terminal disclaimer.

(21) Appl. No.: 16/790,268

(22) Filed: Feb. 13, 2020

(65) Prior Publication Data

US 2020/0253624 A1    Aug. 13, 2020

Related U.S. Application Data

(63) Continuation of application No. 16/443,820, filed on Jun. 17, 2019, now Pat. No. 10,624,659, which is a continuation of application No. PCT/US2019/021943, filed on Mar. 12, 2019.

(60) Provisional application No. 62/793,498, filed on Jan. 17, 2019, provisional application No. 62/641,948, filed on Mar. 12, 2018.

(51) Int. Cl.
*A61B 17/221* (2006.01)

(52) U.S. Cl.
CPC .... *A61B 17/221* (2013.01); *A61B 2017/2215* (2013.01)

(58) Field of Classification Search
CPC ............ A61B 17/221; A61B 17/22031; A61B 17/32056; A61B 2017/2215; A61B 2017/00358; A61B 2017/22034
See application file for complete search history.

(56) References Cited

U.S. PATENT DOCUMENTS

| | | | |
|---|---|---|---|
| 5,681,324 A | 10/1997 | Kammerer et al. | |
| 2006/0047286 A1 | 3/2006 | West | |
| 2006/0195118 A1* | 8/2006 | Richardson | .......... A61B 17/221 606/113 |
| 2008/0125709 A1 | 5/2008 | Chang et al. | |
| 2011/0125181 A1 | 5/2011 | Brady et al. | |
| 2013/0144326 A1 | 6/2013 | Brady et al. | |
| 2014/0025083 A1 | 1/2014 | Richardson | |
| 2017/0065299 A1 | 3/2017 | Gillespie et al. | |

(Continued)

FOREIGN PATENT DOCUMENTS

WO    2020/099386 A1    5/2020

OTHER PUBLICATIONS

International Search Report and Written Opinion, PCT/US2019/021943, dated Aug. 26, 2019.

(Continued)

*Primary Examiner* — Katherine M Rodjom
(74) *Attorney, Agent, or Firm* — Polsinelli PC

(57) ABSTRACT

A containing element is used to capture material in a blood vessel for removal. The containing element is positioned within a constraining catheter while it is advanced through the blood vessel. A filament is coupled to the containing element which assists in opening and/or closing the containing element.

20 Claims, 30 Drawing Sheets

(56) References Cited

U.S. PATENT DOCUMENTS

2017/0086861 A1  3/2017  Mansfield et al.
2018/0235644 A1  8/2018  Jaffe et al.
2019/0298396 A1  10/2019 Gamba et al.

OTHER PUBLICATIONS

International Search Report and Written Opinion, PCT/US2021/034429, dated Aug. 31, 2021.

* cited by examiner

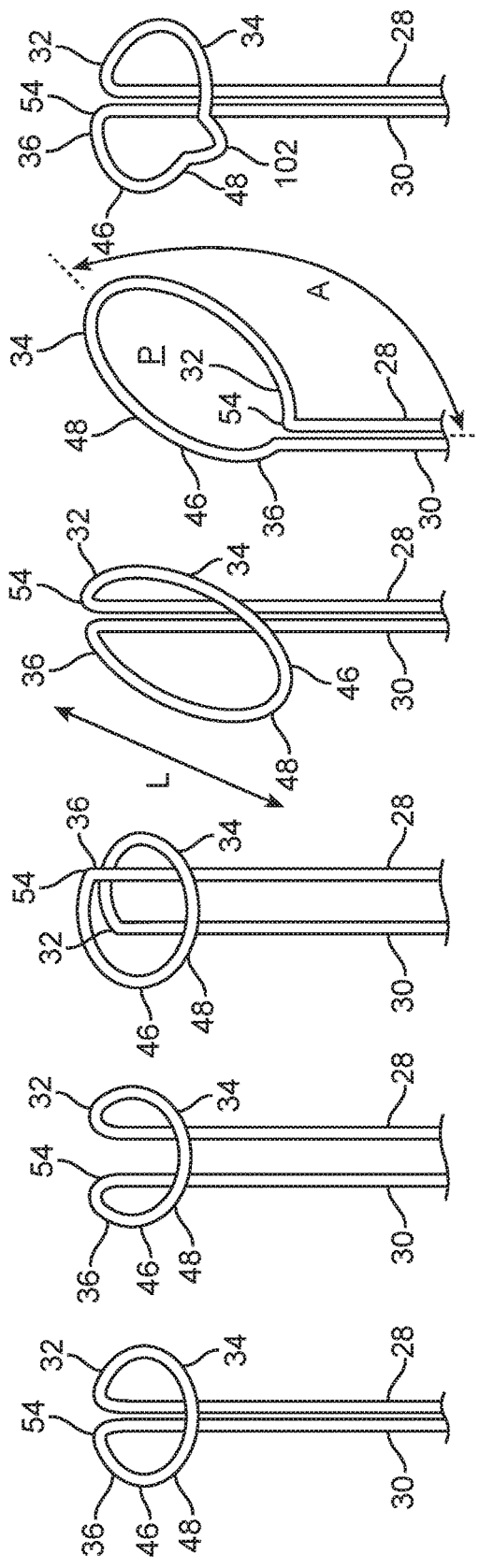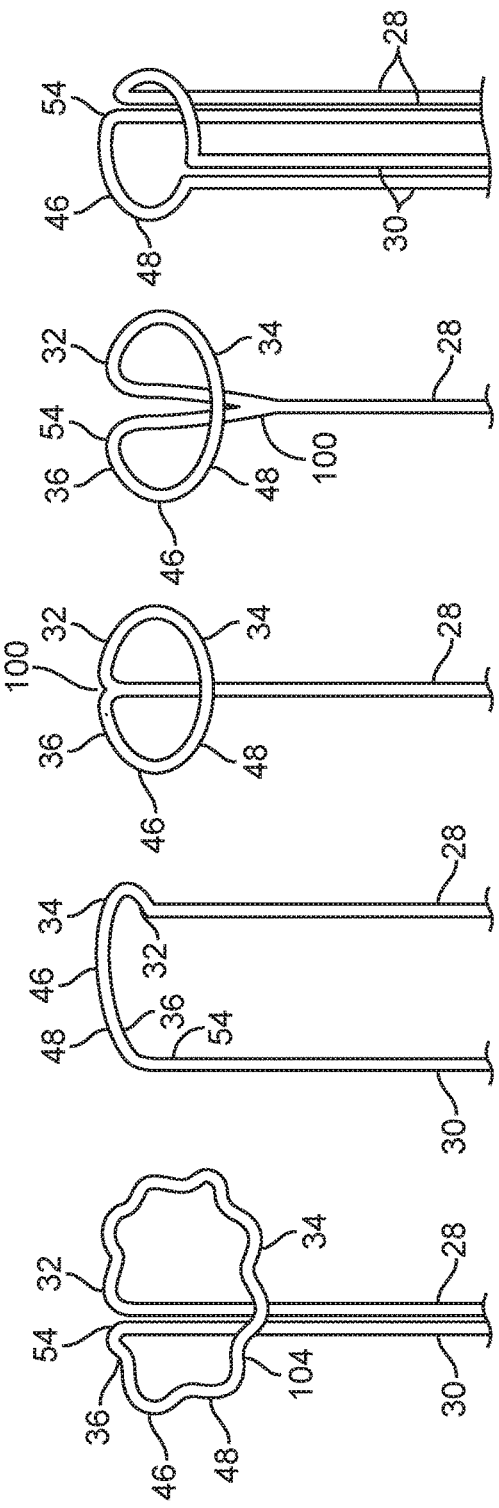

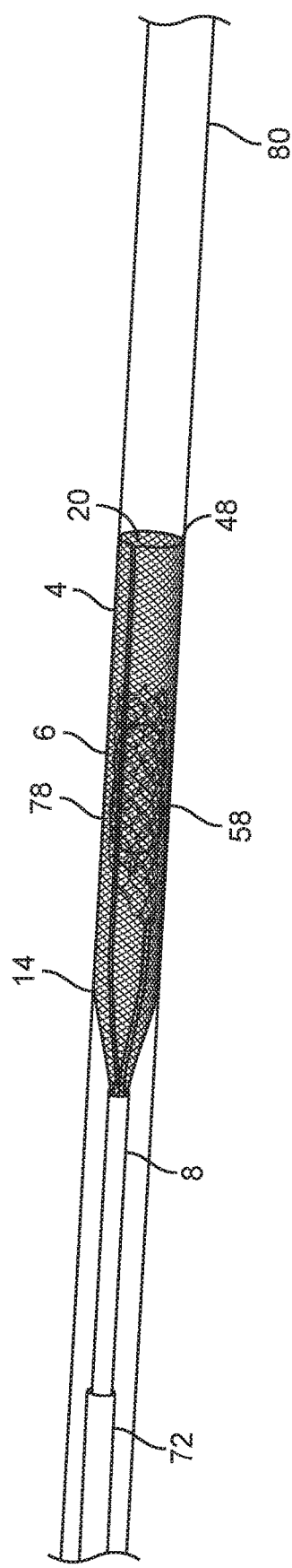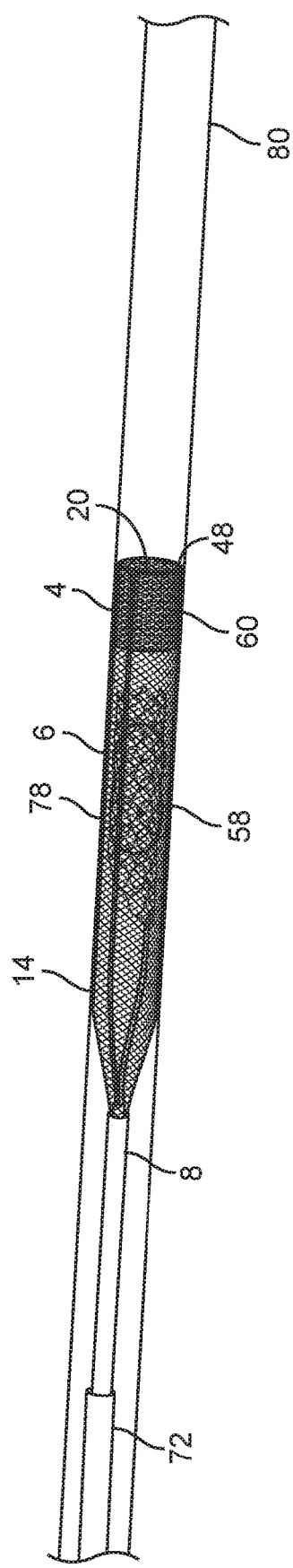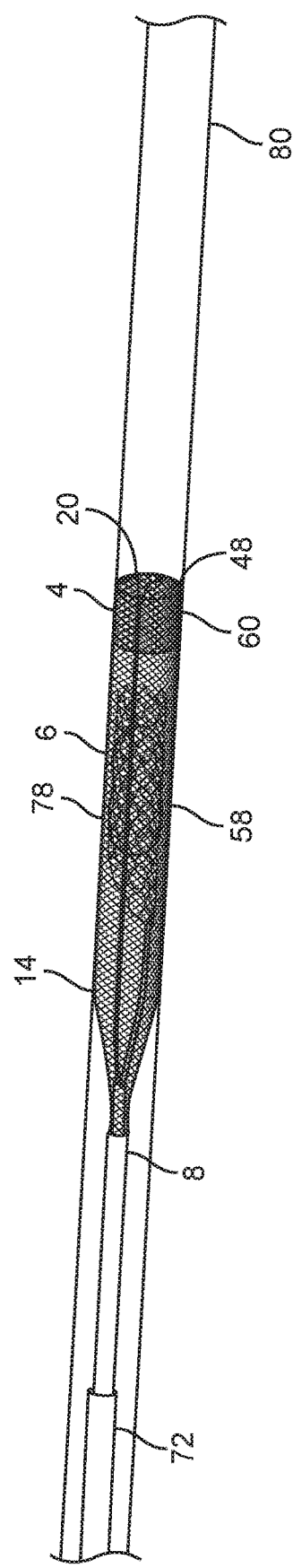

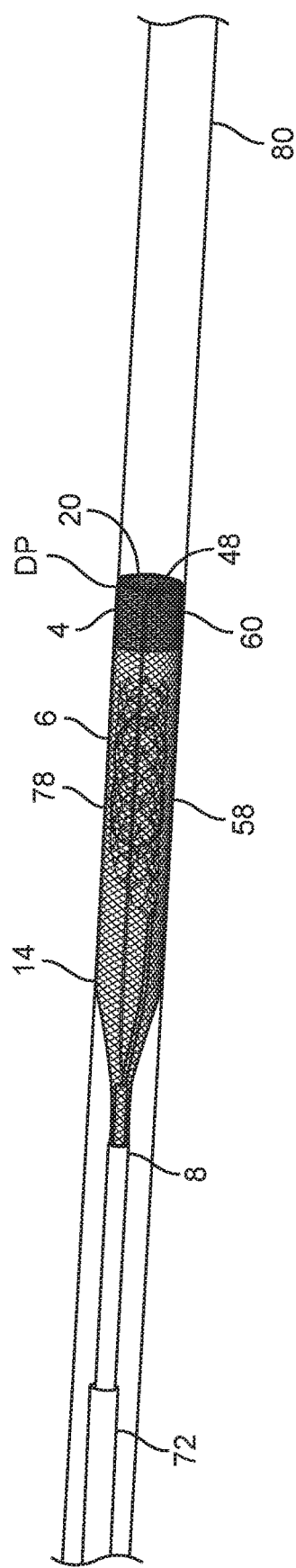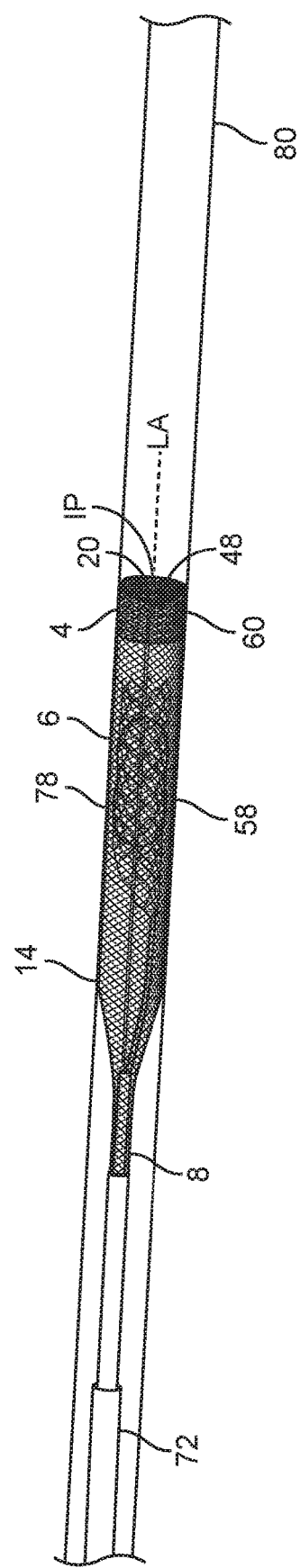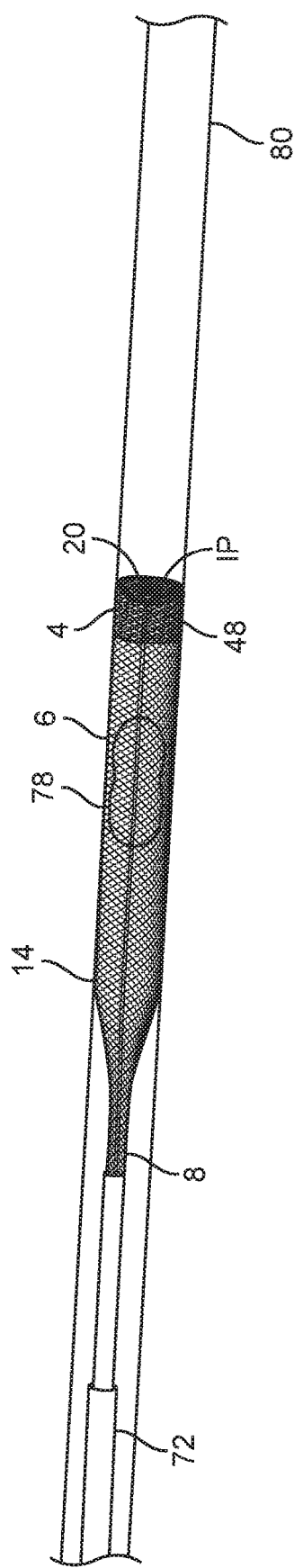

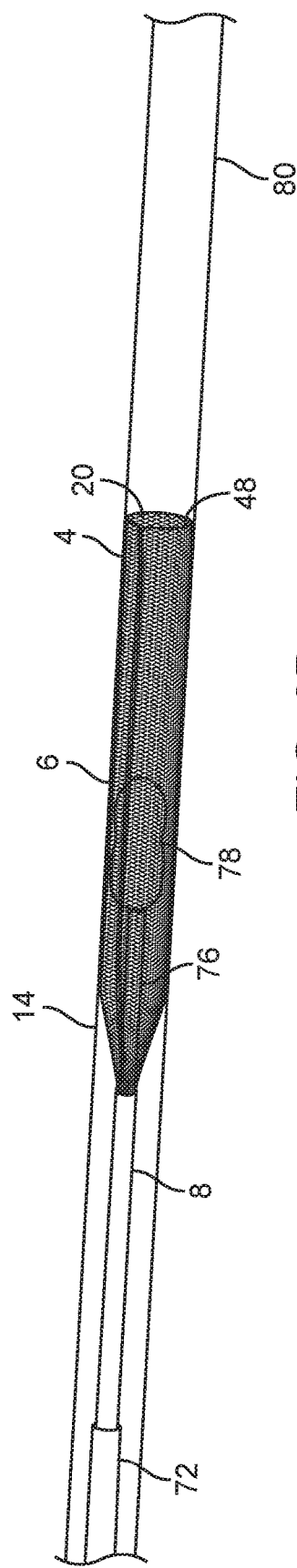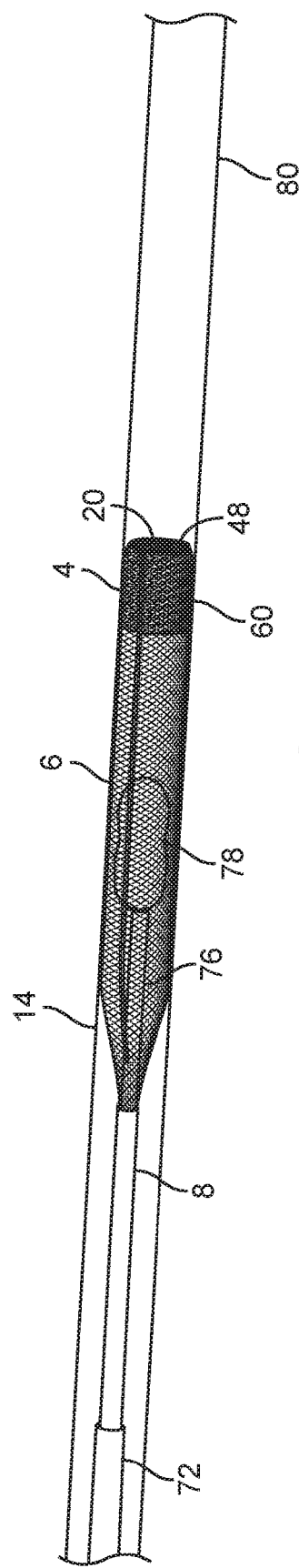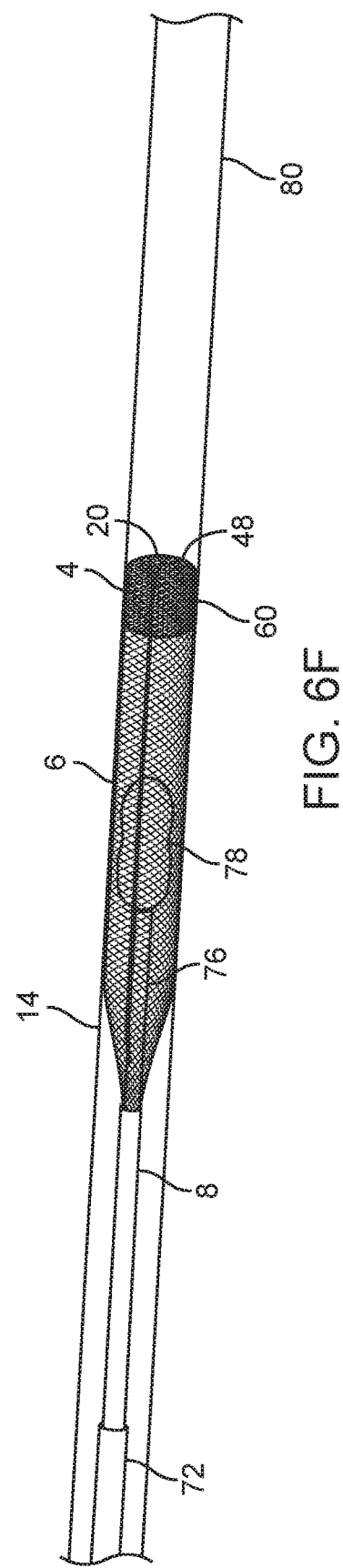

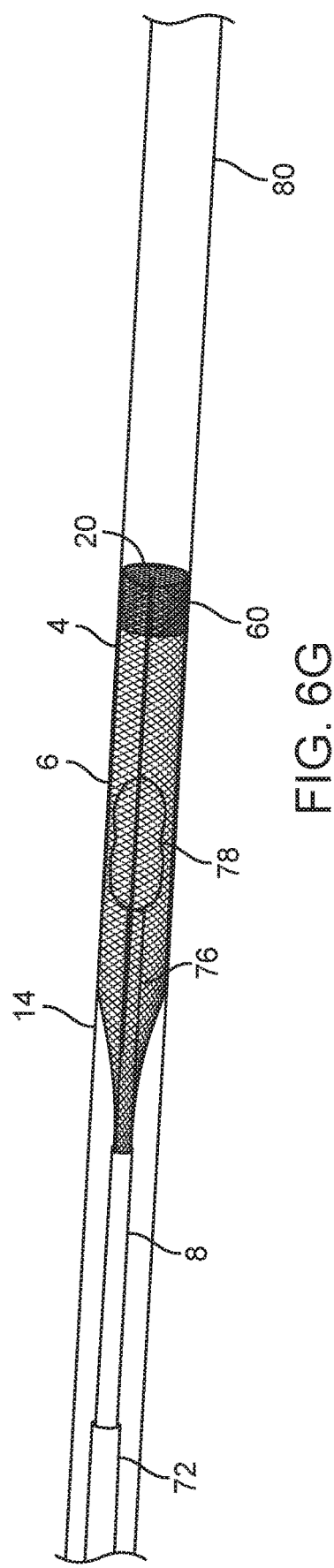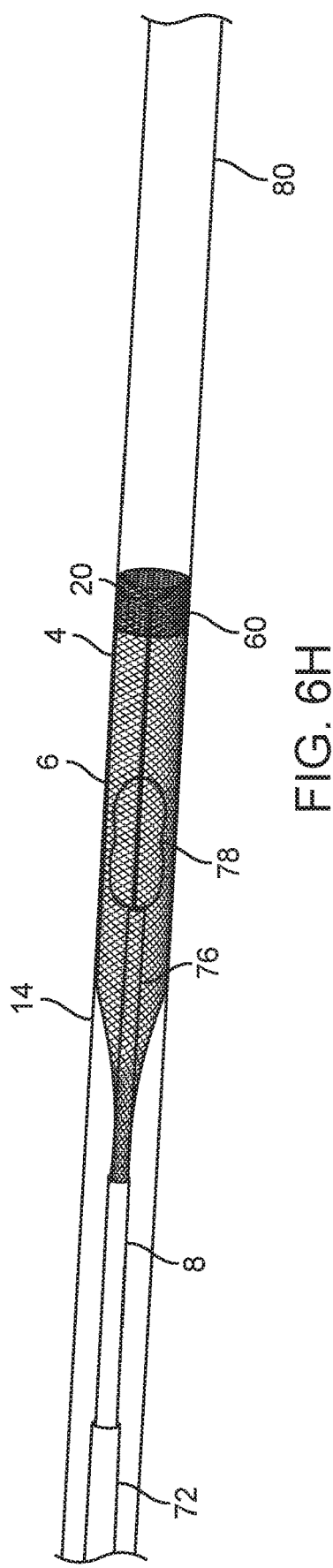

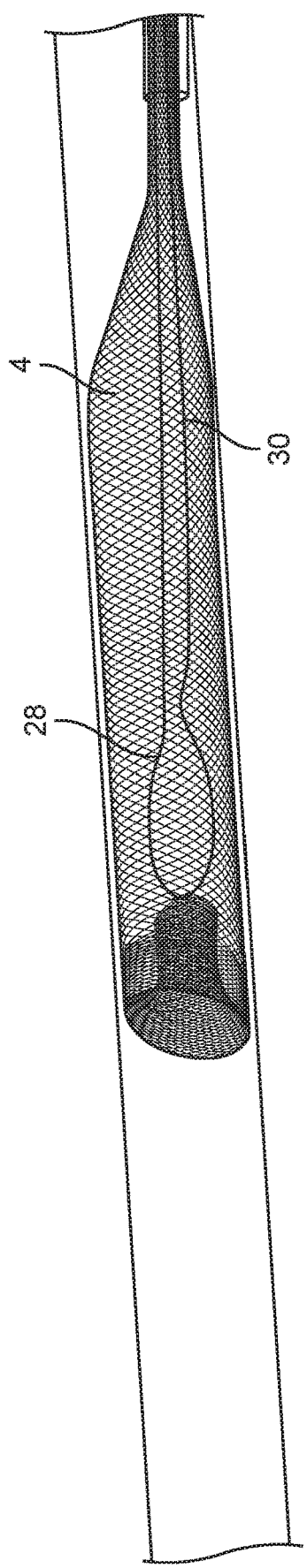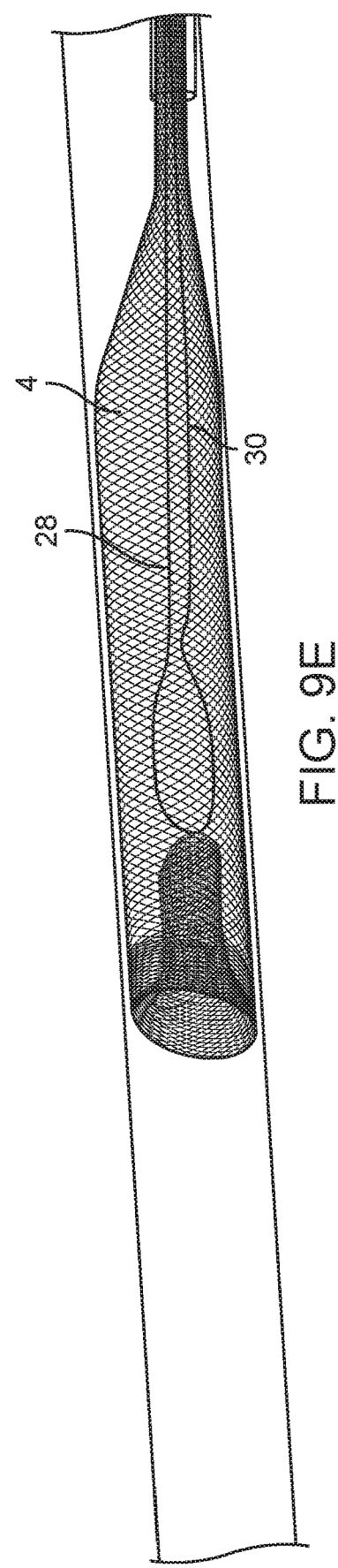
FIG. 9D
FIG. 9E

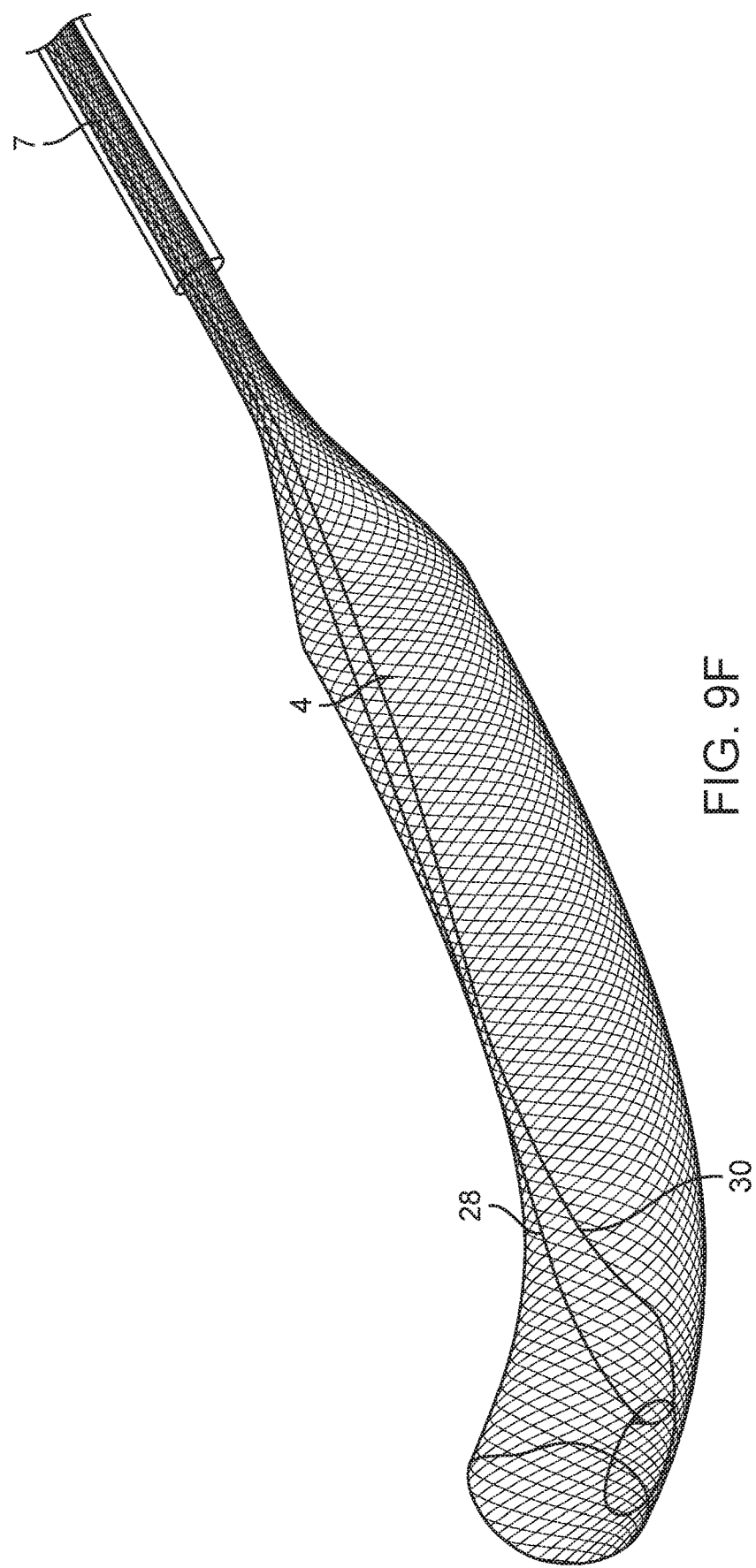

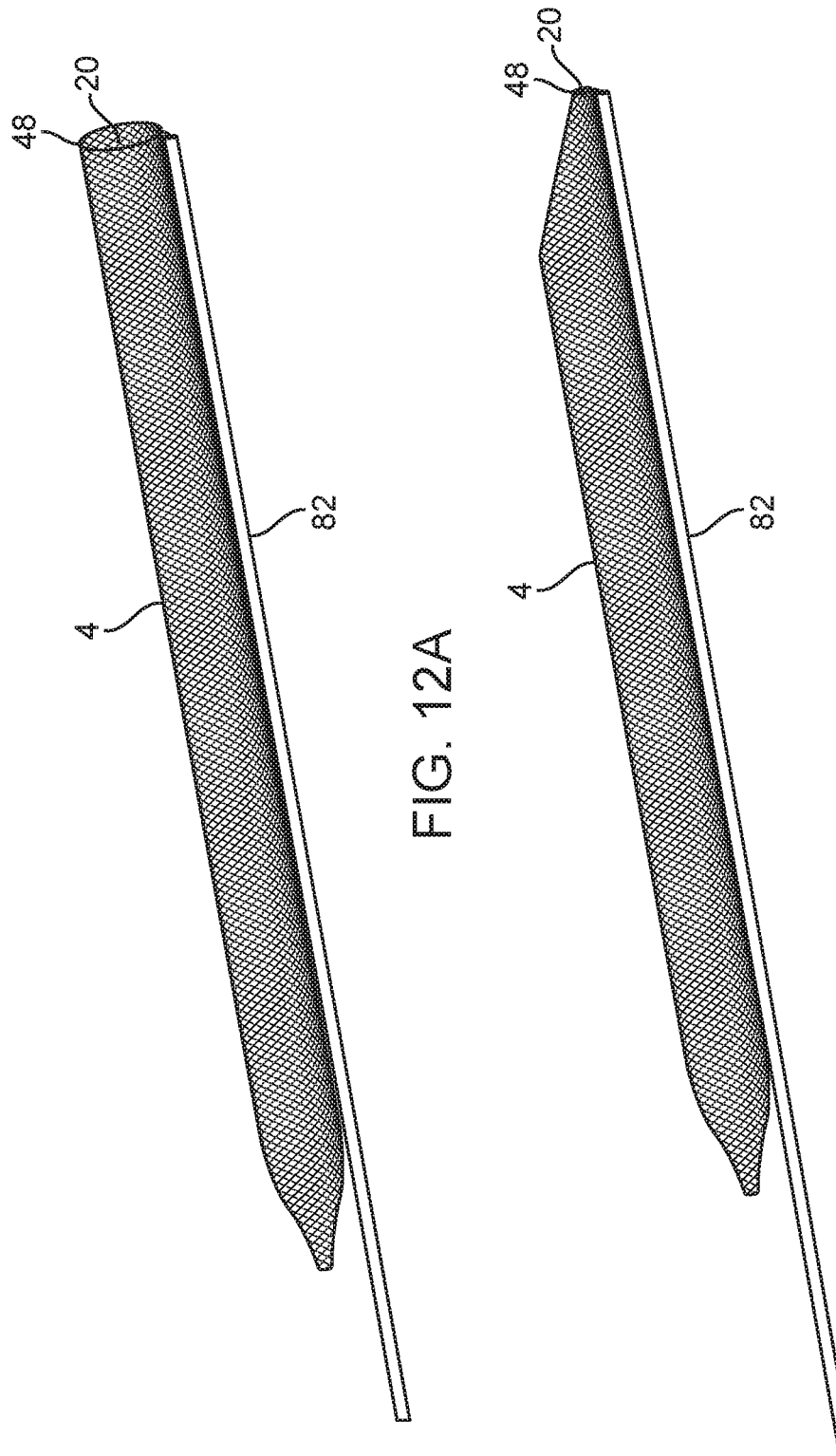

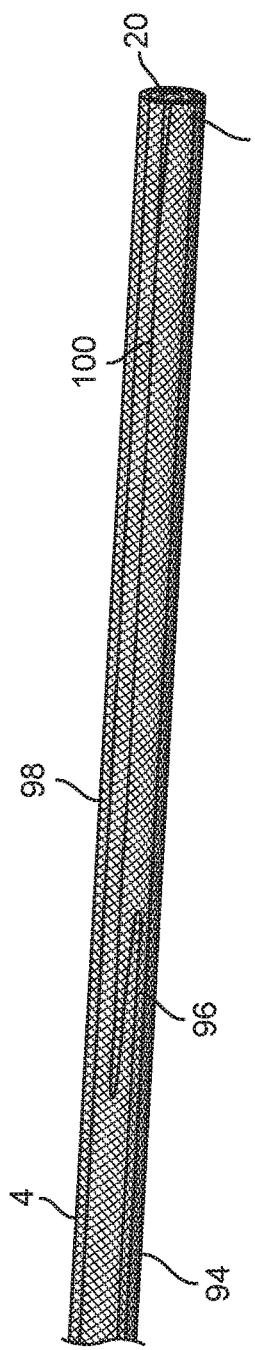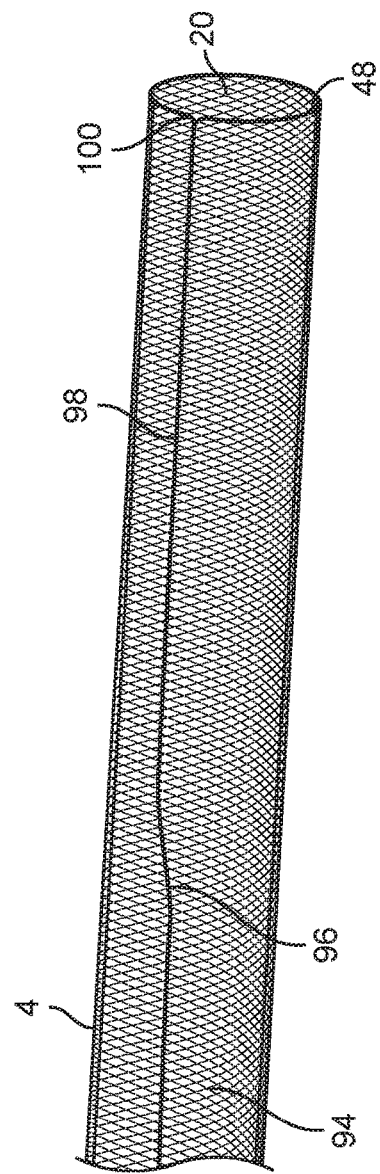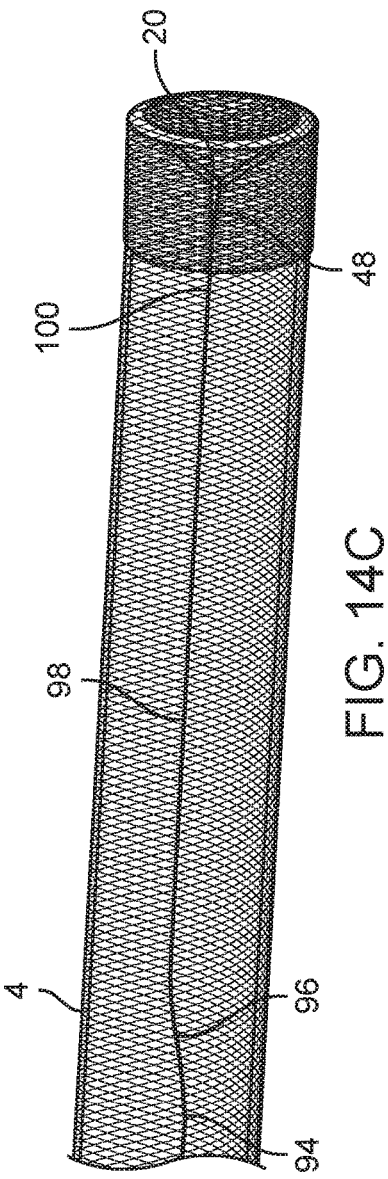

DEVICES AND METHODS FOR REMOVING MATERIAL FROM A PATIENT

CROSS-REFERENCE TO RELATED APPLICATIONS

This application is a continuation of U.S. patent application Ser. No. 16/443,820, filed Jun. 17, 2019, entitled "Devices and Methods for Removing Material From a Patient", which is a continuation of PCT/US2019/021943, filed Mar. 12, 2019, which claims the priority benefit of U.S. Provisional Patent Application No. 62/641,948, filed Mar. 12, 2018, entitled "Treatment Device and Method" and of U.S. Provisional Patent Application No. 62/793,498, filed Jan. 17, 2019, entitled "Treatment Device and Method", which are all herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of surgery, and more specifically to the field of interventional radiology. Described herein are devices and methods for removing material from a patient.

BACKGROUND

Minimally invasive endovascular techniques have come to the forefront in the safe and expeditious use of embolectomy devices for thromboembolic clot extraction. Currently employed devices generally extract the clot using a combination of balloons, graspers, aspiration, and wire retrievers. These devices attempt to remove the clot in vivo by attaching to it and then pulling it through the vascular lumen and out of the body. With these devices the thrombus is typically not fully contained and if fragments of the clot break away, they may become new emboli in the blood stream. That is to say that existing devices typically maintain partial or full exposure of the thrombus within the vascular lumen and when clot extraction is attempted the "bare thrombus" can pose a threat of fragmentation or partial clot dislodgement which can predispose a patient to inadvertent distal embolization, non-target territory embolization or incomplete thrombus extraction.

Additionally, in order to limit the blood flow in the clotted vessel during clot removal, many procedures utilize a variety of flow arrest techniques such as balloon-assisted proximal vessel occlusion to minimize antegrade flow in an effort to exclude distal clot fragmentation during clot extraction. Mechanical or assisted suction techniques are oftentimes utilized simultaneously via the balloon flow arrest catheter to capture any potential embolic debris during clot extraction. However, complete flow arrest in the brain arteries is often difficult due to extensive intracranial collaterals (e.g. Circle of Willis), limiting the efficacy and utility of proximal flow arrest and suction in the carotid circulation. Even limited blood flow can create a significant risk of clot fragmentation and distal migration of clot during extraction.

Completely encasing the clot captured within the stent-retriever by isolating the thromboembolism and excluding it from the vascular flow channel would eliminate or markedly reduce the risk of embolization.

SUMMARY

The present invention is directed to devices and methods for removing material from a blood vessel. In a specific application, the devices and methods are used to capture and remove material from the cerebral vasculature. The device includes a capture element which is collapsed and loaded into a delivery catheter which is advanced to a vascular location. The capture element is then deployed in a position to receive and contain material for removal. A clot retrieving element (such as a stent retriever) may be used to engage the material to be removed and assist in moving the material into the capture element.

The capture element is contained within a chamber (which may be a lumen) in the delivery catheter when advanced through the vasculature. The capture element has a distal opening at a distal end and a sidewall extending proximally from the distal opening. The distal opening is moved to an open position to receive the material. The distal opening defines a perimeter which is used to define aspects of the invention described below.

A first filament is coupled to the capture element to manipulate the capture element. When the capture element is positioned at or near the location where the material is to be removed, the capture element is released from the chamber by moving the capture element to a position outside the chamber. The capture element may be moved out of the chamber by manipulating the delivery catheter and/or the capture element.

When the capture element is released, the first filament may support the open position of the distal opening. For example, the first filament may have a predetermined shape which supports the open position. The predetermined shape may extend around at least 120 degrees, at least 150 degrees or at least 260 degrees, around the distal opening in the open position when viewed along a longitudinal axis defined by the capture element. The predetermined shape of the first filament may form a first concave portion (facing the longitudinal axis) which supports and moves the distal opening to the open position when the capture element is released. The first concave portion may generally lie in a plane which forms an angle with the first arm of 45-135 degrees in an unbiased position. When the capture element is closed, the plane forms an angle with the first arm of 135-180 degrees.

Stated another way, the concave portion has a shape larger than an unbiased shape of the distal opening so that the concave portion biases the distal opening toward the open position. The concave portion may be restrained by the open position of capture element so that the concave portion biases the distal opening toward the open position.

When the capture element is released and the distal opening is open, the material is then engaged (with a clot engaging element such as a stent retriever) and passed through the distal opening and into the capture element. The first filament may be coupled to the delivery catheter so that the first filament moves proximally relative to the capture element when the capture element moves to the released position and when the capture element is closed. Manipulation of the first filament with the delivery catheter provides advantages over systems that require the tension element to extend out of the patient (such as lower tension force required at the proximal end resulting in lower forces exerted on blood vessels through which the tension element extends). Of course, the first filament may also extend out of the patient and be manipulated independent of the delivery catheter without departing from numerous aspects of the present invention.

Once the material is contained within the capture element, the capture element is moved to a closed position in which the distal opening is reduced in size to prevent the material from escaping through the distal opening as the capture element is removed and/or moved into the delivery catheter or another catheter or sheath for removal from the patient. The distal opening may be closed by tensioning the first filament. The first filament may have a first arm and a second arm which are both tensioned. The first and second arms may extend from the first and second ends of the concave portion, respectively. Further aspects of the present invention will now be described with reference to the various positions of the first filament and the capture element and the basic method steps described above.

When the capture element and first filament are advanced through the blood vessel, the first filament may have a first leading portion which extends from the distal end of the capture element within the delivery catheter. The first leading portion may have a length (which may form a first loop) which extends from the distal end of the capture element at least 30%, or at least 50%, of an effective diameter of the perimeter of the distal opening in the open position when moving to the open position. The first leading portion may be free of attachments to the capture element and may extend distally at least 1.5 mm from the distal end of the capture element as the capture element is released (and while the distal opening is moving toward the open position). The term "loop" as it pertains to the leading portion does not require a closed loop and merely requires a segment having both ends extending outwardly from the distal end of the delivery element. As used herein, the effective diameter is the equivalent diameter of a circle having the same area as the distal opening (the area circumscribed by the perimeter) or other reference area or cross-section.

The first filament may be positioned at a relatively distal location when advanced through the vasculature by the delivery catheter. The first filament defines a working length which is the length of the first filament positioned within 10 cm of the distal end of the capture element. The working length of the first filament includes the first arm, the second arm and the concave portion but may include just one arm in some embodiments and may omit the concave portion in without departing from the scope of the invention. The working length of the first filament changes by less than 70% of the effective diameter of the distal opening in the open position when the capture element moves from the collapsed position to the released position.

The first filament (and optionally the first leading portion) may also engage an inner surface of the sidewall of the capture element when the filament moves to the released position. The first filament may also apply (exert) an outward force to the inner surface of the sidewall over a longitudinal length of at least 2 cm and may contact the inner surface through an angle of at least 180 degrees when viewed along the longitudinal axis.

When the capture element is closed by tensioning the first and second arms, the concave portion is deformed to reduce the size of the distal opening. The concave portion may be elastically deformed when and may be formed of a superelastic material deformed into a superelastic state. The effective diameter of the distal opening may reduce in size by at least 80% when moving to the closed position (and may be no more than 1 mm in the closed position).

Tensioning the first filament (specifically the first and second arms) may also invert a portion of the sidewall at the distal end. Inverting of the sidewall also moves the distal opening proximally to a position surrounded by the sidewall. The sidewall may resist inverting so that a radially inward force is exerted on the inverted portion which is transmitted through the sidewall to bias the distal opening toward the closed position.

The sidewall of the capture element may also include an expandable portion. The expandable portion may be at least 10 mm long and within 10 mm from the distal end of the capture element. The expandable portion may exert a radially outward force on the vessel wall when tensioning the first filament to close the capture element. The expandable portion may be naturally biased outward due to the physical properties and shape of the sidewall. Alternatively, the first filament may move and/or assist the sidewall and distal opening to the open position.

The expandable portion may be expanded by the first filament beyond an unbiased shape so that an effective diameter of the expandable portion increases by at least 10%. Stated another way, when the capture element is moved to the closed position the first filament is tensioned to exert an outward force on the expandable portion and may increase a radially outward force on the vessel wall by at least 10%. The sidewall of the capture element may also have a distal portion which reduces in length when the capture element is closed. The distal portion may extend 10 mm from the distal end and reduces in length longitudinally by at least 20% when the capture element moves to the closed position. The distal portion may also expand in accordance with the expandable portion described below.

In some embodiments, the first concave portion may form a closed loop with only the first arm extending from the closed loop. In other embodiments a second filament is coupled to the capture element. The second filament may have all features, aspects and uses as the first filament and all such features, aspects and uses are incorporated for the second filament. For example, the second filament may have a second leading portion which may have any of the characteristics, features and uses of the first leading portion of the first filament. The second filament may be coupled to the first filament and may even be being integrally formed with the first filament. The first concave portion and a second concave portion formed by the second filament may each extend 90-180 degrees when the capture element is in the open position.

The foregoing is a summary, and may be limited in detail. The above-mentioned aspects, as well as other aspects, features, and advantages of the present technology are described below in connection with various embodiments, with reference made to the description, claims and accompanying drawings.

BRIEF DESCRIPTION OF THE DRAWINGS

FIG. 2A illustrates a first embodiment of the filament predetermined shape.

FIG. 2B illustrates a second embodiment of the filament predetermined shape.

FIG. 2C illustrates a third embodiment of the filament predetermined shape.

FIG. 2D illustrates a fourth embodiment of the filament predetermined shape.

FIG. 2E illustrates a first embodiment of the filament predetermined shape.

FIG. 2F illustrates a first embodiment of the filament predetermined shape.

FIG. 2G illustrates a first embodiment of the filament predetermined shape.

FIG. 2H illustrates a first embodiment of the filament predetermined shape.

FIG. 2I illustrates a first embodiment of the filament predetermined shape.

FIG. 2J illustrates a first embodiment of the filament predetermined shape.

FIG. 2K illustrates a first embodiment of the filament predetermined shape.

FIG. 4J illustrates the clot engagement element and clot fully retracted into the container element.

FIG. 4K illustrates the distal end of the container element partially closed.

FIG. 4L illustrates the distal end of the container element further closed.

FIG. 4M illustrates the distal end of the container element inverted.

FIG. 4N illustrates the distal end of the container element further inverted.

FIG. 4O illustrates the microcatheter and clot engagement element retracted.

FIG. 6D illustrates the aspiration catheter and clot retracted into the container element.

FIG. 6E illustrates the distal end of the container element partially closed.

FIG. 6F illustrates the distal end of the container element further closed.

FIG. 6G illustrates the distal end of the container element inverted.

FIG. 6H illustrates the distal end of the container element further inverted.

FIG. 9D illustrates the distal end of the container element further closed and retracted.

FIG. 9E illustrates the container element with the distal end of the device substantially closed.

FIG. 9F illustrates a perspective view of the container element.

FIG. 12A illustrates an embodiment of the device with a filament catheter with the distal opening in an open position.

FIG. 12B illustrates an embodiment of the device with a filament catheter with the distal opening in a closed position.

FIG. 14A illustrates an embodiment of the device with a filament excess length in the constrained position.

FIG. 14B illustrates an embodiment of the device with a filament excess length in the deployed position.

FIG. 14C illustrates an embodiment of the device with a filament excess length in the closed position.

DETAILED DESCRIPTION

Figure 1:
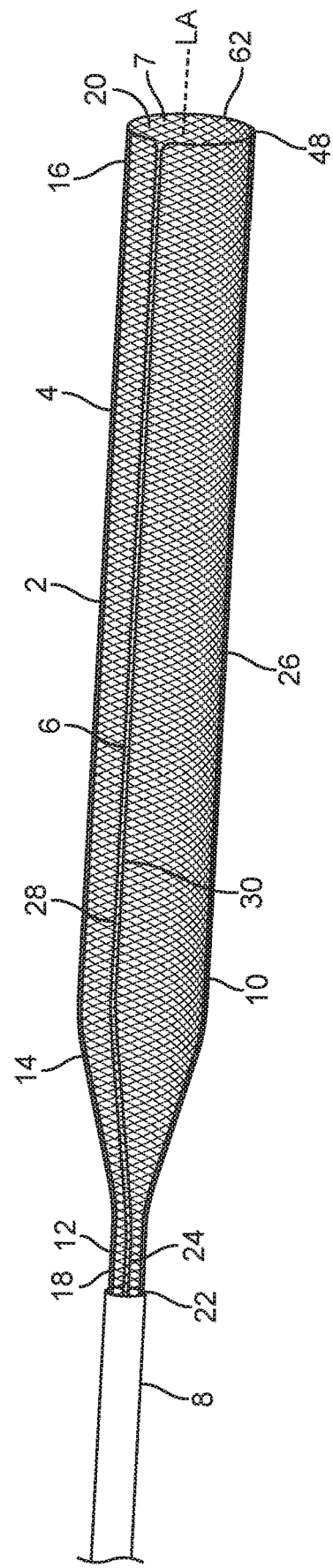
FIG. 1 illustrates an embodiment of the device in an isometric view.

In FIG. 1, a device 2 to contain and remove material from a blood vessel is shown. The device 2 includes a container element 4, a first filament 6, and a constraining catheter 8. The device 2 is shown in a generally deployed configuration with the container element 4 unrestricted by the constraining catheter 8 and the first filaments is not under significant tension. The various configurations and procedural steps of the device 2 will be described in greater detail below. Aspects of the present invention are described with reference to a single or limited number of embodiments, however, it is understood that all features, aspects and methods are incorporated into all applicable embodiments described herein even though not expressly mentioned or set forth.

The container element 4 has a vessel diameter portion 10 and a small diameter portion 12 with a proximal funnel area 14 between them. The container element 4 is connected to the first filament 6 toward a distal end 16 and the constraining catheter 8 toward a proximal end 18. The connection of the first filament 6 toward the distal end is configured such that when proximal tension is applied to the first filament 6, a distal opening 20 of the container element 4 reduces in size from an open position of FIG. 5A to a closed position of FIG. 5E and may also move proximally as described below. The open position defines a perimeter of the distal opening 20. The constraining catheter 8 may slide axially along the length of the container element 4 and is configured to constrict the container element 4 and position the container element 4 within a chamber 22 (which may be a lumen 24). As will be shown in the images below, as the constraining catheter 8 slides distally over the container element 4, the container element 4 constricts and enters the constraining catheter 8 to load the container element 4 within the constraining catheter 8 for delivery through the vasculature. The entirety of the container element 4 may fit within the constraining catheter 8. As the constraining catheter 8 is then moved proximally relative to the container element 4, the container element 4 is configured to extend out of the constraining catheter 8 and may expand as defined by its unrestricted shape to deploy the container element 4 at or near the desired location to remove material. The container element 4 has a lumen 7 through which a clot retrieval device may be passed as detailed herein.

The constraining catheter 8 is advanced through a blood vessel with the container element 4 positioned in the chamber 22 and held in the collapsed position. The container element 4 has a sidewall 26 extending proximally from the distal opening 20 which surrounds and contains the material. The first filament 6 is coupled to the container element 4 to manipulate the container element 4 as described herein. The first filament 6 is also in a collapsed position when the container element 4 is collapsed within the chamber 22 of the constraining catheter 8. The first filament 6 may include a first arm 28 coupled to a first end 32 of a concave portion 34 and a second arm 30 coupled to a second end 36 of the concave portion 34. The concave portion 34 faces a longitudinal axis LA defined by the container element 4. As used herein, the longitudinal axis LA follows the geometry of the container element 4 at a geometric center of the sidewall 26 and may take any shape such as curved or segmented linear sections and may be substantially by the shape of the vasculature rather than an unbiased shape of the container element 4 in use. The concave portion 34 may support the open position of the distal opening 20 as described in further detail below.

The container element 4 and first filament 6 may be advanced through the blood vessel with the first filament 6 having a first leading portion 38 which extends from the distal end 16 of the container element 4 in the collapsed position. The first leading portion 38 may have a length L which extends from the distal end 16 of the container element 4 by at least 30%, or at least 50%, of an effective diameter ED of a perimeter P of the distal opening 20 in the open position. The first leading portion 38 may be free of attachments to the container element 4 and may extend distally at least 1.5 mm from the distal end 16 of the container element 4 in the collapsed position. The first leading portion 38 may form a first loop 40 which extends beyond the distal end 16 of container element 4.

The container element 4 may also be advanced through the vasculature with the first filament 6 defining a working length WL which is positioned at a relatively distal location when collapsed. The working length WL is defined as the length of the first filament 6 positioned within 10 cm of the distal end 16 of the container element 4. For example, the working length WL may include the combined length of the first arm 28, the second arm 30 and the concave portion 34 within 10 cm of the distal end 16. In an aspect of the invention, the working length WL of the first filament 6 changes by less than 70% of the effective diameter ED of the distal opening 20 in the open position when the container element 4 moves from the collapsed position to the released position. In a specific embodiment, the working length WL may be about 11.5 cm in the collapsed position and about 11.5 cm when the distal opening 20 is open.

The first leading portion 38 and working length WL both contribute to reducing the required length of the first filament 6 that must be drawn distally as part the working length WL to release the container element 4. The required length of the first filament 6 to be drawn distally may be further reduced by coupling the first filament 6 to the constraining catheter 8 so that the first filament 6 moves proximally with the constraining catheter 8 relative to the container element 4 when releasing the container element 4 and when closing the distal opening 20. Coupling the first filament 6 (specifically the first and second arms 28, 30) to the constraining catheter 8 in this manner further reduces the required length of the first filament 6 that must be manipulated since the first filament 6 needn't extend completely out of the patient like many conventional devices. Of course, the first filament 6 may also be independent of the constraining catheter 8 and extend out of the patient without departing from numerous aspects of the present invention.

The container element 4 is moved to a released position outside the chamber 22 by moving the container element 4, the constraining catheter 8 or both. The first filament 6 may move to the released position while the distal opening 20 simultaneously moves to the open position as the container element 4 is moved/positioned outside of the chamber 22. Simultaneous release of the sidewall 26 and opening of the distal opening 20 may be accomplished by coupling the first filament 6 (specifically the proximal end of the first and second arms 28, 30) to the constraining catheter 8 as described above. Alternatively, the distal opening 20 may be separately opened using the first filament 6 or some other structure after the container element 4 has been released without departing from numerous aspects of the invention. Thus, the open position may be achieved in any suitable manner in accordance with the present invention although aspects of the present invention provide for the first filament 6 to support the open position as now described.

Figure 9A:
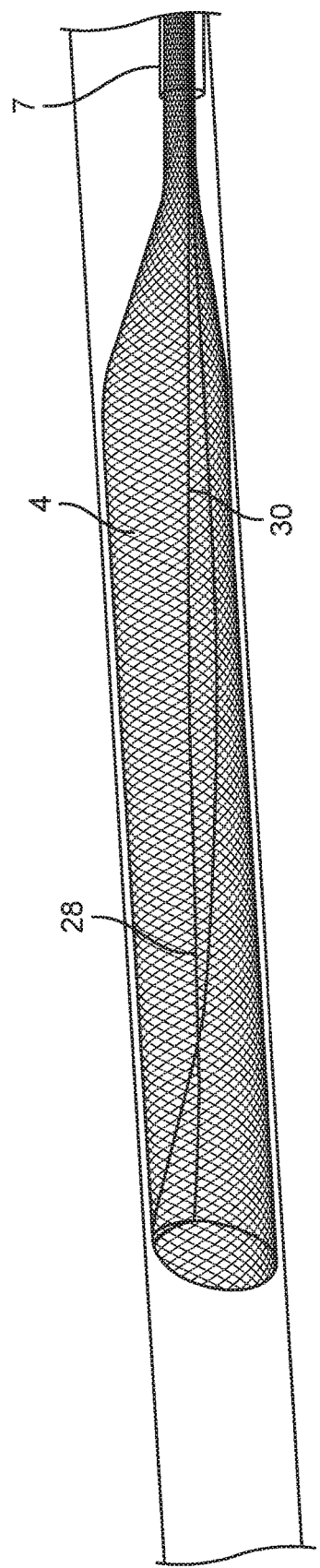
FIG. 9A illustrates an embodiment of part of the invented device within a simulated vessel.

The first filament 6 may be positioned and coupled to the container element 4 so that the natural unbiased shape (such as the shape of the concave portion 34) supports the open position of the distal opening 20. For example, the first filament 6 may have a predetermined shape 46 which defines a filament perimeter 48 which supports the open position of the container element 4. The predetermined shape 46 may extend around at least 120 degrees, at least 150 degrees or at least 260 degrees, around the distal opening 20 in the open position when viewed along the longitudinal axis LA. Stated another way, the first filament 6 may form the first concave portion 34 (oriented facing the longitudinal axis LA) which supports and moves the distal opening 20 to the open position when the container element 4 is released. Stated yet another way, the concave portion 34 has a shape larger than an unbiased shape of the distal opening 20 so that the concave portion 34 biases the distal opening 20 toward the open position. Stated still another way, the concave portion 34 may be restrained by the open position of container element 4 so that the concave portion 34 biases the distal opening 20 toward the open position. The first leading portion 38 may form the predetermined shape such as the concave portion 34. The first concave portion 34 may generally lie in a plane P which forms an angle A with the first arm 28 of 45-135 degrees in an unbiased position as shown in FIG. 9A. When the container element 4 is closed, the plane P forms the angle A with the first arm 28 of 135-180 degrees. The first concave portion 34 may also form a closed loop 50 which moves the distal opening 20 toward the open position when the container element 4 is in the released position as shown in FIG. 9A.

When the container element 4 is opened by the first filament 6, the first leading portion 38 may move into the container element 4 and form the concave portion 34 or, alternatively, move into the container element 4 and engage an inner surface 52 of the container element 4. Furthermore, the first filament 6 may apply an outward force to the inner surface 52 of the sidewall 26 over a longitudinal length of at least 2 cm of the container element 4 in the released position which may help anchor the device 2 when the material is moved into the container element 4 through the distal opening 20. The first filament 6 may also apply the outward force to the inner surface 52 over an angular extent of at least 180 degrees when viewed along the longitudinal axis LA. The first filament 6 (such as the first and second arms 28, 30) may also be substantially straight and may not apply an outward force to the sidewall 26 without departing from numerous aspects of the invention.

Once the distal opening 20 is in the open position, a clot engaging element 58 (which may engage in any suitable manner such as mechanical or suction engagement) is used to engage and, if necessary, dislodge the material to be removed. The material is then passed through the distal opening 20 and into the container element 4 by manipulating the clot engaging element 58, the container element 4, the first filament 6 or any combination thereof.

After the material to be removed is contained within the container element 4, the container element 4 is closed by tensioning the first filament 6 (such as the first arm 28 and second arm 30). The distal opening 20 may reduce in size from the open position so that the effective diameter ED is reduced by at least 80%. Stated another way, the effective diameter ED in the closed position may be no more than 1 mm.

The concave portion 34 may also be deformed when the first filament 6 is tensioned to close the distal opening 20. The first filament 6 (such as the concave portion 34) may be formed of a superelastic material which is elastically deformed when the distal opening 20 is closed. The concave portion 34 may also be plastically deformed or may be a simple tension element without departing from aspects of the invention.

The sidewall 26 of the container element 4 may also include an expandable portion 60 which may expand into engagement with the vessel 80 when the distal opening 20 is closed. The expandable portion 60 may be at least 10 mm long and within 10 mm from the distal end 16 of the container element 4. The expandable portion 60 may exert a radially outward force on the vessel wall when the container element 4 is closed by tensioning the first filament 6. The expandable portion 60 may be expanded beyond an unbiased shape by the first filament 6, for example, an effective diameter ED of the sidewall 26 along the expandable portion 60 may increase by at least 10% compared to an unbiased condition. Stated another way, when the container element 4 is moved to the closed position the first filament 6 causes an outward force on the expandable portion 60 which increases a radially outward force on the vessel wall by at least 10%.

The sidewall 26 of the container element 4 may also have a distal portion DP which reduces in length when the container element 4 is closed. The distal portion DP may extend 10 mm from the distal end 16 and reduces in length longitudinally by at least 20% when the container element 4 moves to the closed position. The distal portion DP may also expand in accordance with the expandable portion 60 and be fully or partially coextensive with the expandable portion 60.

The first filament 6 may also move proximally when the distal opening 20 is closed and may also move the distal opening 20 proximally as shown in FIGS. 9A-9F. The first filament 6 may be coupled to the constraining catheter 8 so that the first filament 6 is manipulated by the constraining catheter 8 and moves proximally with the constraining catheter 8 relative to the container element 4 when the container element 4 is released and when it is closed. In this manner, the first filament 6 is manipulated by the constraining catheter 8 which provides the advantages described herein such as a reduced length of the first filament 6 and possibly reduced forces on the vessel 80 when tensioning the first filament 6.

When the distal opening 20 is closed, the sidewall 26 may form an inverted IP portion which also moves the distal opening 20 to a position surrounded by the sidewall 26 (when viewed along the longitudinal axis LA). The sidewall 26 may also apply a radially inward force on the inverted portion IP (which is transmitted through the sidewall 26) to bias the distal opening 20 toward the closed position. The distal opening 20 may also invert when moving to the closed position or may remain uninverted with a small portion of the distal end of the sidewall 26.

The device 2 may also include a second filament 6A coupled to the container element 4 as shown in FIG. 2K wherein the same or similar reference numbers refer to the same or similar features as the first filament and all relevant features are incorporated here as previously mentioned. The second filament 6A may have a second leading portion 42 which distally extends beyond the distal end 16 of the container element 4 in the collapsed position. The second leading portion 42 extends at least 1.5 mm from the distal end 16 of the container element 4. The second leading portion 38A has a length which extends from the distal end 16 of the container element 4 which is at least 30%, and may be at least 50%, of an effective diameter of the perimeter of the distal opening 20 in the open position.

The second filament 6A may be coupled to the first filament 6 and may even be being integrally formed with the first filament 6. The second filament 6A may form a second concave portion 34A when the container element 4 is in the open position. The second concave portion 34A also moves the distal opening 20 toward the open position. The first concave portion 34 and the second concave portion 34A may each extend 90-180 degrees when the container element 4 is in the open position and viewed along the longitudinal axis LA.

Specific aspects of components of the invention are now described and these aspects, features, and method steps are incorporated into all applicable embodiments even though not expressly provided as mentioned above.

The container element 4 may be of any number of constructions. In some embodiments, the container element 4 may be a radially expandable element, such as a braid, laser cut stent, woven structure, or the like. In other embodiments, the container element 4 may be a non-compliant flexible bag or fabric such as a PET or PTFE materials. In other embodiments, the container material may be a compliant material such as a polyurethane, silicone, or the like that may stretch and expand as materials are pulled into it. In still other embodiments, the container material may be a combination of multiple constructions. For example, the container element 4 may have a bag construction in certain areas and a braid construction in other areas.

In some embodiments the container element 4 is a frame with an attached membrane or fabric. The frame may be comprised of a nitinol or stainless steel or plastic component that expands radially once delivered out of the constraining catheter 8. For example, the frame may be a nitinol tube that is laser cut and shape set to expand when not constrained. A fabric, such as a PTFE graft material or any other membrane material, may be connected to the frame to either provide local flow arrest and contain the clot once it is within the container element 4 or both. In some embodiments, the container element 4 may be combination of a braid and a frame element. For example, a small wire braid may extend over a frame structure, possibly on both the inner and outer surfaces of the frame structure.

In some embodiments the container element 4 is a braided wire construction. The braid wires may be nitinol, stainless steel, cobalt chromium, plastic, such as PET, or any other suitable material. The braid wire may contain radiopaque elements that allow it to be visualized under fluoroscopy such as a nitinol wire with a platinum core. Alternatively, the container element 4 may have connected markers that enable visualization. The number of wires in the braid may be between 12 to 128 wires or between 32-64 wires. The braid angle may be between 100-200 degrees or between 120-160 degrees. The braid wires may be between 0.0001"-0.0050" in diameter or between 0.0005"-0.0020". Alternatively, the braid wires may be non-circular and may be oval, flat, or rectangular ribbons. The braided geometry may allow the container element 4 to act like a Chinese finger trap where it decreases in diameter when it is elongated and increases in diameter when it is compressed. This may provide advantages such as allowing the device 2 to reduce in size when it is pulled out of the body and also secure its self against the vessel 80 when compressive loads are placed on portions of it such as through the filaments.

In some embodiments, the container element 4 has a predetermined shape 46 which is the unrestricted and unbiased shape that it naturally takes when no other components are restricting its movement at a given temperature. The predetermined shape 46 may be different shapes at different temperatures and as used herein shall be defined at normal body temperature. For instance, the container element 4 may be a braided construction comprised of Nitinol wire. The Nitinol braid may be given a predetermined shape 46 through a shape setting heat treatment where the container element 4 has a defined unrestricted shape. In some embodiments, the container element 4 is configured such that in an unrestricted shape it may expand to close the vessel size. For example, in applications of the middle cerebral artery (MCA), the container element 4 may be configured to expand to a diameter between 4 mm and 10 mm. Assuming an MCA has an average inner diameter of 4 mm, the container element 4 expands until it touches the intimal wall of the vessel 80. If the container element 4 is designed such that it expands to a diameter of 6 mm in air then it may provide a small to moderate amount of radial pressure on the wall of the vessel. By changing the unconstrained diameter of the container element 4, the amount of radial force exerted on the vessel may be modulated. Additionally, the radial expansion force may be adjusted by altering the characteristics of the container element 4. For example, if the container element 4 is a braided construction, the following parameters may be changed to increase or decrease the desire radial force on the vessel: braid angle, number of braided ends, braid material, braid wire diameter, braid wire cross sectional profile, braid coating, etc. The desired radial force may be different for different vessels and different anatomical locations. In some embodiments, the container element 4 has varying diameters or cross-sectional profiles along its length. For instance, the unconstrained diameter may be 8 mm in one or more locations and may be 4 mm in one or more locations. In addition, the cross sectional profile of the container element 4 may not be generally circular as is shown. The cross-sectional profile may be ovular, triangular, rectangular, or any other profile and may vary along the axial length of the container element 4. For example, in some locations the profile may be general elliptical with the semi-major axis in intimal contact with the vessel 80 and the semi-minor axis not in contact with the vessel 80. In other locations the cross-sectional profile may be circular with the entire circumference not in contact with the vessel wall. Any number of different shapes and configurations may be contemplated.

In other embodiments, the container element 4 may not be a fully tubular structure meaning that container element 4 may represent a rolled-up surface that may or may not connect to itself. For example, the container element 4 may be comprised of a laser cut pattern on a flat sheet of material that is then rolled to form a substantially circular shape but in which the two rolled edges may or may not connect to each other.

The container element 4 has a distal opening 20 toward its distal end that allows for the passing of materials into the container element 4 from the distal direction. The distal opening 20 may be configured such that in an unrestricted shape it is the same diameter as the sidewall 26 of the container element 4. The distal opening 20 defines a distal opening perimeter 64 along the rim of the distal opening 20. In other embodiments, the distal opening 20 may be larger or smaller than the sidewall 26 of the container element 4 when it is unrestricted such that the distal end 16 of the container element 4 tapers outward or inward. If the container element 4 is tapered outward at the distal end 16 of the container element 4 it may facilitate the smooth entrance of materials into the container element 4 and reduce the likelihood of clots from getting dislodged from the components which are retracting them. If the container element 4 is tapered inward at the distal end 16 of the container element 4 it may facilitate the closing of the container element 4 when the filament 6 is tensioned as will be discussed in more detail below. The distal opening 20 may have a cross-sectional area which is roughly the same as the cross-sectional area of the vessel 80 it is within. For example, in a 5 mm vessel 80 the cross-sectional area of the container element 4 may be between 10-30 mm$^2$ or between 18-22 mm$^2$ in a deployed configuration. The size of the distal opening 20 of the container element 4 may defined partially by the shape and size of the filament perimeter 48 48 as well. For example, the filament perimeter 48 may be such that it imparts an inward or an outward radial force on the distal opening 20 of the container element 4. In other embodiments, the filament 6 may impart an inward radial force in some locations and an outward radial force in other locations. In some embodiments, the container element 4 is a flexible bag material and the filament perimeter 48 fully defines the distal opening 20 size and shape.

When fully deployed the container element 4 may have a length of 1 cm-30 cm depending on the application. In a MCA application, the container element 4 may be between 4 cm-16 cm or 5 cm-10 cm. Standard stent retrievers are 3 cm-5 cm in length. Therefore, if the clot engagement element is a similar length, in order to fully capture and contain the clot engagement element, the length of the container element 4 may be on the order of 7 cm. However, as will be shown, the clot engagement element does not necessarily need to be fully captured by the container element 4. In any event, assuming a length of 7 cm of the container element 4 when unconstrained, the container element 4 may have a length of 14 cm when it is within the constraining element. This is commonly called foreshortening where the length of the container element 4 increases as it is radially constrained.

The container element 4 may have features which provide partial or full local flow arrest within the vessel such as a coating 108. In the embodiments where the container element 4 is a braid, the coating 108 may be a dipped or spayed coating 108 such as silicone. The silicone may be between 0.0001"-0.0050" thick or between 0.0005"-0.0010" thick. The silicone can provide a local flow arrest within the vessel 80 by covering portions of the braid so that blood flow is limited. Additionally, a coating 108 may provide further advantages of keeping the clot material that is captured by the device 2 better contained. For example, the container element 4 may be covered along its entire length such that the when it is deployed within the vessel 80 blood flow stops within the vessel 80 as blood cannot pass through the container element 4 which is in intimal contact with the vessel 80. In some embodiments, the coating 108 may cover only a portion of the container element 4 such as the proximal funnel such that the full or partial cross section of the vessel is blocking blood flow. In other embodiments the coating 108 may be over the entire container element 4. Alternatively, in the embodiments where the container element 4 is a braid, the braid windows or space between the braid wires may be so small that they provide local flow arrest or reduced flow. For example, if the braid windows are small enough it may provide local flow arrest without needing to be covered. In some embodiments it may be desirable to allow certain components of blood to pass through the braid such that the braid acts as a filter to substantially reduce blood flow but not fully arrest it.

The container element 4 may include more than one coating 108. In some embodiments, the container element 4 may have a hydrophilic coating 108 such as PTFE or other coating material to reduce friction of the container element 4 as it slides within the constraining catheter 8. The coatings 108 may be applied to the outer surfaces of the container element 4 to facilitate deployment of the container element 4 or may be applied to the inner surface 52 to facilitate movement of other components such as microcatheter 74 through the lumen of the container element 4. In other embodiments, the coating 108 may a drug coating to deliver an active pharmaceutical ingredient (API) to the vessel or local anatomy. This may include drugs such as tissue plasminogen activator (tPa). These may be separate or in addition to a coating 108 that provides flow arrest such as a silicone coating. For example, the container element 4 may have a silicone coating 108 which provides flow arrest and additionally have a hydrophilic coating to provide lubricity.

Local flow arrest may advantageously encourage retrograde collateral flow from the vessel such that the clot 78 is at a reduced risk of distal embolization since the flow may be reversed. In addition, it may allow for injection of contrast through a portion of the device 2 such as through the container element 4 or through the constraining catheter 8 which may facilitate identification of the thrombus within the vessel since there is no flow to carry the contrast away. Alternatively, the device 2 may be used to inject therapeutic agents such as tissue plasminogen activator (tPa).

The proximal end 18 of the container element 4 may reduce down to a small diameter portion 12. In some embodiments, the small diameter portion 12 is defined by a predetermined shape of the container element 4. For example, if the container element 4 is constructed of Nitinol the shape set configuration of the container element 4 may include the small diameter portion 12 at its proximal end 18. In other embodiments, the small diameter portion 12 may not necessarily be defined by a predetermined shape 46 but instead defined by the constraint of the constraining catheter 8. The small diameter portion 12 may be sized to fit within the inner lumen 24 of the constraining catheter 8. The inner diameter of the small diameter portion 12 may also be sized to allow for the passage of catheters and wires within it. Microcatheters 74 which are used to deploy stent retrievers may be on the order of 0.010"-0.040" outer diameter. Aspiration catheters which are used to grab clots through aspiration may be on the order of 0.020"-0.070" outer diameter. Therefore, the inner diameter of the small diameter portion 12 may be on the order of 0.010"-0.080" or may be on the order of 0.025"-0.060". This may allow other components to pass through the lumen of the container element 4 before and after the container element 4 is deployed.

The proximal end 18 of the container element 4 may continue through the constraining catheter 8 and out of the patient where it can be manipulated to change its relative position to the constraining catheter 8 and filaments. In some embodiments, the proximal end of the container element 4 may transition to a catheter or other suitable structure which is capable of moving the container element 4 forward and backward axially or rotationally. The catheter portion of the container element 4 may extend from out of the patient and may be manipulated either by the user, a delivery mechanism, or robotically. The proximal end 18 of the container element 4 may be connected to a vacuum source such that aspiration may be achieved through the lumen of the container element 4. As will be shown in subsequent description, the aspiration may be used to draw clots into the container element 4 and otherwise prevent distal blood flow.

Returning to FIG. 1, there is also shown a constraining catheter 8. The constraining catheter 8 may be comprised of any number of materials and constructions which exist in the field of catheters. In some embodiments the constraining catheter 8 may be a stainless steel braid reinforced catheter with a PTFE inner liner and a Pebax outer jacket. Any number of other suitable constructions and materials may exist. The construction and materials of the constraining catheter 8 may vary along its length to achieve the desired stiffness and force transmission. In the example of a MCA application, the constraining catheter 8 may be ideally delivered through an intermediate catheter 72 which has been placed in the cerebral artery. The inner diameter of intermediate catheters 72 used in thrombectomy procedures is typically on the order of 0.04"-0.08". Therefore, the outer diameter of the constraining catheter 8 may be on the order of 0.04"-0.08" or 0.05"-0.06". The inner diameter of the constraining catheter 8 may be sized to allow the passage of catheters and wires within it which are delivered distally including the container element 4. Therefore, the inner diameter of the constraining catheter 8 may be on the order of 0.010"-0.080" or may be on the order of 0.025"-0.060". The constraining catheter 8 may have a flared or constricted distal end 16 which facilitates the movement of the container element 4 into and out of the constraining catheter 8. For example, the diameter of the distal end 16 of the constraining catheter 8 may be flared by 0.001"-0.020" such that container element 4 is easily retracted into the constraining catheter 8 by the tapered section.

The constraining catheter 8 may extend out of the patient and can be manipulated by the user relative to the other components to guide the device 2 through the motions described in detail herein. In some embodiments, the constraining catheter 8 may be the same as the intermediate catheter 72 such that there is only one catheter. In some embodiments, the constraining catheter 8 may be connected to a portion of the filament 6 or filaments such that a proximal movement of the constraining catheter 8 relative to the container element 4 not only deploys the container element 4 but may also cause the distal opening 20 of the container element 4 to close by way of placing tension on the filament 6 as the constraining catheter 8 retracts. This will be described in greater detail below.

Returning to FIG. 1, there is also shown the filament 6. The filament 6 has the first arm 28 and the second arm 30 extending through the inner lumen of the container element 4 and connected at the filament perimeter 48 toward the distal end 16 of the container element 4. The filament 6 may extend through the assembly and out of the patient such that it can be manipulated by the user, a deployment mechanism, or robotically. Alternatively, the filament 6 may connect to a different component within the device 2 such as the constraining catheter 8 such that the motion of the constraining catheter 8 relative to the container element 4 may apply or remove tension from the filament 6. The filament 6 may be a monofilament 6 wire or may be any number of other constructions. For example, the filament 6 may be small coil made of any of the materials listed herein. Alternatively, the filament 6 may be a suture material such as a polypropylene or polyester. The material and construction of the filament 6 may vary along the length of the filament 6 and need not necessarily be the same along its entire length. In some embodiments the material is a round wire, whereas in other embodiments the snare may be a coil or a filament 6 of any number of cross-sections such as rectangular, ovular, sheet, or the like. Additionally, the cross-sectional shape and area of the snare filament 6 may vary along the length of the snare. In some embodiments, the filament 6 is constructed of multiple materials. For instance, a portion of the filament 6 may be flexible like a suture while other portions are elastic like Nitinol. In some embodiments, the filament 6 is a piece of Nitinol wire that is 0.0005"-0.0100" or 0.001"-0.004" in diameter. Alternatively, the filament 6 may be stainless steel, tungsten, cobalt chromium, plastic, or any other suitable material. The filament 6 may be shape set to have a predetermined shape such as a circle at the filament perimeter 48.

Turning now to FIG. 2A-2H, various predetermined shapes 46 of the filament 6 are shown. This is not intended to be an exhaustive list of any possible shape but merely to show the variety of shapes which one could configure the filament 6 to. In FIG. 2A, a filament 6 with a round filament perimeter 48 is shown. The filament perimeter 48 may be generally circular or ovular. The filament perimeter 48 transitions to a first arm 28 and a second arm 28 through a filament 6 bend. The first arm 28 and a second arm 28 extend roughly perpendicularly from a plane defined by the filament perimeter 48. As will be shown, the filament perimeter 48 may be at about the location of the distal opening 20 on the container element 4 and therefore the filament perimeter 48 may define a profile that is roughly the same as the inner surface of the vessel 80. In FIG. 2A, the filament perimeter 48 is about 330-360 degrees in circumference such that the first arm 28 and second arm 30 are in close proximity. In FIG. 2B, the filament perimeter 48 defines an arc that has an included circumference which is less and may be on the order of 200-330 degrees such that there is a gap between the filament bends 54 for the first arm 28 and the second arm 30. In FIG. 2C, the filament perimeter 48 defines an arc that has an included circumference which is on the order of 360-540 degrees such that there is an overlap of the filament perimeter 48. In FIGS. 2D and 2E, the filament perimeter 48 defines a plane that is not substantially perpendicular to the longitudinal axis of the vessel 80. Filament perimeter 48 is an oval that defines a plane which is askew to the central axis of the vessel 80. The application of this embodiment will be described in greater detail in subsequent figures. In FIG. 2D, the filament bends 54 are at a proximal portion of the filament perimeter 48 and in FIG. 2E the filament bends 54 are at a distal portion of the filament perimeter 48. In FIG. 2F, the filament perimeter 48 has a nipple 102 feature on its profile. The nipple 102 feature may facilitate the closing of the distal opening 20 when the filament 6 is in tension by providing a specific location where the filament 6 can bend to a tight radius which may allow the distal opening 20 to close tightly. In FIG. 2G, the filament perimeter 48 has an undulating profile 104 that can facilitate the weaving into and out of the container element 4 looped ends 106. In FIG. 2H, the filament perimeter 48 defines an arc that has an included circumference of 70-200 degrees such that the filament perimeter 48 only circumscribes a portion of the distal opening 20. In FIG. 2I, the first arm 28 and second arm 30 are joined at a filament junction 100 which is close to the filament perimeter 48. In FIG. 2J, they are joined at a filament junction 100 which is proximally further away from the filament perimeter 48. In these embodiments, there may only be a single filament 6 which extends proximally and therefore needs to be placed in tension. In FIG. 2K, there are two separate filament 6 elements which have individual filament perimeters 48. Each of the two filaments has a first arm 28 and a second arm 30. This embodiment may have less off axis loading of the container element 4 when the filaments 6 are placed in tension such that the distal opening 20 may remain generally concentric as it closes. Any number of other filament 6 configurations and shapes may be contemplated. In some embodiments the filament 6 may only have a first arm 28 and the filament perimeter 48 may terminate part way through the circumference. In such an embodiment, the end of the filament perimeter 48 may be connected to a part of the container element 4. In other embodiments, there may be two or more filaments 6 that connect to the distal end 16 of the container element 4. The distal end of each filament 6 may form a hook that is looped around the distal edge of the container element 4 such that there are a series of pull wires which can be activated independently or in conjunction with one another to place the distal end 16 of the container element 4 in tension. In other embodiments, the filament 6 may have a predetermined shape 46 that is generally straight wire and which is constrained to one of the shapes shown in FIG. 2A-2K by the shape of the distal end 16 of the container element 4. For example, the filament 6 may be threaded through the container element 4 and therefore held in a shape that resembles one of the shapes shown in FIGS. 2A-2K by nature of being connected to the container element 4.

The container element 4 may be connected to the filament 6 in any number of ways. In some embodiments where the container element 4 is a fabric or bag material, the distal end 16 of the container element 4 may be wrapped around the filament 6 and adhered to itself through the use of heat sealing or adhesives or any other suitable method. Alternatively, the filament 6 may weave through portions of the container element. In some embodiments, the container element 4 may include a laser cut stent structure. The stent may include features such as holes at the distal end which are configured for the filament 6 to weave through. In some embodiments, the container element 4 is a braided structure and the filament 6 may weave through the braid or looped ends 106 near or at the distal end 16 of the container element 4. The distal opening perimeter 62 and the filament perimeter 48 may be generally the same in some configurations such as when the device 2 is deployed and in an open configuration. In other configurations such as the constrained or closed configuration, the distal opening perimeter 62 and filament perimeter 48 are different shapes and lengths.

Figure 3:
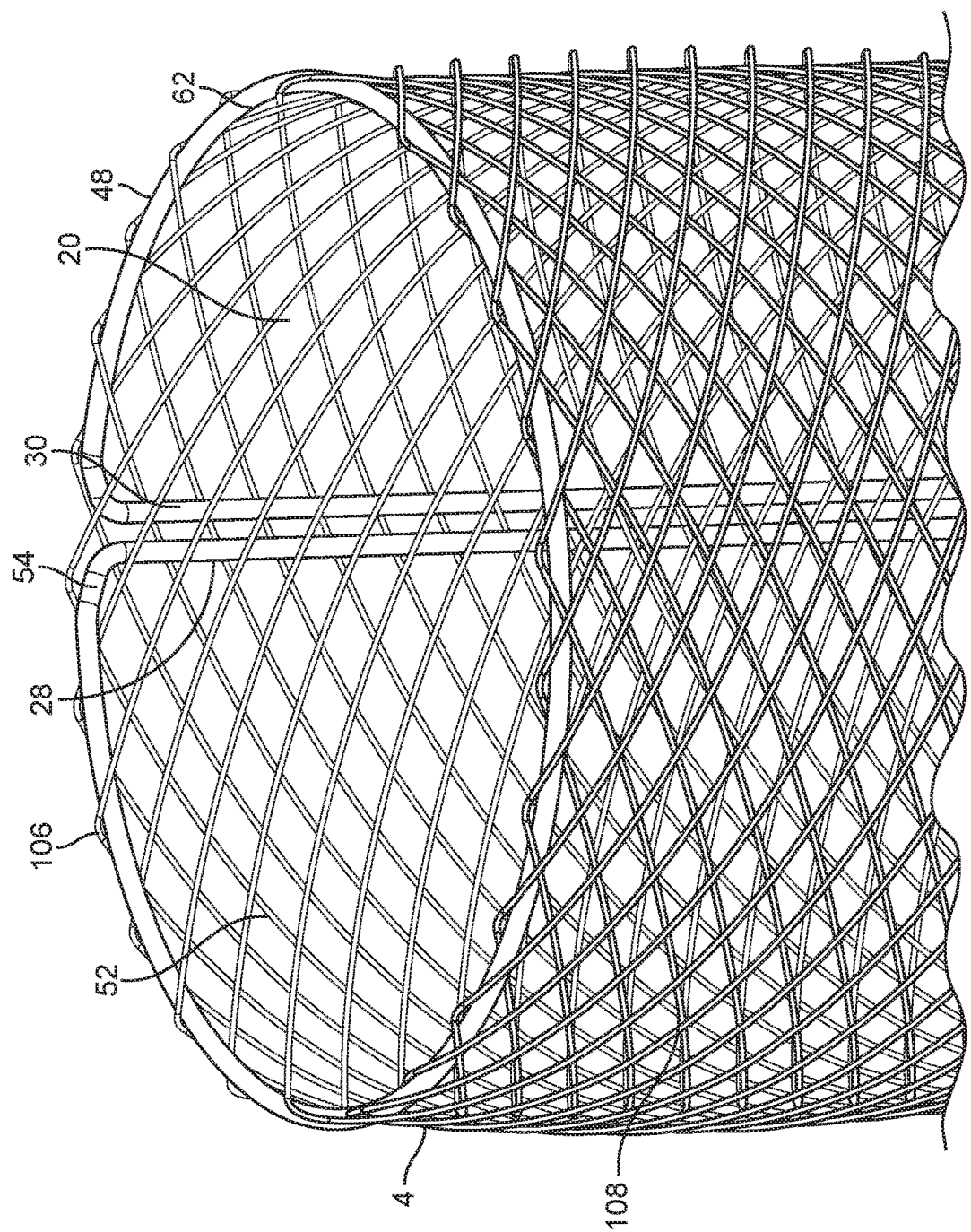
FIG. 3 illustrates a detailed view of the distal end of the container element.

In FIG. 3, a detailed view of the distal end 16 of an embodiment of the container element 4 is shown. The container element 4 is constructed of braided wires. The wires may double back on themselves as shown by terminating at one end of the container element 4 with looped ends 106. For example, at one end of the container element 4, the braided wires may form looped ends 106 by being wrapped around posts during manufacturing and then braiding the wires back over the already created braid. In this way, the looped ends 106 provide an atraumatic end within the vessel and also provide a location where the filament 6 can be woven through. The filament perimeter 48 may be woven through these braided looped ends 106 so that as the filament 6 is tensioned, it constricts the distal opening 20 of the container element 4 like a purse string or draw string. The filament 6 may weave through back and forth through each of the looped ends 106 or may weave through every other looped end 106 or any weave pattern. For example, the filament 6 may weave through only 4 locations of the braided looped ends 106 at 90 degrees apart from each other. The weave characteristics may dictate the friction necessary to open the distal opening 20 of the container element 4 once it is deployed. It may be advantageous to reduce the friction between the filament 6 and braid by limiting the number of woven looped ends 106 so that the radial expansion force of the container element 4 can easily overcome the friction of the filament 6 expanding as it opens. In some embodiments the filament perimeter 48 can wrap around 360 degrees at the distal end. In other embodiments the filament 6 can cross over itself and wrap around between 360 and 720 degrees. In still other embodiments the filament 6 may only wrap around 90 to 360 degrees so that only a portion of the distal end 16 of the container element 4 has the filament 6 wrapping around. In still other embodiments, the filament 6 is only attached to a small section of the container element 4 such as a one or two looped ends 106. The filament 6 may also only have a single wire returning proximally from the distal end 16. The filament 6 may form a loop at the distal end 106 but may connect back to itself such that two filaments 6 are not required to constrict the distal end 16. Any number of filaments 6 may be used and connected to the container element 4 and may be actuated independently or in conjunction.

In some embodiments, the first arm 28 and the second arm 30 may weave through sections of the container element 4 along the axial length of the container element 4. This may keep the arms 28, 30 constrained to the sidewall 26 of the container element 4 such that they do not get in the way of other components which are moving within the container element 4. Additionally, keeping the filament 6 constrained to the sidewall 26 of the container element 4 may facilitate the closure of the distal opening 20 by directing the force applied to the distal opening 20 in a radial direction rather than a proximal direction. In other embodiments, the first arm 28 and the second arm 30 do not weave through the side wall 26 of the container element 4 and are left free. In this embodiment, they may be configured through a predetermined shape 46 to remain biased against the sidewall 26 or may be configured to take any number of other shapes.

The container element 4 and filament 6 are configured such that when they are deployed the container element 4 is unrestricted and the filament 6 is not under a significant amount of proximal tension. In this condition, the distal opening 20 of the container element 4 is open and positioned to receive clot 78 material from the distal direction. The distal opening perimeter and filament perimeter 48 may be generally the same shape and length in this position. When tension is then applied to the filament 6, the filament perimeter 48 and distal opening 20 may begin to move proximally. The distal opening 20 is configured to constrict and close as additional tension is applied to the filament 6. In this manner, the closure of the distal opening 20 is actuated by the tension applied to the filament 6. The distal opening perimeter P may reduce in length as the looped ends of the braid get closer together while the filament perimeter 48 is the same fixed length. However, the amount of the filament perimeter 48 that the distal opening perimeter 62 occupies is less. For example, in the deployed configuration the distal opening perimeter 62 may overlap with about 60% to 100% or 80% to 100% of the filament perimeter 48. In the closed configuration, the distal opening perimeter 62 may overlap with about 1% to 30% or 5% to 15% of the filament perimeter 48. The filament perimeter 48 has remained the same fixed length but its shape has changed and only a portion of it has the distal opening perimeter 62 overlapping.

In some embodiments the opening of the distal opening 20 may be actuated by the removal of tension from the filament 6. As tension is removed, the filament 6 may return to its predetermined shape 46 and likewise the container element 4 may return to its unrestricted predetermined shape. As such the distal opening 20 may return to an open position. In other embodiments, once the distal opening 20 is closed by means of applying tension to the filament 6, the distal opening 20 will not open upon release of the tension to the filament 6. In this manner the device 2 locks into a generally closed distal opening 20 once tension is applied and even the removal of the tension does not allow the distal opening 20 to open.

In other embodiments the filament perimeter 48 may be located substantially away from the distal end 16 of the container element 4. For instance, rather than weaving the filament 6 through the looped ends of the braid the filament 6 may be woven through any section of the container element 4 along its axial length. In some embodiments, the filament perimeter 48 may not necessarily be woven through any feature on the container element 4. For example, the filament perimeter 48 may exist primarily on the outer surface of the container element 4 and may simply pinch the outside of the braid at a given location along the axial length of the container element 4 instead of constricting it like a purse string. In such an embodiment, the first arm 28 and second arm 28 may still enter the inner lumen of the container element 4 by threading through a portion of the container element 4. The distal opening 20 and distal opening perimeter 62 may be defined by the location of the filament perimeter 48 or may be defined by the distal end 16 of the device 2.

While filament 6 is generally described herein as a snare type mechanism that cinches the distal opening 20 of the container element 4, any other types and closures mechanisms may be contemplated. For example, the container element 4 may contain one or more flaps 88 at its distal end that are connected to one or more filaments. The one or more flaps 88 may be folded inward by tensioning the filaments so that the flaps collapse and restrict the distal opening 20. In other embodiments, twisting mechanisms may be used to constrict the distal opening 20 of the container element 4. For example, the distal end 16 of the container element 4 may be held generally stationary while the body of the container element 4 is twisted clockwise. In this manner the distal end 16 of the container element 4 may constrict and close the distal opening 20. Any number of other closure mechanisms may be contemplated.

Figure 4A:
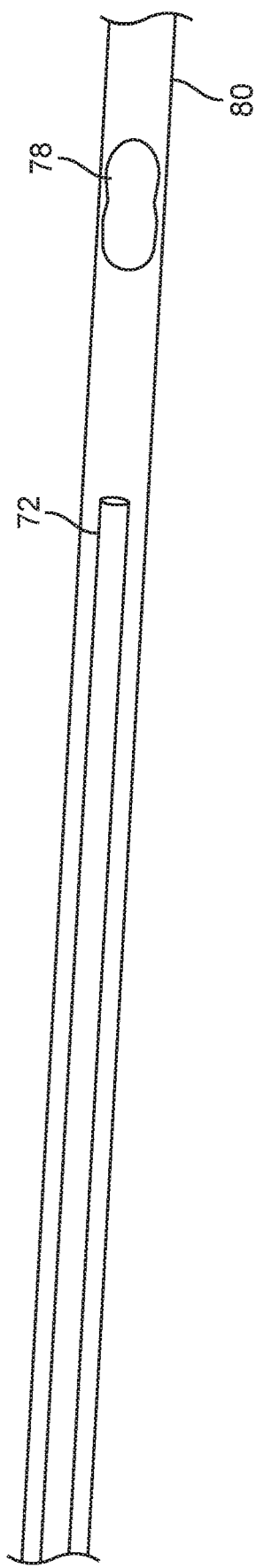
FIG. 4A illustrates an intermediate catheter within a vessel which includes a clot.
Figure 4B:
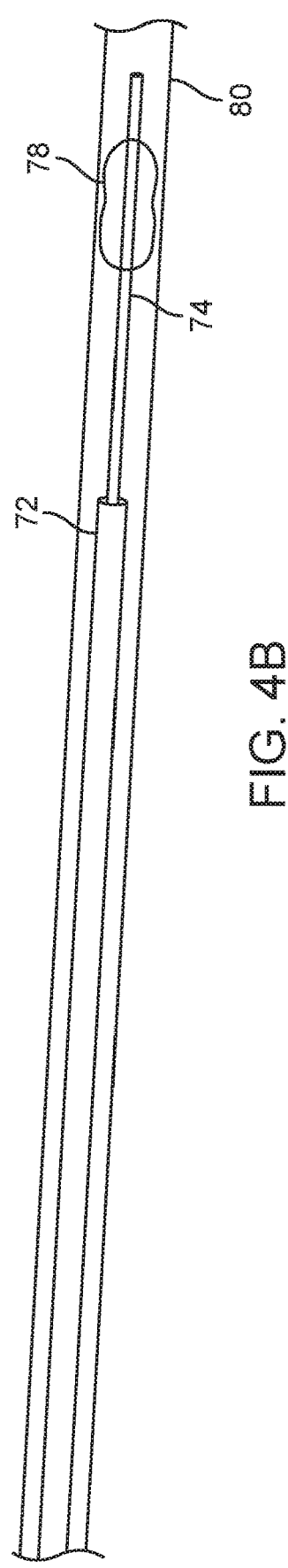
FIG. 4B illustrates a microcatheter traversing the clot.
Figure 4C:
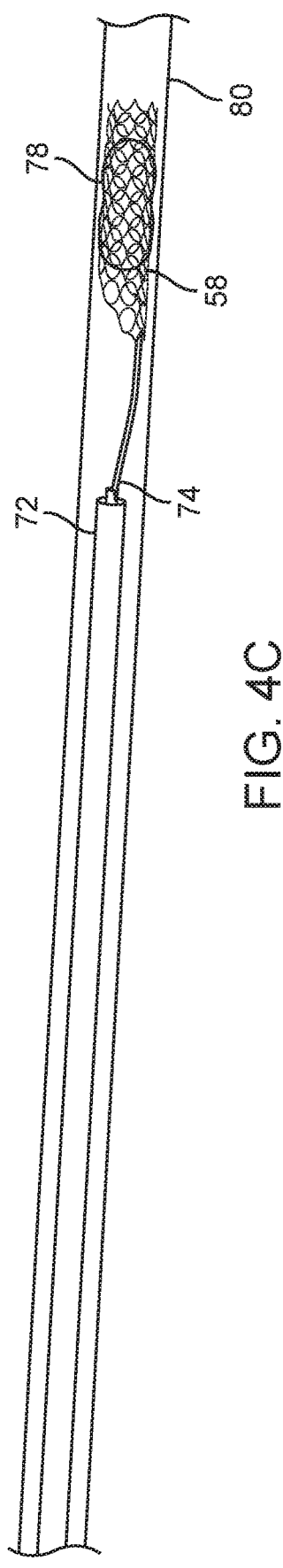
FIG. 4C illustrates the microcatheter retracted and a clot engagement element engaged with the clot.
Figure 4D:
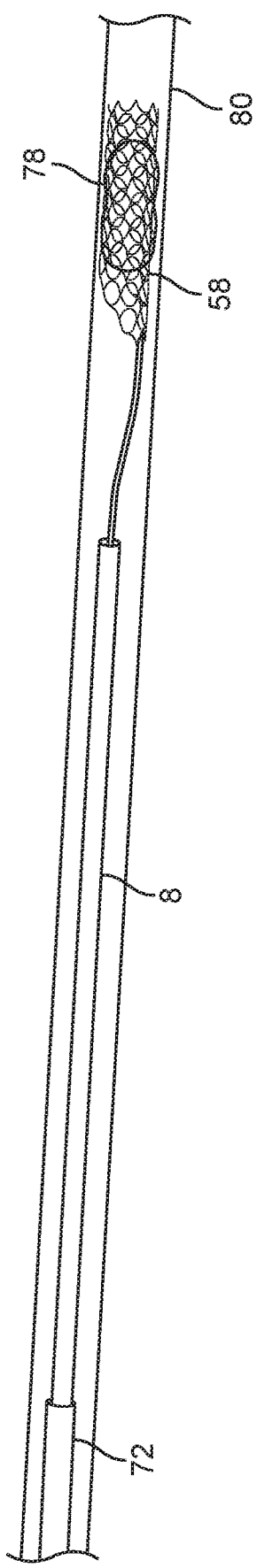
FIG. 4D illustrates the intermediate catheter retracted and a constraining catheter in place.
Figure 4E:
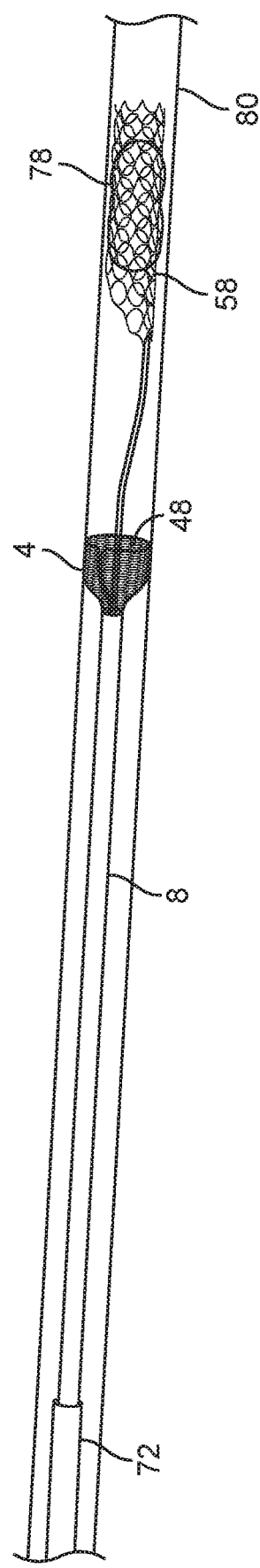
FIG. 4E illustrates the constraining catheter beginning to be retracted and the container element partially deployed.
Figure 4F:
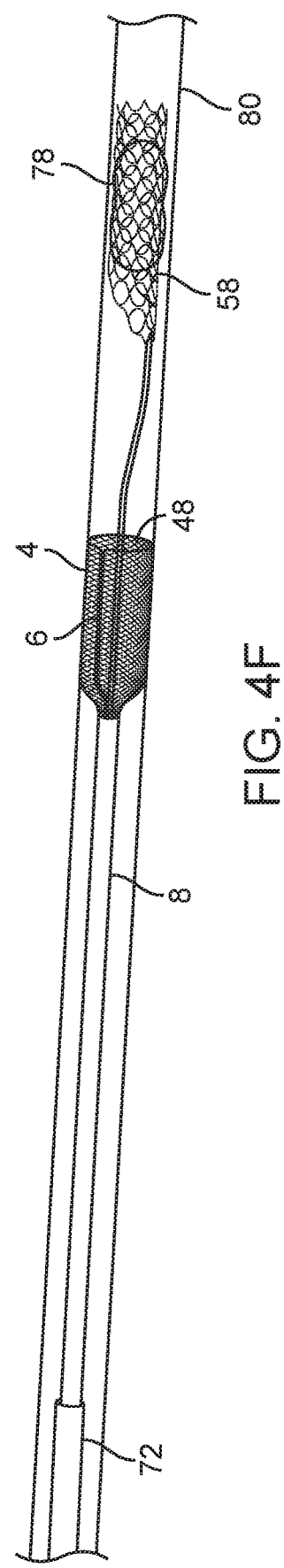
FIG. 4F illustrates the constraining catheter further retracted and the container element further deployed.
Figure 4G:
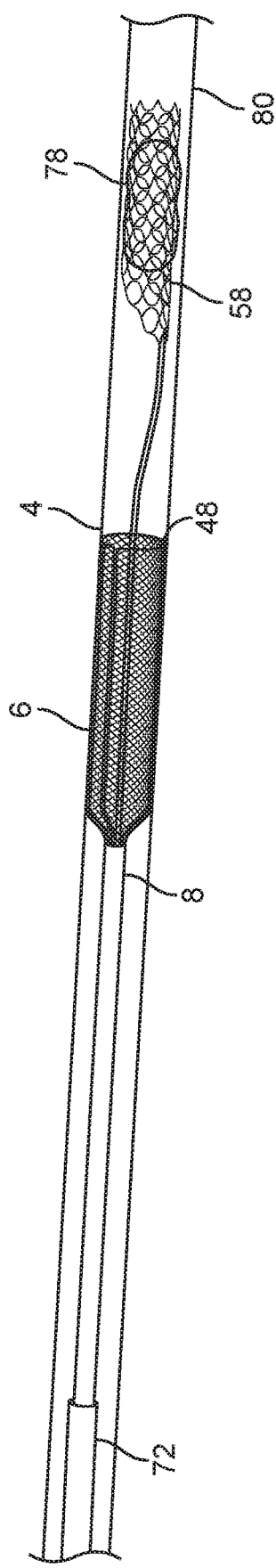
FIG. 4G illustrates the constraining catheter further retracted and the container element further deployed.
Figure 4H:
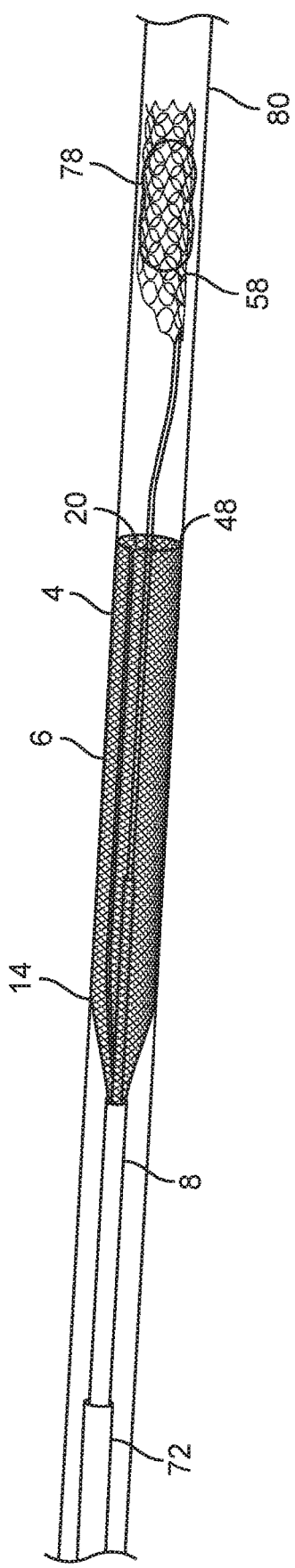
FIG. 4H illustrates the constraining catheter fully retracted and the container element fully deployed.
Figure 4I:
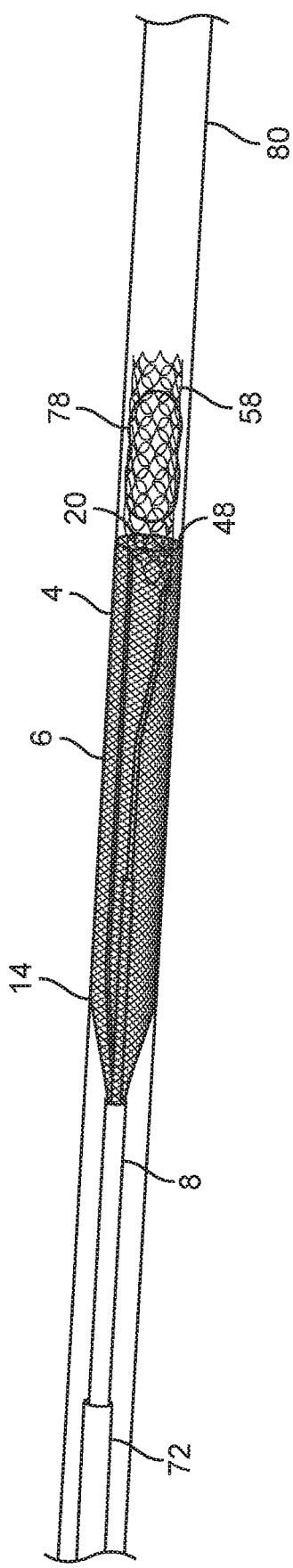
FIG. 4I illustrates the clot engagement element and clot partially retracted into the container element.
Figure 4P:
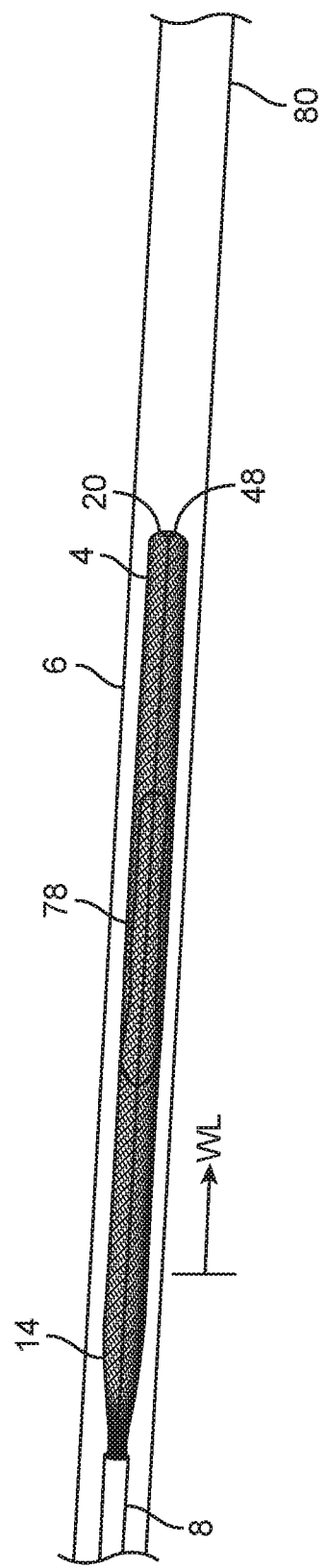
FIG. 4P illustrates the constraining catheter and container element beginning to be retracted from the vessel.

Turning now to FIG. 4A-4P, a first embodiment of the device 2 is shown. In FIG. 4A, an intermediate catheter 72 is shown within a vessel which contains a clot. The intermediate catheter 72 may be any standard size such as between 0.010" to 0.500" OD or between 0.050" and 0.110" outer diameter depending on the anatomical location it will be used. It may be comprised of any typical materials used for such catheters, such as Pebax, polyimide, PEEK, multi-layer braided composite, or any other suitable material or composition. The vessel shown may be a cerebral artery such as the middle cerebral artery (MCA) or any other vessel within the body of a human or animal. The size of the intermediate catheter 72 may depend on the size of the vessel 80 and the expanded size of the container element 4 as will be shown. Larger vessels 80 often will require larger catheter sizes while smaller vessels 80 often will require smaller catheter sizes. The intermediate catheter 72 is placed proximal of the clot 78 and in a position to deploy other parts of the invented device 2.

In FIG. 4B, a microcatheter 74 has traversed the clot 78. The microcatheter 74 may be any suitable size such as 0.010" to 0.080". Prior to traversing the clot 78 with the microcatheter 74, a guidewire or other such element may be included and used to guide the microcatheter 74 across the clot. In some embodiments a guidewire may be required while in other embodiments a guidewire is not necessary. If a guidewire is used, it will often be withdrawn once the microcatheter 74 traverses the clot and the clot engagement element may then be inserted into the microcatheter 74 while it is traversing the clot. This places the clot engagement element 58 across the clot 78 so that it is in an optimal location when the microcatheter 74 is withdrawn.

In FIG. 4C, the microcatheter 74 is withdrawn and a clot engagement element 58 is left behind and engages with the clot. The clot engagement element 58 may be a stent retriever type design as shown but it may also be any other element suitable for pulling a clot proximally. In the embodiment shown, the clot engagement element 58 has a series of struts or interwoven elements that expand radially outward when it is not constrained which allow it to engage with the clot 78 and pull it proximally when the clot engagement element 58 is retracted. In other embodiments, the clot engagement element 58 is a balloon that is inflated distally to the clot 78 such that as it retracts, it pulls the clot 78 proximally with it. In still other embodiments, the clot engagement element 58 is a Nitinol wire with a convoluted shape such that when it is deployed it likewise engages with the clot 78 and secures itself in different areas of the clot. Any number of other clot engagement elements 58 may be contemplated.

In FIG. 4D, the intermediate catheter 72 is withdrawn, exposing a constraining catheter 8 which constrains the container element 4. In some embodiments there is no need for a constraining catheter 8 and the intermediate catheter 72 can constrain the container element 4 such that when it is retracted, as will be shown with the constraining catheter 8, the container element 4 is deployed. In some embodiments, the constraining catheter 8 with the container element 4 is within the intermediate catheter 72 during the navigation and delivery of the microcatheter 74 while in other embodiments it is advanced into position within the intermediate catheter 72 at some point between navigation and after the clot engagement element 58 has been deployed.

In FIGS. 4E-4H show a container element 4 being deployed within the vessel. In FIG. 4E, the constraining catheter 8 begins to be retracted and the distal end 16 of the container element 4 is deployed. The initial deployment steps of the filament perimeter 48 and distal end 16 of the container element 4 will be shown in greater detail in FIGS. 7A-7G.

In the embodiment shown in FIGS. 4E-4H, the container element 4 has a relatively consistent unconstrained diameter of 3 mm-6 mm and is sized such that when deployed within an MCA, it is uniformly in contact with the vessel wall. In FIG. 4E, the container element 4 is partially deployed and a filament perimeter 48 exists at the distal end 16 of the container element 4. The plane formed by the filament perimeter 48 is generally perpendicular to the longitudinal axis of the vessel 80.

In FIG. 4F, the container element 4 is more deployed out of the constraining catheter 8. As is shown, when the container element 4 comes out of the constraining catheter 8 it self-expands against the vessel 80. In other embodiments, the container element 4 may be actively expanded with the use of balloons, shape memory materials such as nitinol that transition at a given applied temperature, or any other means. For example, in some embodiments the constraining catheter 8 may be fully retracted before the container element 4 is actively expanded in the vessel. The filament perimeter 48 comes out of the constraining catheter 8 and automatically expands to the vessel 80 with the container element 4 open. In some embodiments the filament perimeter 48 may come out of the constraining catheter 8 in a fully or partially closed configuration and then may be opened once in place.

In FIG. 4G, the container element 4 is more deployed as the constraining catheter 8 is further retracted. In some embodiments, the constraining catheter 8 is retracted to deploy the container element 4. In other embodiments, the container element 4 may be advanced out of the constraining catheter 8. In still other embodiments there may be a combination of retracting the constraining catheter 8 and advancing the container element 4. In fact, as shown the axial length of the container element 4 is significantly longer when it is within the constraining catheter 8. Therefore, as the container element 4 is deployed by retracting the constraining catheter 8, the proximal end of the container element 4 must be advanced if the distal end of the distal end 16 of the container element 4 is to stay in a fixed location. Since the container element 4 may be in contact with the vessel 80 when it is deployed it may be advantageous to keep any areas which are contacting the vessel 80 stationary so as not to injure the vessel 80. Therefore, a retraction of the constraining catheter 8 may be accompanied by an advancing of the proximal end 18 of the container element 4.

In FIG. 4H, the container element 4 is shown in a fully deployed state. The constraining catheter 8 has been retracted far enough that a proximal funnel area 14 of the container element 4 is exposed. The proximal funnel area 14 may be a predetermined shape that the container element 4 has at the proximal end 18 of its vessel diameter portion 10. The proximal funnel area 14 tapers the vessel diameter portion 10 to the smaller diameter portion 12 that fits within the constraining catheter 8. It should be noted that a proximal funnel area 14 may not be required since the container element 4 may naturally come out of the constraining catheter 8 in a funnel shape as it is being deployed. As will be discussed the proximal funnel area 14 may provide local flow arrest in the vessel 80. In some embodiments, the user may select the length of the container element 4 to deploy. For example, in the case of capturing small clots only ¼-½ of the vessel diameter portion 10 of the container element 4 may be deployed. Other times in the case of longer clots 78, the full length of the vessel diameter portion 10 may be deployed. The amount of container element 4 may be selectable by the user.

As shown in FIG. 4H, the microcatheter 74 may remain within the device 2 or it may be removed from the patient at any point during the procedure. In some embodiments, the microcatheter 74 is a mono-rail catheter that allows it to be removed while keeping the clot engagement element in place. In other embodiments, the microcatheter 74 remains in place and may be used in subsequent steps to sheath the clot engagement element 58 once the clot is captured within the container element 4.

In FIG. 4I the clot engagement element 58 with the clot 78 is withdrawn toward the distal opening 20 of the container element 4. As the clot engagement element 58 reaches the distal opening 20 of the container element 4 it enters the container element 4. The distal end 16 of the container element 4 may be flared outward, either by its predetermined shape or by a radial force from the filament perimeter 48, so that the clot engagement element 58 enters smoothly and does not get stuck on any part of the container element 4 as it enters. Alternatively, the distal end 16 of the container element 4 may be constricted partially.

In FIG. 4J, the clot engagement element 58 has been withdrawn so that it is entirely within the container element 4. Some embodiments of the clot engagement element 58 may leave components outside of the container element 4. One critical aspect is that most or all of the clot 78 that will be withdrawn from the patient is within the container element 4 even though pieces of the clot engagement element 58 may remain outside of the container element 4. For example, the clot engagement element 58 may be a balloon that pulls the clot 78 into the container element 4 but itself does not go fully within the container element 4. In some embodiments, portions of the clot engagement element 58, guidewire, microcatheter 74, or any other structure may remain distal to the distal opening 20. In this manner, when the distal opening 20 is fully or mostly closed, devices may be navigated beyond the distal end of the distal opening. For example, after retracting a clot engagement element 58 with a clot 78 into the container element 4, the distal opening 20 may be disclosed as described herein but with a portion of the clot engagement element 58 remaining distal. The user may then use a microcatheter 74 to constrict the clot engagement element 58 again and advance the microcatheter beyond the distal opening 20. In this manner, a clot engagement element 58 may be used again to engage with additional pieces of clot 78 which were not retracted the first time. Such an embodiment can be used when the clot engagement element 58 is a stent retriever or an aspiration catheter 76. The distal opening 20 can be opened by releasing tension on the filament 6 and the additional clot 78 material can be retracted within the containing element 4. This process may be repeated as many times as necessary and may be useful in removing significant amounts of clot 78 or in instances where only fragments of the clot 78 can be engaged.

Figure 5B:
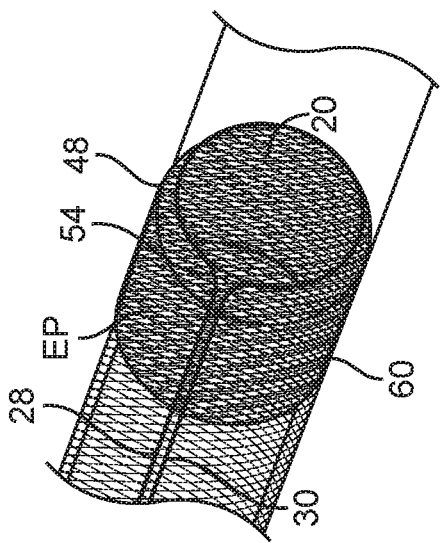
FIG. 5B illustrates a detailed view of the distal end of the container element partially closed.
Figure 5D:
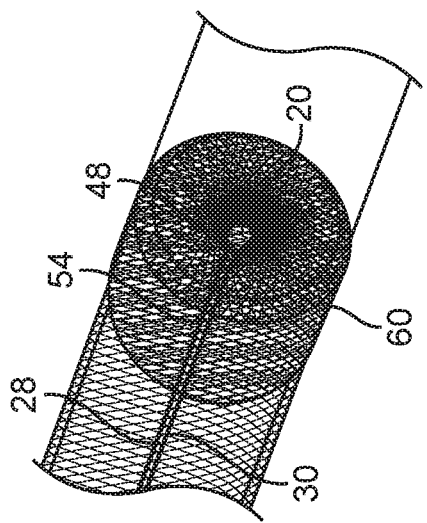
FIG. 5D illustrates a detailed view of the distal end of the container element inverted.
Figure 5A:
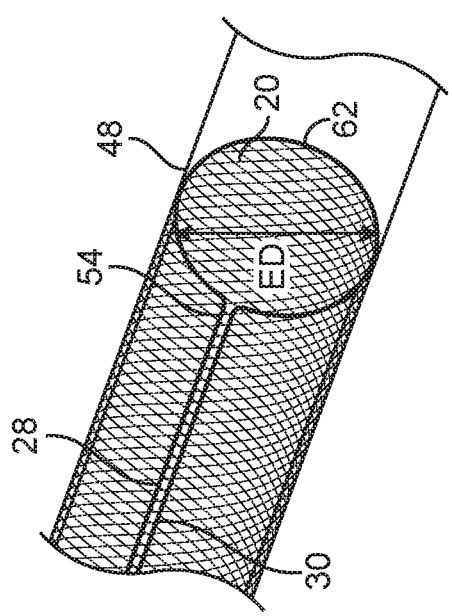
FIG. 5A illustrates a detailed view of the distal end of the container element open.
Figure 5C:
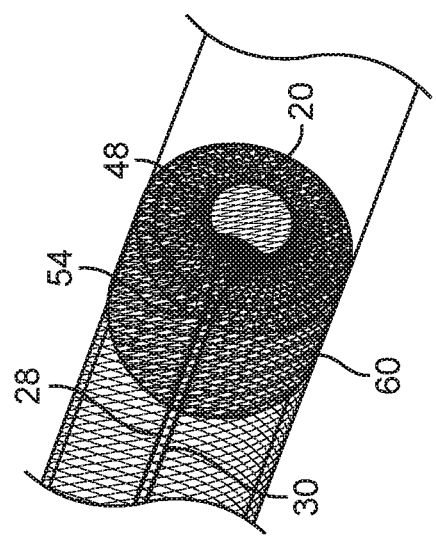
FIG. 5C illustrates a detailed view of the distal end of the container element further closed.
Figure 5E:
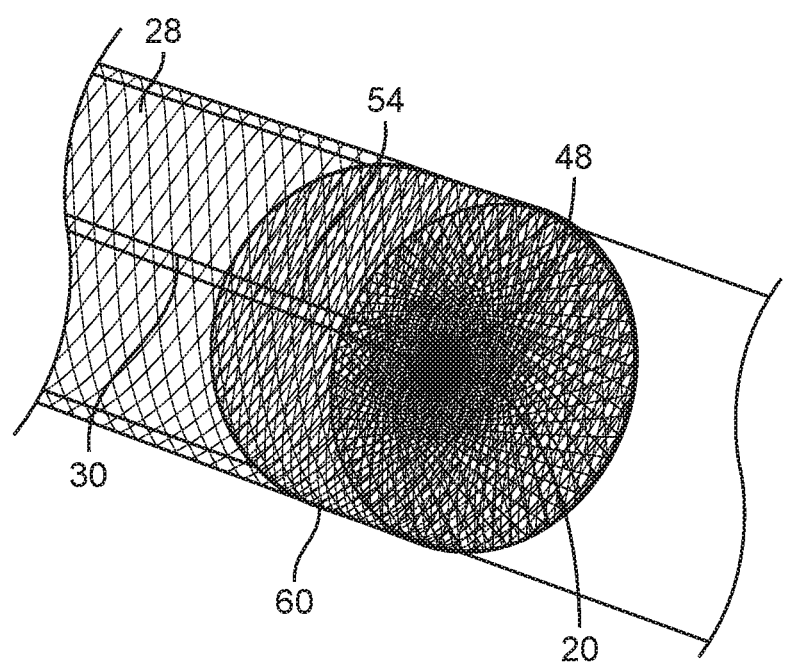
FIG. 5E illustrates a detailed view of the distal end of the container element further inverted.

In FIGS. 5A-5E, the distal end 16 of the container element 4 and filament perimeter 48 are shown in greater detail during the closure of the distal opening 20. In FIG. 5E, the container element 4 is shown with the distal opening 20 in the open configuration where the clot engagement element 58 can be withdrawing into the container element 4.

In FIG. 4K, the distal opening 20 of the container element 4 begins to close. In the embodiment shown, a proximal tension is applied to the first arm 28 or second arm 30 or both. The tension can be equal across the arms 28, 30 or can be different. In some embodiments only the first arm 28 is tensioned while in other embodiments both arms are tensioned. The tension in the filament 6 imparts a proximally directed force on the distal end 16 of the container element 4. This may be translated into a compressive load on the container element 4. During the proximal loading of the filament 6, the filament perimeter 48 begins to move proximally and change shapes. Additionally, the distal end 16 of the container element 4 and distal opening 20 begin to move proximally as a result of the proximal force applied through the filaments 6. The braided structure may be designed to increase in diameter when it is constricted and decrease in diameter when it is lengthened. In the embodiments where the container element 4 is of a woven or braided construction, as the distal end 16 of the container element 4 moves proximally it may expand radially. At some point the radially expansion may be constrained by the vessel 80 and the container element 4 may then impart a radially outward force on the vessel 80. In some embodiments where the container element 4 is already in close approximation with the vessel 80 the container element 4 may not substantially expand when it is placed under a compressive load but rather may directly impart a radially outward force. In some embodiments only a portion of the container element 4 such as the distal end 16 may expand radially and impart a radially outward force while in other embodiments a substantial amount of the container element 4 may do so. The outward force may facilitate in securing at least a portion of the container element 4 to the vessel 80 and prevent it from moving proximally. In this manner, the tension applied to the filament 6 may secure the container element 4 distally to the vessel 80 such that the distal opening 20 can be closed. If the container element 4 is not constrained and secured by the vessel 80, there must be a component or components which impart a reaction force to support the distal end while the distal opening 20 is closing. In some embodiments this may be the container element 4 itself which may have structures and frames to support a compressive load. This may be true in the case of a framed configuration of the container element 4. Alternatively, additional catheters or support structures may provide a reaction force to hold the distal end while the distal opening 20 is closed. In some embodiment which will be shown in greater detail below, the filament 6 may be supported by a filament catheter 82 which can provide such a function. An advantage of the braided structure of the container element 4 described herein is that the device 2 can be very flexible and no stiff or rigid components are required because it is secured to the vessel 80 itself and only when tension is applied to the filament 6.

In FIG. 5B, a closer view of the distal end 16 is shown with the filament perimeter 48 beginning to constrict the distal opening 20. As can be seen, the filament perimeter 48 remains a fixed length is moving proximally such that the distal opening perimeter 62 is decreasing in length. The looped ends 106 of the braid are being constricted like a purse string with a pull wire. The distal opening perimeter 62 is occupying a smaller portion of the filament perimeter 48 as more tension is applied.

In FIGS. 4L and 5C, additional tension is applied to the filament 6 and the distal opening 20 is constricted further. The distal end 16 of the container element 4 and the filament perimeter 48 have moved further proximally. In FIGS. 4M and 5D, the filament perimeter 48 and distal opening 20 have moved further proximally such that they are within the sidewall 26 of the container element 4. The distal opening perimeter 62 now occupies a small portion of the original filament perimeter 48 at its very distal end. The container element 4 has inverted as the filament perimeter 48 moves proximally and a portion of the container element 4 is secured by the vessel 80. In FIGS. 4N and 5E, the filament perimeter 48 and distal opening 20 have moved even further proximally. The filament perimeter 48 has changed shapes from the predetermined shape 46 to an elongated loop due to the tension across the elements. In some embodiments, the distal opening 20 is generally concentric with the vessel 80 while in other embodiments the distal opening 20 may be of axis or angled in any manner determined by the applied forces.

The cross sectional area of the distal opening when it is in the closed configuration may be between 0-1.0 mm$^2$ or between 0.01-0.2 mm$^2$. The distal opening 20 must be mostly closed to prevent any parts of the clot 78 from coming out of the container element 4. The distal opening 20 is formed by the space between the looped ends 106 of the braided container element 4. In the closed configuration, the looped ends 106 are bunched up close together such that the effective distal opening perimeter 62 of the distal opening 20 is significantly reduced from the open shape. For example, if the device 2 is used in a cerebral artery application and deployed into a vessel with a 5 mm diameter, the circumference of the distal opening 20 when the container element 4 is deployed may be between 10 mm-20 mm or between 14 mm-17 mm. When the distal opening 20 is transitioned to a closed configuration, the circumference may be between 0.01 mm-5 mm or between 0.5 mm-2 mm. The distal opening perimeter 62 is now only occupied by part of the filament perimeter 48 which has been tensioned and so the majority of the filament perimeter 48 is now proximal to the distal opening 20. The shape of the distal opening 20 configuration in this shape is not necessarily circular and in fact is likely not circular. The shape may be like a horseshoe or half-moon or any portion of an arc or bent wire.

In FIG. 5E, the distal end 16 of the container element 4 is shown inverted such that it has move further proximally within the container element 4 itself. The tension in the filament 6 has pulled the distal end 16 proximally and secured the distal opening 20 closed.

In some embodiments the filaments 6 are connected to the constraining catheter 8 such that the constraining catheter 8 can be further retracted and the filaments 6 can close at the distal end 16. In such an embodiment, the user only needs to retract one component, in this case the constraining catheter 8, in order to deploy the container element 4 and then continue to retract it in order for the distal opening 20 to constrict. FIGS. 4J-4N show the constraining catheter 8 moving proximally as the filament 6 is placed in tension indicating such a configuration. This may provide advantages for the user interface and simplicity of the device 2. In some embodiments, the clot engagement element 58 or the intermediate catheter 72 may be connected similarly to the filament 6 to perform a similar function as described above. In other embodiments, a handpiece may exist outside of the body which handles the relative movements of the catheters and elements. For example, a syringe type motion or a trigger type motion by the user may cause the device 2 to go through its relative motions as described herein. In this manner the user does not have to think about which component to move but rather can just activate a simple interface to move through the various stages.

In FIG. 4O, the clot engagement element 58 has been removed from the body leaving the majority of the clot 78 behind in the container element 4. In some embodiments this step is not performed and the clot engagement element 58 can remain in position relatively to the container element 4 as the entire device 2 is removed from the body.

In FIG. 4P, the device 2 begins to be removed from the body by pulling it proximally. In the embodiment shown, the container element 4 is a braid that decreases in diameter as it is placed under tension. The container element 4 therefore stretches as shown and can be further pulled into other catheters if necessary. At this point the clot 78 is fully contained within the container element 4 and will not distally embolize as it is retracted. The container element 4 and device 2 may be stretched as much as necessary to remove it from the body. In some embodiments, once the filament 6 is pulled taut and the distal opening 20 of the container element 4 is constricted, it does not significantly open again even if the tension in the filament 6 is reduced or removed. This may be caused by a locking mechanism in the device 2 that locks the filament perimeter 48 closed or may be simply due to friction within the system that prevents the filament perimeter 48 from opening once it is closed. Alternatively, the distal opening 20 of the container element 4 may automatically open once the filament 6 is relaxed. In some embodiments, after the device 2 is removed from the body it may be opened and the device 2 may be used again for additional clots 78 and foreign bodies.

Figure 6A:
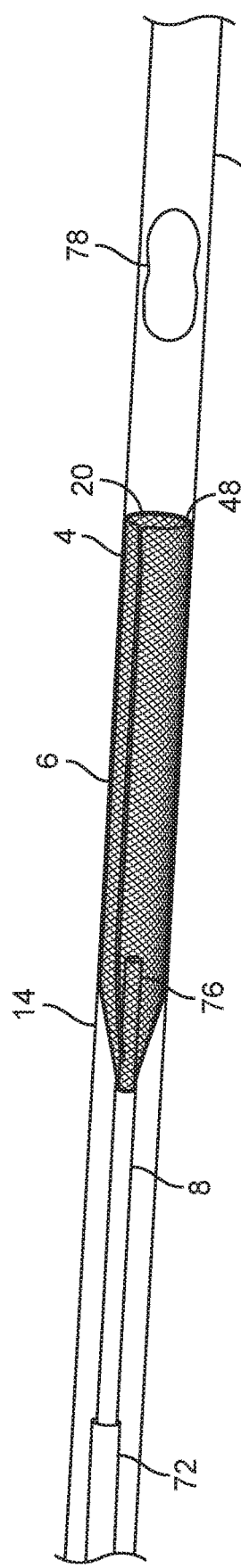
FIG. 6A illustrates an embodiment of the device with an aspiration catheter.

In FIGS. 6A-6H, an alternative embodiment of the device 2 is shown. In this embodiment, the clot engagement element 58 is an aspiration catheter 76 rather than a stent retriever. In FIG. 6A, the container element 4 has been deployed in the vessel but no microcatheter 74 or stent retriever necessarily traverse the clot. Instead, an aspiration catheter 76 exists within the lumen of the device 2 and may be advanced. The aspiration catheter 76 may be comprised of any of the materials or constructions known to one skilled in the art of catheters. The outer diameter may be on the order of 0.02″ to 0.080″ and sized to fit within the lumen of the container element 4. The aspiration catheter 76 may be connected to a vacuum source external or internal to the patient that provides suction to the distal end of the aspiration catheter 76. The aspiration catheter 76 can be used for aspirating blood such that it flows in a proximal or retrograde manner within the cerebral artery. Additionally, the suction in the aspiration catheter 76 can be used to engage and remove clots 78 or foreign bodies.

Figure 6B:
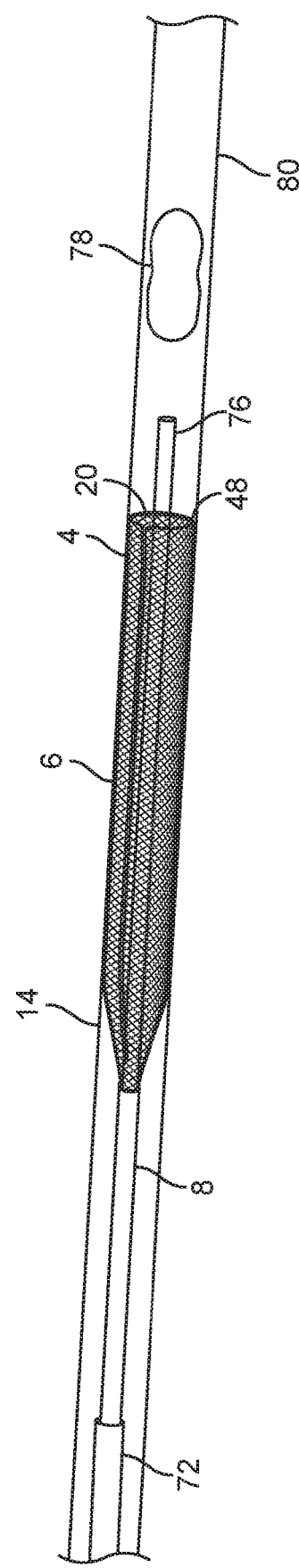
FIG. 6B illustrates the aspiration catheter advanced toward the clot.
Figure 6C:
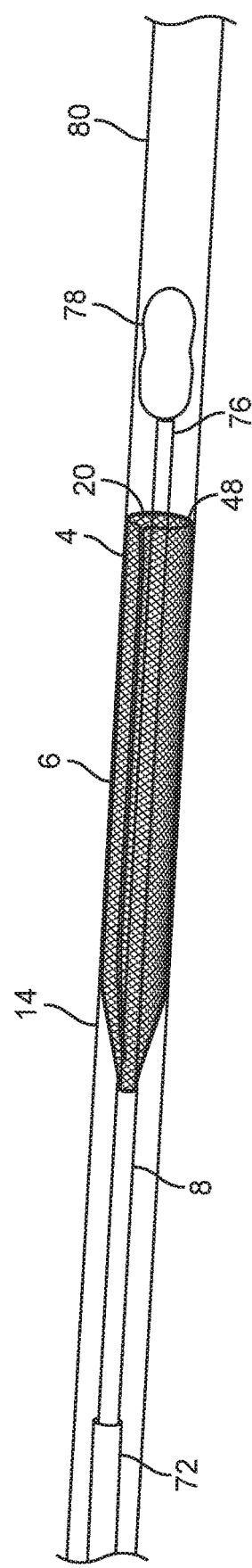
FIG. 6C illustrates the clot drawn toward the aspiration catheter.

In FIG. 6B, the aspiration catheter 76 is advanced distally toward the clot 78. In FIG. 6C, suction applied to the clot 78 may pull the clot 78 toward the aspiration catheter 76 or alternatively the aspiration catheter 76 may be advanced all the way to the clot 78 before suction is applied. In FIG. 6D, the aspiration catheter 76 is withdrawn into the container element 4 with the clot 78 such that the clot 78 is contained within the container element 4. In some embodiments, the clot 78 may be in multiple pieces or may break apart during the aspiration and retraction. In such cases, the aspiration catheter 76 may be extended distally multiple times from the container element 4 and engage with new pieces of clot 78. The clot 78 can be retracted into the container element 4 and can then be dislodge from the aspiration catheter 76 by releasing the suction or providing a positive pressure through the aspiration catheter 76 to dislodge the clot 78. Alternatively, the distal opening 20 of the container element 4 can be partially closed as described herein and used as a method of keeping the clot 78 within the container element 4 while allowing the aspiration catheter 76 to be distally extended again to engage with another piece of clot 78.

In FIG. 6E, the filament 6 is tensioned and the distal opening 20 begins to close and may retract proximally. In FIG. 6F, the filament 6 is further tensioned and the distal opening 20 closes further. In this state, the aspiration catheter 76 could be advanced distally to extend out of the container element 4 and engage with another clot 76. In such embodiments, a guidewire or microcatheter 74 may be left distal to the distal opening 20 so that the aspiration catheter 76 can traverse through the distal opening 20. Before pulling the new clot 78 into the container element 4, the distal opening 20 may be opened as needed by releasing tension on the filament 6. Aspiration may be applied through the container element 4 to keep any loose clot fragments within the container element 4 while the distal opening 20 is partially or fully open. In FIG. 6G, the distal opening 20 is inverted within the container element 4. In FIG. 6H, the distal opening 20 is further inverted and moved proximally along with the filament perimeter 48.

In some embodiments, a separate aspiration catheter 76 is not necessary. The aspiration can be applied to the lumen of the container element 4 such that flow is directed in from the distal opening 20. The container element 4 can be positioned just proximal to the clot 78 so that when aspiration is applied, the clot 78 is suctioned into the container element 4. In any of the embodiments described herein aspiration may be applied to any of the elements. For example, a vacuum source may be fluidly connected to the constraining catheter 8, container element 4, microcatheter 74, aspiration catheter, intermediate catheter 72, or any other component.

Figure 7A:
FIG. 7A illustrates a constraining catheter.
Figure 7B:
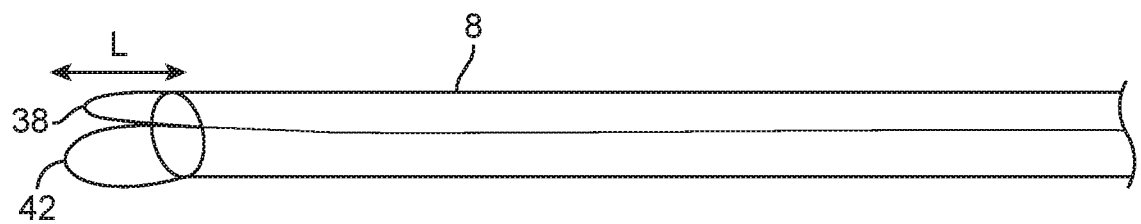
FIG. 7B illustrates a filament advancing out of the constraining catheter.
Figure 7C:
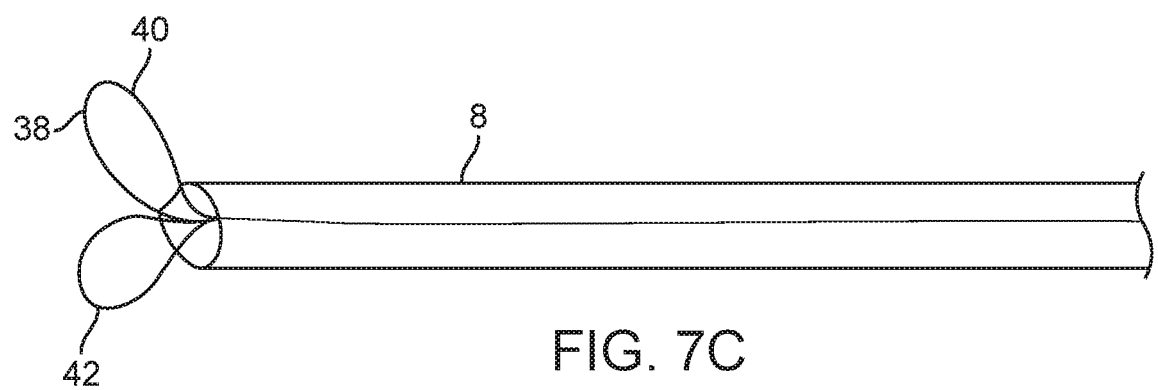
FIG. 7C illustrates the filament further advanced out of the constraining catheter.
Figure 7D:
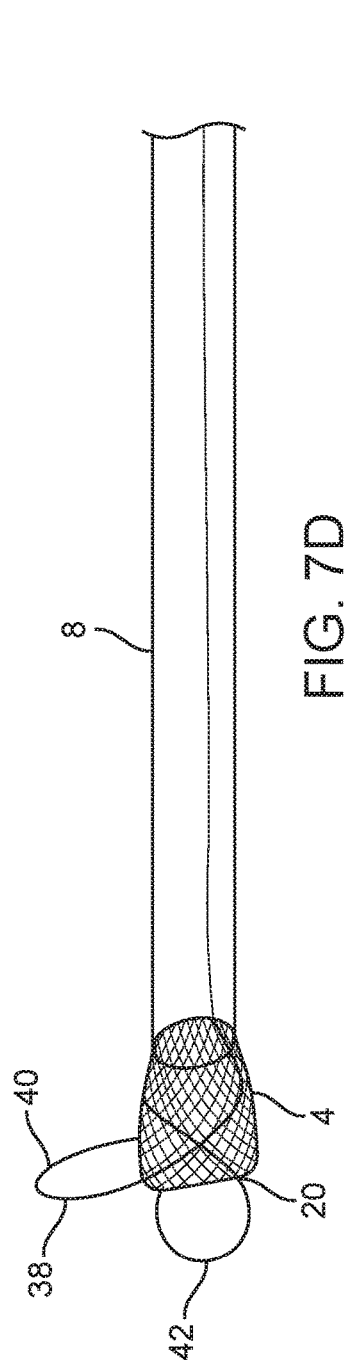
FIG. 7D illustrates a container element advancing out of the constraining element.
Figure 7E:
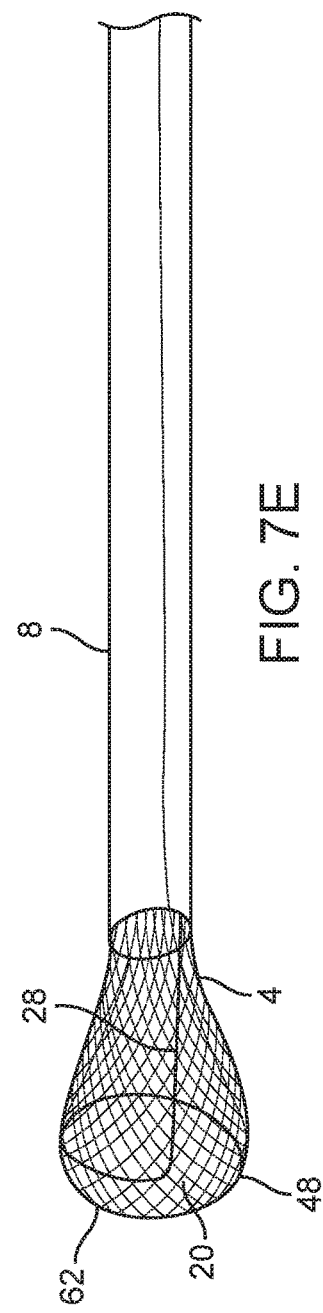
FIG. 7E illustrates the filament forming an open distal end of the container element.
Figure 7F:
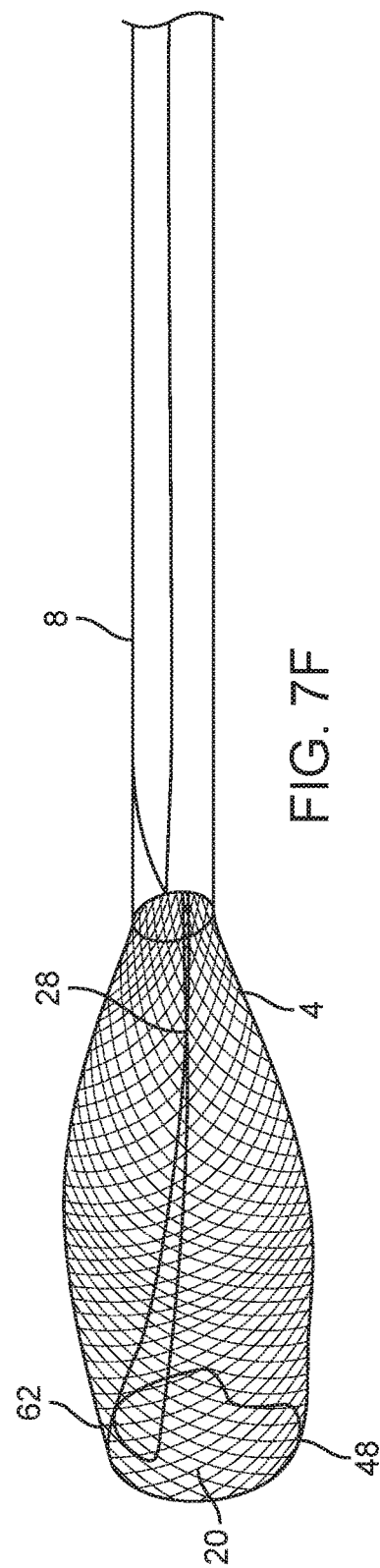
FIG. 7F illustrates the container element further advanced out of the constraining element.

Turning now to FIG. 7A-7G, an embodiment of the device 2 is shown with the container element 4 deploying out of a constraining catheter 8 in greater detail. In FIG. 7A, a constraining catheter 8 is shown with a distal end. As mentioned, the constraining catheter 8 may be a separate catheter or may be an intermediate catheter 72 or any other catheter within the device 2. In FIG. 7B, the container element 4 begins to deploy. A first leading portion 38 of the filament(s) 6 begins to exit the constraining catheter 8 as shown in a 'bunny ears' configuration. The term bunny ears is intended to describe the shape shown in FIG. 7B-7D, however this term should not be limiting to other shapes or configurations which may accomplish the same thing. In FIG. 7C, the first leading portion 38 of the filament 6 exit the constraining catheter 8 more and begin to fold outward. The first leading portion 38 forms a first loop 40 that resembles a bunny ear. A second leading portion 42 may also exist and move with the first leading portion 38. In FIG. 7D, the braid of the container element 4 begins to deploy as shown. As the distal end 16 of the container element 4 begins to open slightly, the length of the filament 6 within the first loop 40 begins to become the filament perimeter 48 at the distal end. In FIG. 7E, the container element 4 is further deployed and the distal end has opened up substantially from its constrained shape within the constraining catheter 8. At this point, most of the length of the filaments 6 that was previously within the 'bunny ears' shape has become the filament perimeter 48 of wire at the distal end 16 of the container element 4. There is no significant excess filament 6 length at the distal end 16 of the container element 4 and the distal end 16 of the container element 4 has been deployed in a primarily open configuration, not a constricted configuration. In FIG. 7F, the container element 4 is further deployed.

Figure 7G:
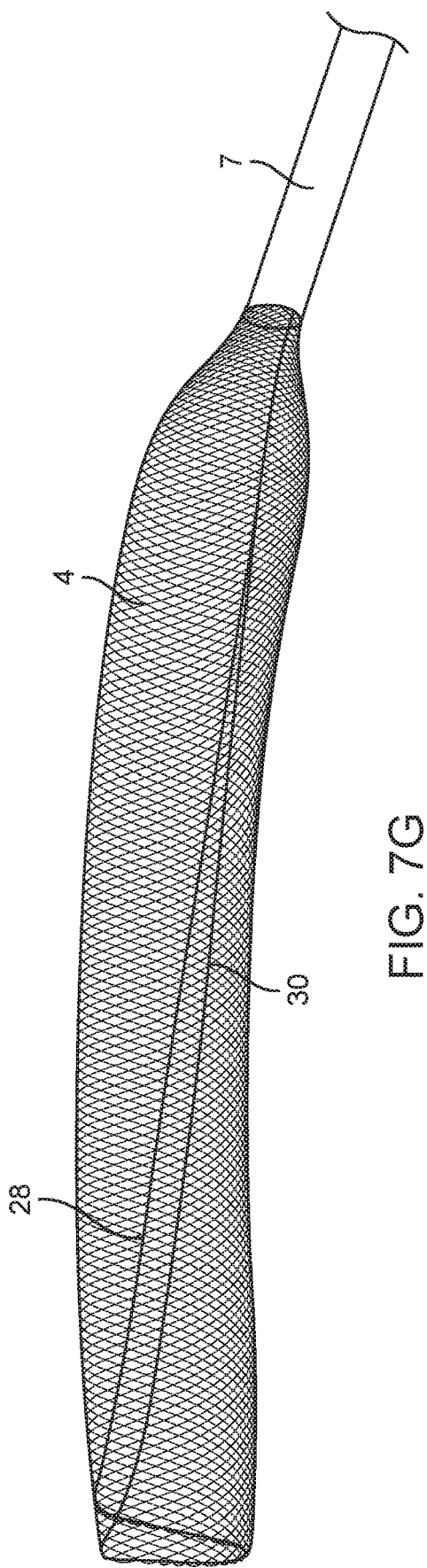
FIG. 7G illustrates the container element further advanced out of the constraining element.

In FIG. 7G the container element 4 is mostly deployed. The filament perimeter 48 at the distal end 16 of the container element 4 is in the open configuration and the arms 28, 30 run on the inside surface of the container element 4 and into the constraining catheter 8. At this point, the clot engagement element 58 could be pulled into the container element 4 at the distal end 16.

The 'bunny ears' shape of the filaments may be important because it is one embodiment in which the container element 4 may be deployed with an open distal end 16. As used herein, 'bunny ears' refers to a specific aspect of the leading portion 38 and all combinations and features shall be shared without indispensable features from either. That is, all features of the 'bunny ears' needn't include a closed loop 50 nor more than one for those features to be used with any aspect of the leading portion 38 independently. Stated another way, the terms may be interchangeable without impugning any necessity of one or the other or any feature of one to the other by necessity. When the container element 4 is within the constraining catheter 8, the distal opening 20 is much smaller than when it is open after being deployed. For example, when it is within the constraining catheter 8, the distal opening 20 may be 1.0 mm in diameter versus when it is deployed and open it may be 5.0 mm in diameter. In this example, this represents a 5× increase in diameter and circumference. Therefore, since the filament perimeter 48 extends around the circumference of the container element 4, the length of the filament 6 at the distal end 16 has to similarly increase by 5×. In some embodiments, the filament 6 at the distal end 16 can simply grow in length by pulling more filament 6 distally. However, the force required to pull more filament 6 distally may be significant compared to the opening force of the container element 4. For example, if the container element 4 is a shape set braid that has a nominal 5 mm diameter then it will have a given radial force trying to open the distal end once it is deployed from a 1 mm constraining catheter 8. However, this force may not be enough to pull more filament 6 distally especially if the device 2 is long or curved due to anatomical constraints. Therefore, the distal end 16 may not open fully when it is deployed unless another consideration is given for the increase in filament 6 length at the distal end. The 'bunny ears' keep an amount of excess filament length at the distal end 16 of the container element 4. Therefore, when the container element 4 is deployed, the filament perimeter 48 at the distal end 16 can form an open circular shape. This is particularly relevant in embodiments where the filament 6 is shape set to a predetermined shape 46 such as a circle. The 90 degree filament bend 54 where the filament 6 transitions from the filament perimeter 48 to the arms 28, 30 going back along the longitudinal length of the device 2 does not move substantially relative to the container element 4 when the device 2 is deployed versus when it is constrained. The length of the filament perimeter 48 instead transforms into the 'bunny ears' shape and is then constrained by the constraining catheter 8 with leading portions 38 extending distally from the end of the container element 4. In some embodiments the shape set profile of the filament 6 perimeter can include features which encourage the 'bunny ears' shape or a similar shape. For example, the filament perimeter 48 may be primarily a circle but may additionally have small nipples 102 extending radially outward defined by the loop pathway as shown in FIGS. 2F and 2G. This may provide a specific place for the 'bunny ears' to bend when they are constrained within the constraining catheter 8. Though FIGS. 7A-7G show a 'bunny ears' shape, any number of other shapes may be contemplated such as a single loop, several loops, or any other shape that takes up the filament length when it is constrained.

In other embodiments, the excess amount of filament 6 length is folded or bunched up in any number of other locations. In FIGS. 14A-14C, an embodiment of such a device 2 is shown. In FIG. 14A, a container element 4 is shown in a constrained configuration. Although a constraining catheter 8 is not shown, it can be appreciated that the container element 4 is radially constrained within a catheter. As shown the distal opening 20 of the container element 4 is relatively small. There is a filament 6 with a filament junction 100 as also described in FIGS. 2I and 2J, such that there is a single arm 28 extending proximally from the filament perimeter 48. The filament perimeter 48 has a generally circular predetermined shape 46 when unconstrained but in the constrained configuration shown the filament perimeter 48 has an elongated loop shape. The filament perimeter 48 extends along a given length of the longitudinal axis LA of the container element 4 that is roughly one half of the circumference of the filament perimeter 48 when it is unconstrained. For example, if the diameter of the filament perimeter 48 is 5 mm, the longitudinal length of the filament perimeter 48 when stretched as shown may be about 6 mm-9 mm. The distal arm 98 transitions to a region of filament excess length 96 which is folded into the constraining catheter 8 and then transitions to a filament proximal arm 94. As will be shown, the filament excess length 96 is folded and stored within the constraining catheter 8 so that when the filament perimeter 48 expands to its unconstrained shape, the filament excess length 96 can be utilized. In FIG. 2B, the container element 4 and filament perimeter 48 have been deployed out of the constraining catheter 8. The filament perimeter 48 now extends a very short length of the longitudinal axis LA of the container element 4. For example, the filament perimeter 48 may extend only about 0 mm-3 mm or 0.25 mm-1 mm. As a result, the filament junction 100 advances distally by about the difference between the longitudinal length of the filament perimeter 48 in the constrained shape and the longitudinal length of the filament 6 in the deployed shape. For example, this might be about 1 mm-9 mm or 3 mm-6 mm. The filament excess length 96 may then unfold and allows the extension of the filament distal arm 98 without substantial movement of the filament proximal arm 94. The folded filament excess length 96 enables the frictional force of pulling the filament distal arm 98 to be minimized since the filament proximal arm 94, which extends through additional components and potentially tight turns, does not need to move substantially. Therefore, the radial opening forces of the filament 6 or the container element 4, or both, do not need to overcome a large frictional force and may still achieve their open deployed position. The folded filament excess length 96 may exist at any location within any of the catheters but may be optimally applied within the container element 4 and more optimally toward the distal end 16 of the container element 4 and as explained elsewhere herein. The features related to the working length WL may be combined in any subset of features as being related aspects of the invention and all such combinations and sub-combinations are expressly provided as further aspects of the present invention. For example, it is expressly provided even though not explicitly stated that the folded filament 6 is positioned within 10 mm of the distal end so that all features describe above concerning the working length are equally applicable to the folded filament 6. As another example, FIG. 14 shows that the excess length may be along the distal portion and formed by a first fold and a second fold forming a flat z-shaped portion for the filament excess length 96. In FIG. 14C, the device 2 is shown in a closed configuration as the proximal arm 28 is placed in tension. The filament excess length 96 may unbend more than is shown in the figure, but it should be noted that the shape of the filament 6 in the closed configuration is unique and different from the shape of the filament 6 in the constrained position.

In some embodiments, the filament perimeter 48 shape when the container element 4 is in the constraining catheter 8 is different than the shape of the filament perimeter 48 when the distal opening 20 is closed. The filament perimeter 48 therefore goes through at least 3 unique shapes. First, when the container element 4 is in the constraining catheter 8, the filament perimeter 48 is in a shape that may look like the 'bunny ears' or any other shape where the filament excess length 96 is accounted for. This includes the askew plane configuration described in greater detail below. Second, when the container element 4 is in the open deployed configuration, the filament perimeter 48 forms a circumference of the distal opening 20 that is generally circular. The filament perimeter 48 may be at or close to its predetermined shape 46 at this point. Third, when the filament 6 is in tension and the distal opening 20 is closed, the filament perimeter 48 resembles an elongated loop or stretched rubber band where the distal end of the filament perimeter 48 forms a small circumference of the distal opening 20 which may or may not be circular. The filament perimeter 48 transitions between these three shapes during the normal use of the device 2. Specifically, the first and third shapes are unique meaning that the shape of the filament perimeter 48 when the container element 4 is in the constraining catheter 8 is not necessarily the same as when the distal opening 20 is closed.

Figure 8A:
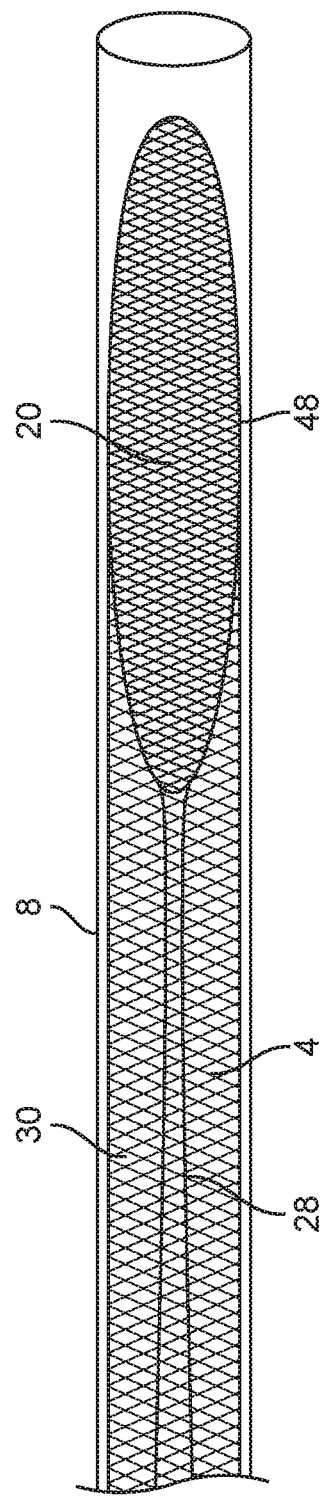
FIG. 8A illustrates an embodiment with an askew plane filament perimeter in a constraining catheter.
Figure 8B:
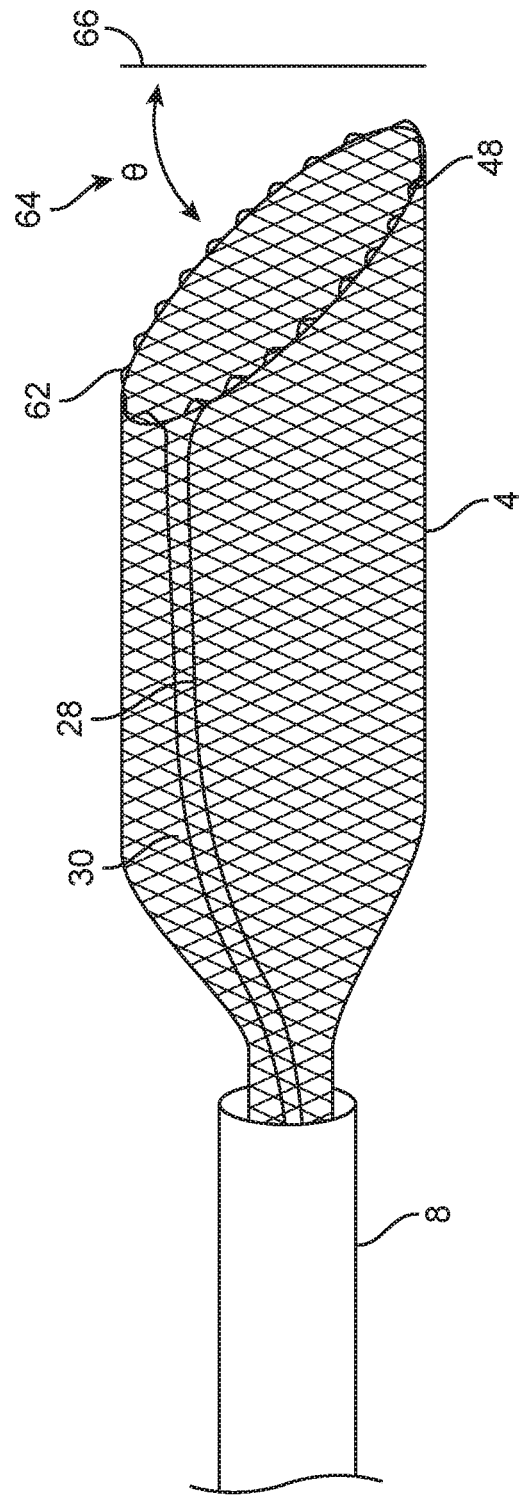
FIG. 8B illustrates an embodiment with an askew plane filament perimeter deployed from a constraining catheter.

In FIGS. 8A and 8B, another embodiment which accounts for the diameter change is shown. In some embodiments other designs which address the filament length issue may be utilized. The filament perimeter 48 generally forms a plane. The plane may be a perpendicular plane 66 which is perpendicular to the longitudinal axis LA of the container element 4 as shown in FIGS. 4A-4P, or the plane may be askew to the longitudinal axis LA. In FIG. 8B, the plane is tilted by an askew angle 64 of about 30 degrees from the perpendicular plan 66. The filament perimeter 48 forms an ellipse or similar shape and has a distal section at one apogee and a proximal section at the other apogee. An advantage to this design is that when the container element 4 is constrained within the constraining catheter 8, as shown in FIG. 8A, it increases in length. Therefore, if the filament perimeter 48 is askew, it will increase in length as it is constrained radially and the amount that it is askew will increase. So the filament excess length 96 is transformed from a larger diameter when it is deployed to a longer length when it is constrained. This addresses the same problem identified above such that the filaments 6 do not need to move distally so that the distal end 16 of the container element 4 can open once it is deployed. The excess filament length needed to change from a constrained shape to a deployed shape is already in place at the distal end and the arms 28, 30 do not need to be pulled distally a substantial amount. Additionally, having an askew distal end opening may provide advantages for guiding the clot engaging element 58 into the container element 4. In some embodiments the distal end 16 of the container element 4 with its crown of looped ends is also askew to its longitudinal axis LA while in other embodiments the filament perimeter 48 is simply threaded through the braid of the container element 4 at an angle while the distal end is still perpendicular to the longitudinal axis LA. The amount that the snare is askew to the perpendicular plane 66 may be between 2-60 degrees or between 10-30 degrees. When the embodiment shown in FIGS. 8A and 8B is in the closed configuration by placing tension on one or both of the arms 28, 30, the closed shape may look similar to other embodiments shown and described herein. Meaning, the shape of the filament perimeter 48 in the closed configuration is not necessarily the same as the shape of the filament perimeter 48 in the constrained configuration.

In some embodiments, the filament perimeter 48 does not define a single plane and instead may be a more complex three-dimensional shape. For example, the filament perimeter 48 may have portions that are askew to the longitudinal axis LA of the container element 4 and other portions that are askew in a different angle or orientation. The filament perimeter 48 may have protrusions that extend proximally or distally. The filament perimeter 48 is not constrained by a single plane.

Figure 9B:
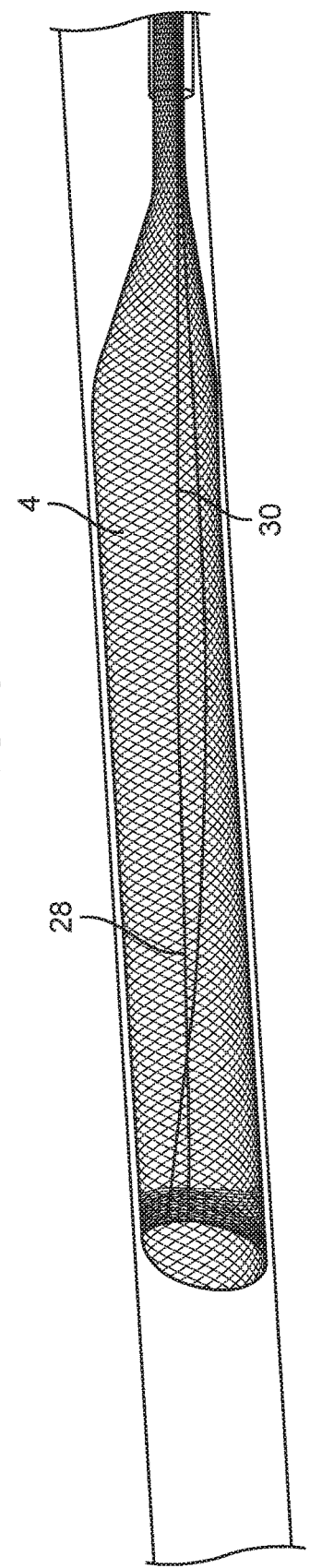
FIG. 9B illustrates the distal end of the container element partially closed and retracted.
Figure 9C:
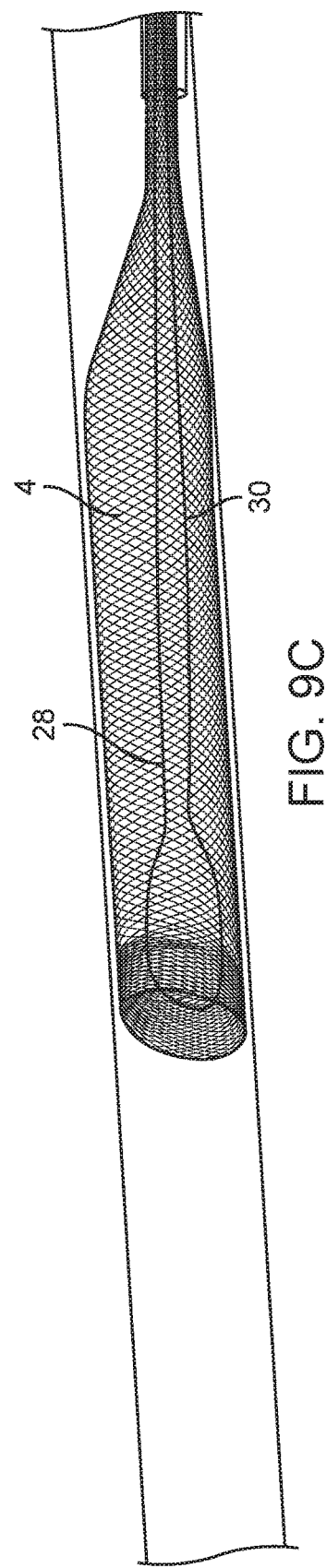
FIG. 9C illustrates the distal end of the container element further closed and retracted.

In FIGS. 9A-9F, the closure of the distal opening 20 of the container element 4 is shown in greater detail. The container element 4 is within a 5 mm vessel. In these figures, the clot 78 and clot engagement elements 58 are not shown but would be within the container element 4 during this step. In FIG. 9A, the distal end 16 of the container element 4 is generally open such that it could receive the clot engagement element 58 to be pulled into the container element 4. The filament perimeter 48 is in an open shape and there may be little or no tension in the arms 28, 30. Once the clot 78 and clot engagement elements 58 are within the container element 4, tension can be placed on the arms 28, 30 as shown in FIG. 9B which moves the distal end 16 of the container element 4 proximally as the braid bunches up and expands radially. The distal opening 20 of the container element 4 effectively closes as the filament 6 is pulled proximally. As can be seen in FIG. 9C, the shape set profile of the circular filament perimeter 48 is retracted further and stretched so that only a small amount of the filament perimeter 48 remains at the distal opening 20 as it is closed and the distal opening perimeter 62 is significantly reduced.

In FIG. 9D, the filaments arms 28, 30 are pulled further proximally and the distal opening 20 of the container element 4 moves proximally as well and even folds back within itself. In FIG. 9E, the distal end 16 is folded back even further. This may be required in some embodiments while in other embodiments less tension is required on the arms 28, 30. A critical aspect is that the clot 78 particles do not escape the container element 4.

In FIG. 9F, the container element 4 is shown removed from a vessel 80 with the distal end constricted. As can be seen there is generally no opening at the distal opening to allow further embolization of the clot 78. The filament 6 is effectively closing the distal opening 20 as a purse string so that all the looped ends 106 of the braid are close together.

In other embodiments, a filament catheter 82 is included in the device 2. A filament catheter 82 can provide several advantages. First, it can provide axial support to the device 2 as the filament 6 is being cinched. The support may hold the distal end 16 of the device 2 in a fixed position during the distal opening 20 closure. Second, it can facilitate in the deployment and retraction of the container element 4 in the vessel. In the configurations where the container element 4 is a braid, the filament 6 catheter can be used to stretch the braid and thereby reduce its diameter by applying a distally acting tension on the braid. Third, it can keep the arms 28, 30 constrained as they are inside or outside of the container element 4.

Figure 10A:
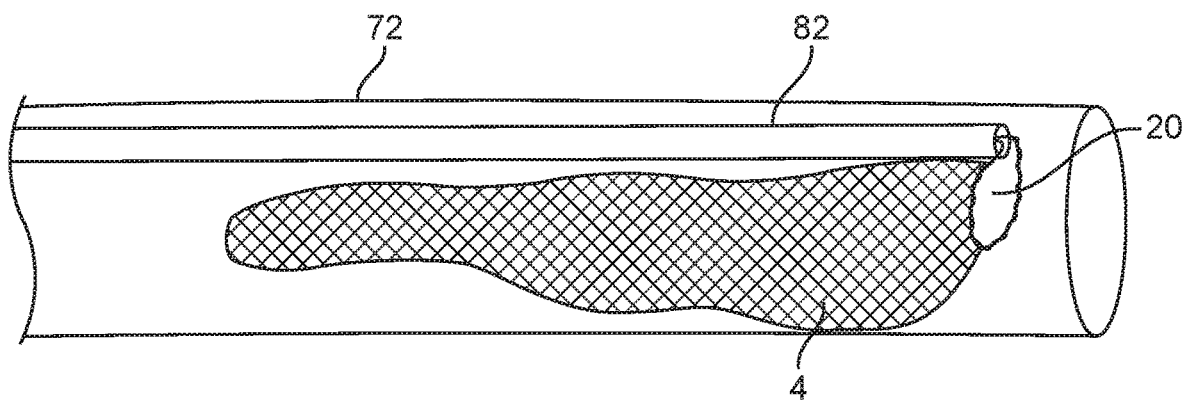
FIG. 10A illustrates an embodiment of the container element inside an intermediate catheter.
Figure 10B:
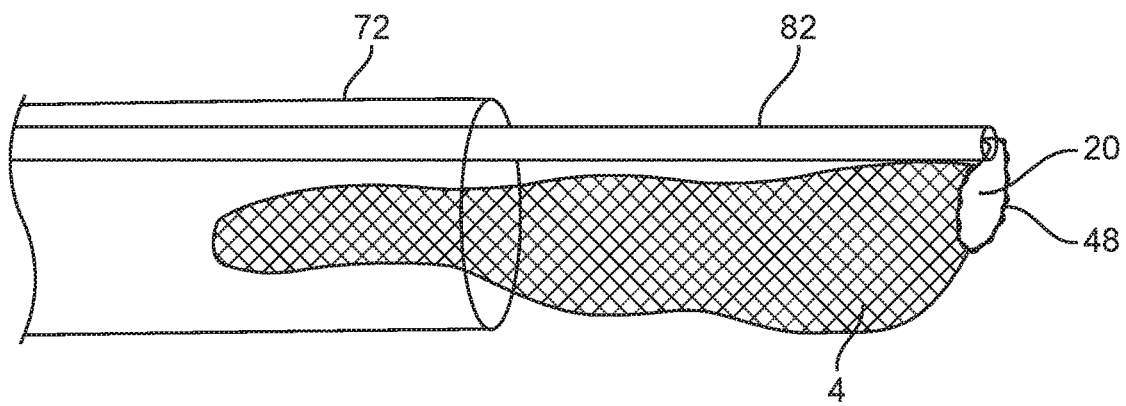
FIG. 10B illustrates the container element with the intermediate catheter retracted and the distal opening closed.
Figure 10C:
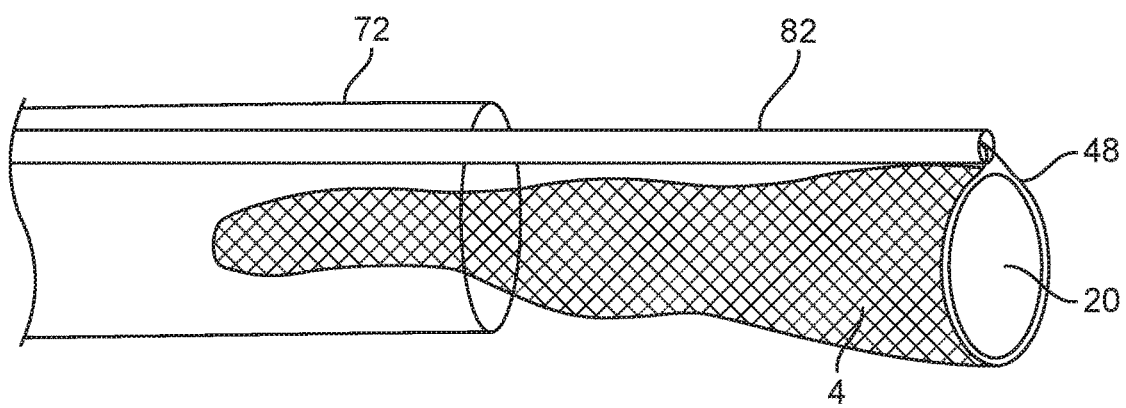
FIG. 10C illustrates the container element with the intermediate catheter retracted and the distal opening open.

FIG. 10A shows the filament catheter 82 within the intermediate catheter 72 and the distal opening 20 in the closed configuration. The container element 4 is completely within the intermediate catheter 72 in this configuration and the intermediate catheter 72 can be advanced to the target vessel 80 in this configuration. In this embodiment, the filament catheter 82 is shown external to the container element 4. Alternatively, the filament catheter 82 could be within the lumen of the container element 4. In FIG. 10B, the intermediate catheter 72 has been retracted while the filament catheter 82 remained in the same location. Alternatively, the filament catheter 82 can be advanced while the intermediate catheter 72 remains in the same location. The filament perimeter 48 is distal to the end of the intermediate catheter 72 and is still in the closed configuration with the proximal end of the container element 4 still within the intermediate catheter 72. It should be noted that the amount of closure of the distal opening 20 can be less or more than what is shown. For example, the distal opening 20 can be closed more so that the container element 4 at the filament perimeter 48 touches itself and forms a full or partial seal at the distal opening 20. In FIG. 10C, the filament 6 has been advanced and the distal opening 20 is in the open configuration. The filament perimeter 48 is opened to approximately the size of the vessel diameter and the container is therefore opened as well.

Figure 11A:
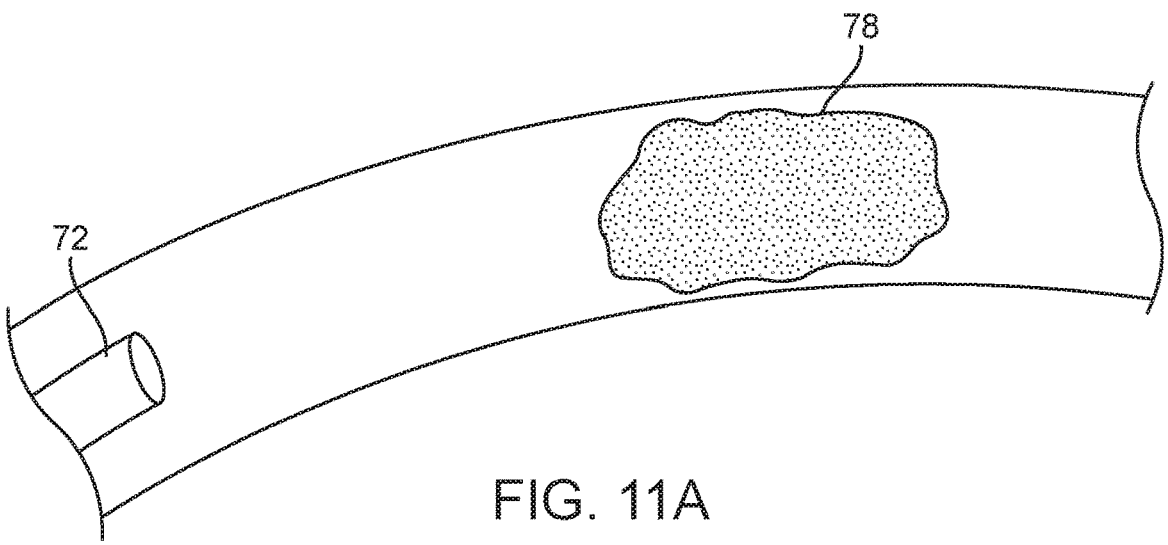
FIG. 11A illustrates a vessel with a clot and an intermediate catheter inside the vessel.
Figure 11B:
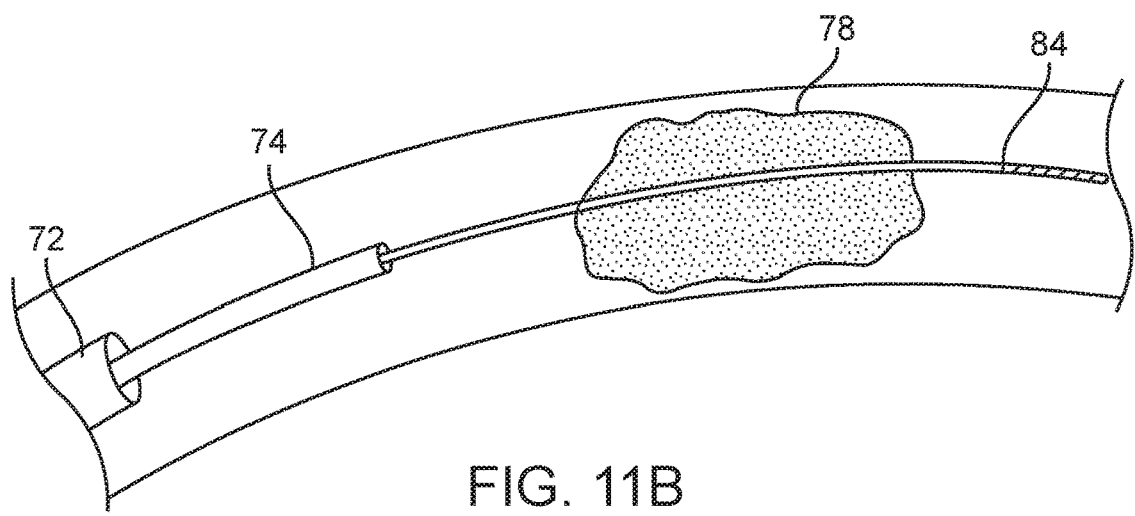
FIG. 11B illustrates a microcatheter extending from the intermediate catheter and a guidewire traversing the clot.
Figure 11C:
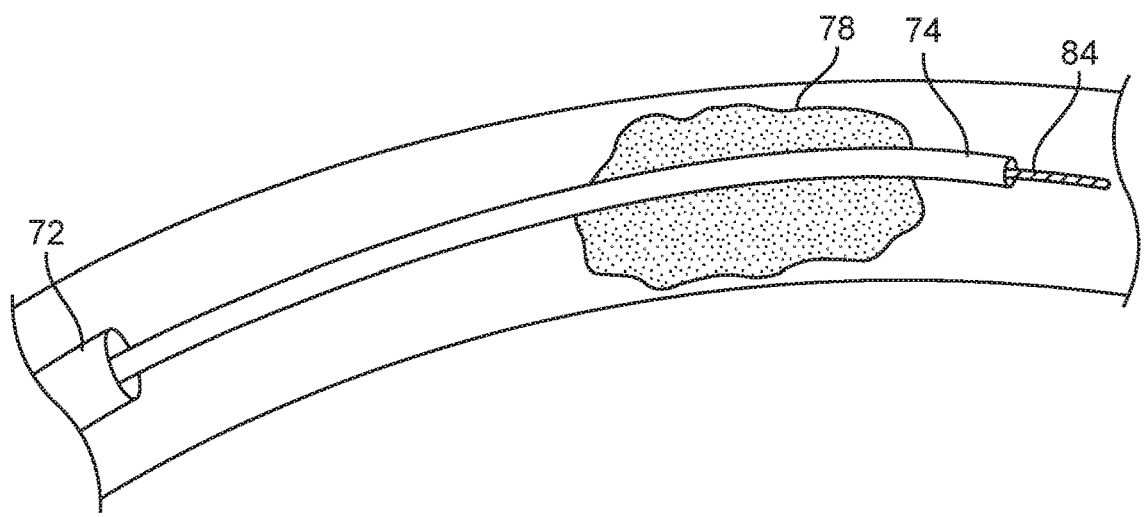
FIG. 11C illustrates the microcatheter traversing the clot.
Figure 11D:
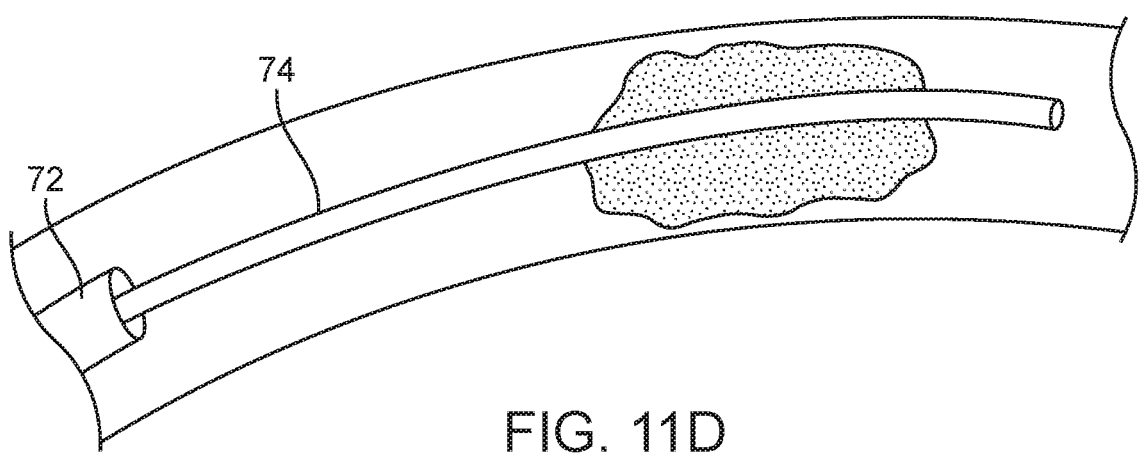
FIG. 11D illustrates the guidewire removed from the patient.
Figure 11E:
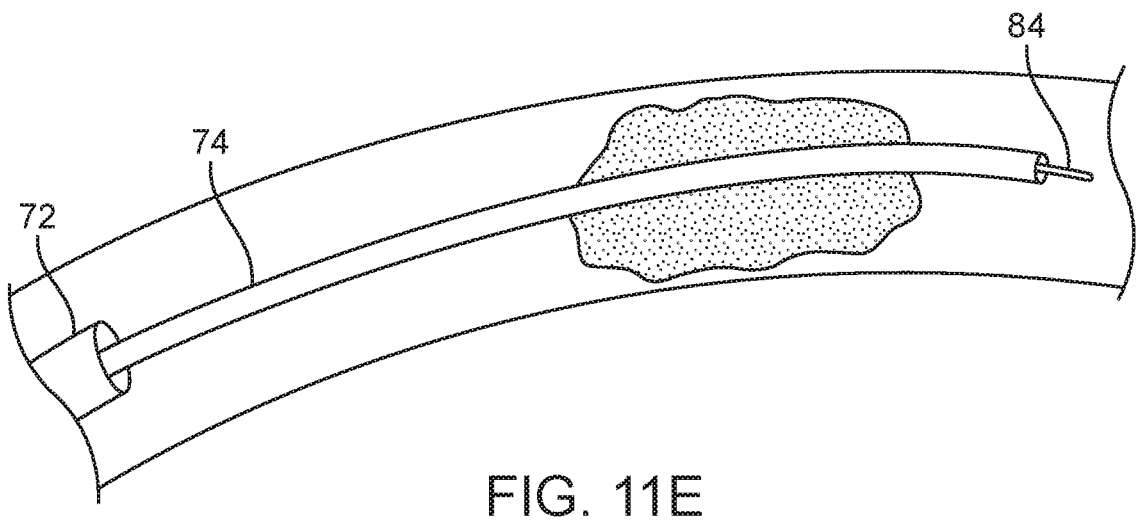
FIG. 11E illustrates a stent retriever inserted into the microcatheter and traversing the clot.
Figure 11F:
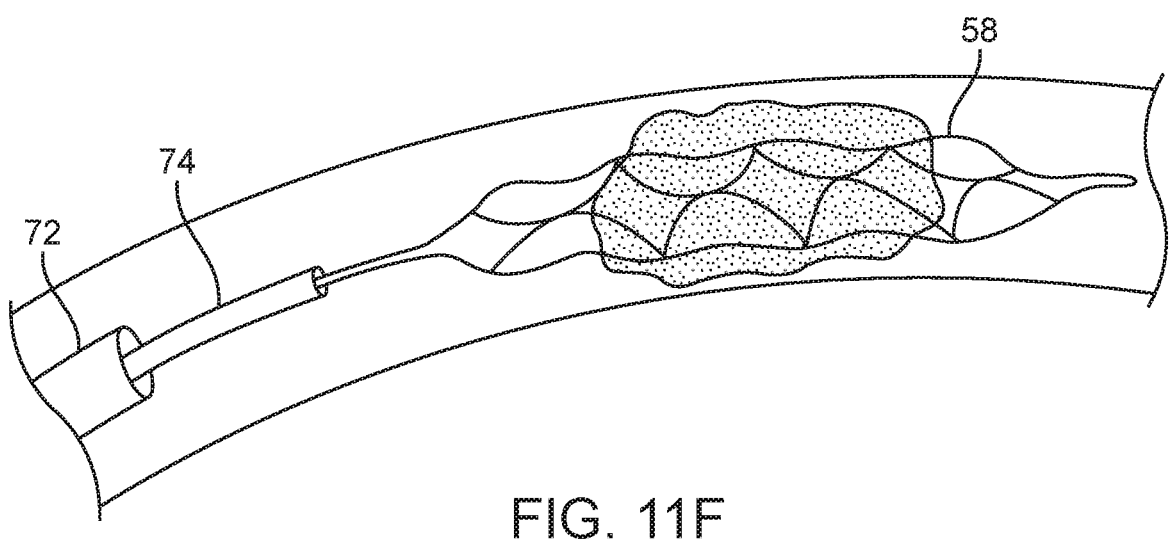
FIG. 11F illustrates the microcatheter retracted and the stent retriever capturing the clot.

Turning now to FIG. 11A-11K, the use of the invented device 2 and method will be shown. FIGS. 11A-11F show a series of steps that is similar to what may be currently practiced in thrombectomy procedures. In FIG. 11A, a clot 78 is shown in a vessel 80 such as a middle cerebral artery. An intermediate catheter 72 has been advanced to the target vessel 80 as shown. In FIG. 11B, a microcatheter 74 has been advanced and a guidewire 84 has been advanced so that it traverses the clot 78. In FIG. 11C, the microcatheter 74 follows the guidewire 84 and traverses the clot 78. Contrast may be injected through the microcatheter 74 at these steps to confirm its location with fluoroscopy. The guidewire 84 is removed from the microcatheter 74 in FIG. 11D. In FIG. 11E, a clot engagement element 58 such as a stent retriever is inserted into the microcatheter 74 until its tip extends distally from the end of the microcatheter 74. In FIG. 11F, the microcatheter 74 is retracted and the stent retriever expands into the clot 78 and grabs it so that it can be pulled with the stent retriever. In a typical thrombectomy procedure the stent retriever is now pulled along with the microcatheter and intermediate catheter 72. They can be pulled through the vessel and into a silicon balloon catheter in the carotid. While this can remove the clot it can also create fragmentation and distal embolization of the clot as described above.

FIGS. 11G-11K show the use of an embodiment of part of the invented device 2 and method which can reduce the problems associated with just pulling the clot engagement element 58 and bare non-covered clot 78 out through the vessel 80.

Figure 11G:
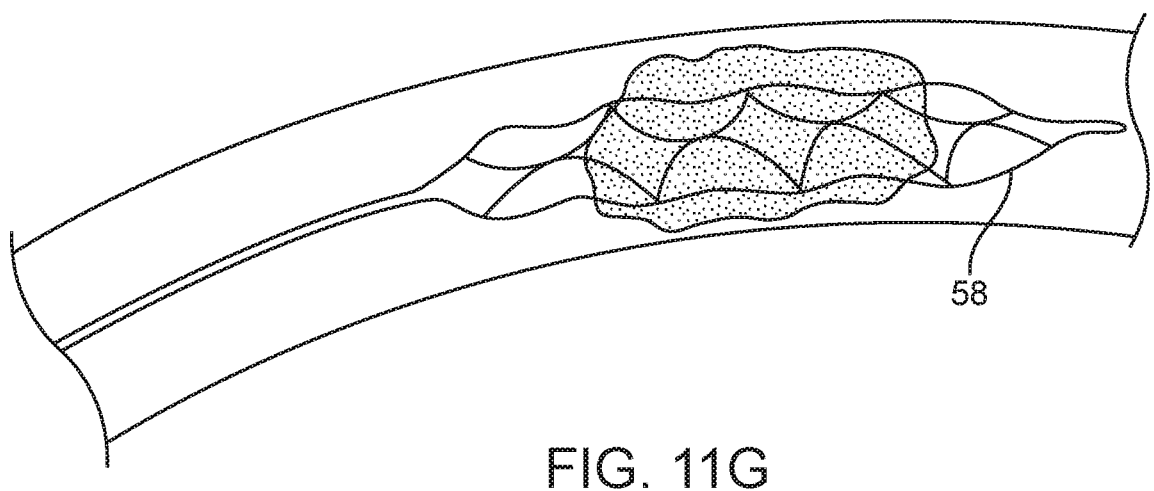
FIG. 11G illustrates the intermediate catheter and microcatheter removed from the patient.

In FIG. 11G, the intermediate catheter 72 and microcatheter 74 are removed, leaving the stent retriever behind in the vessel 80 with the clot 78. Monorail type catheters (e.g. Rapid Exchange) may be used instead of over-the-wire catheters for any of the catheters described herein to make exchanges of the catheters and wires easier. Alternatively, the intermediate catheter 72 can be left in place proximal to the clot 78 and the stent retriever. In this embodiment the device 2 can be fed into the existing intermediate catheter 72 and the remaining steps of the described procedure can be followed.

Figure 11H:
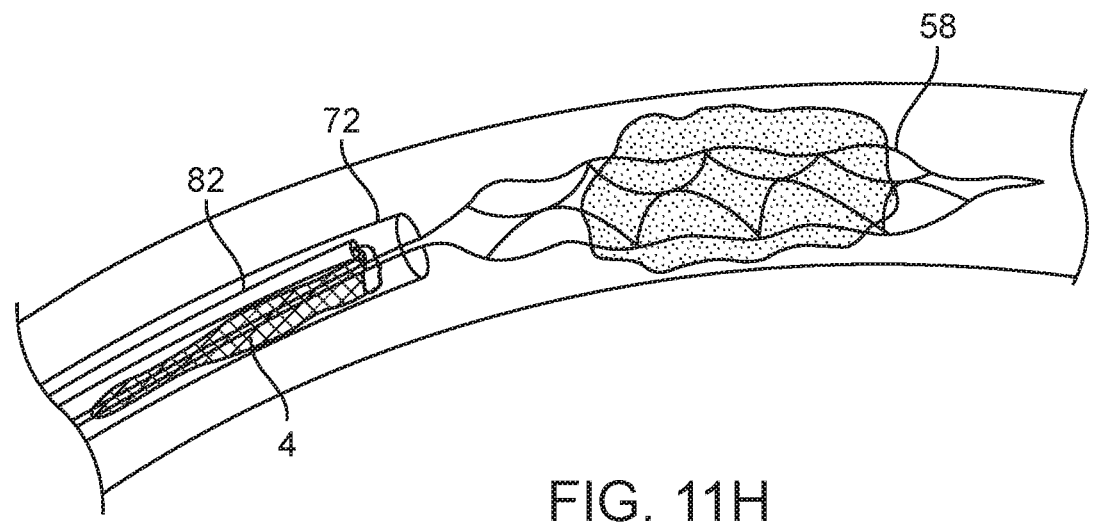
FIG. 11H illustrates an intermediate catheter inserted into the vessel with the container element inside the intermediate catheter.

In FIG. 11H, a new intermediate catheter 72 or the pre-existing intermediate catheter 72 with the device 2 is inserted onto the stent retriever wire and advanced to the target vessel. As described a monorail style catheter may be used. In at least some embodiments, the stent retriever wire is inserted through a hole at the proximal end of the container element such that the wire extends through the lumen of the container element 4. In other embodiments the hole may be significantly larger such that the container element 4 does not come to a closed end like a wind sock. The filament 6 is within the intermediate catheter 72 and is in the closed configuration.

Figure 11I:
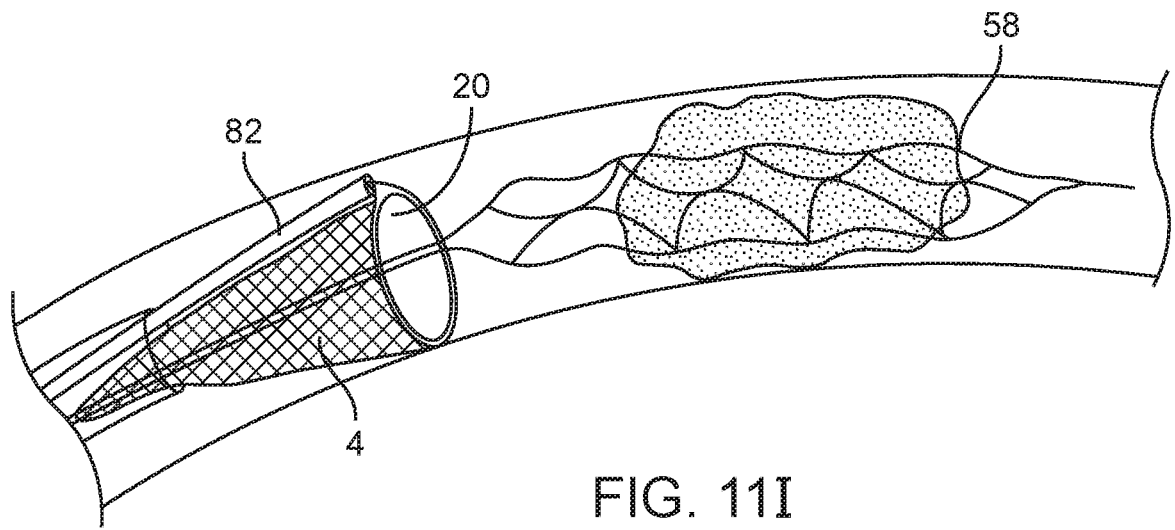
FIG. 11I illustrates the intermediate catheter retracted and the container element in an open configuration inside the vessel.

In FIG. 11I, the intermediate catheter 72 is retracted and the container element 4 is opened in the vessel 80. The filament perimeter 48 expands manually or automatically such that it approximates the vessel 80 inner diameter. In some embodiments, the container element 4 or filament 6 significantly reduces or occludes blood flow through the vessel to further prevent distal embolization of the clot. The full or partial occlusion of the vessel may additionally prevent the need for aspiration or a silicone balloon catheter in the carotid artery. In other embodiments, the container element 4 may only slightly limit the blood flow. The filament perimeter 48 and distal opening 20 may open more or less than is shown. For example, the filament perimeter 48 can be opened to provide a positive radial force on the vessel 80 and further ensure flow arrest.

Figure 11J:
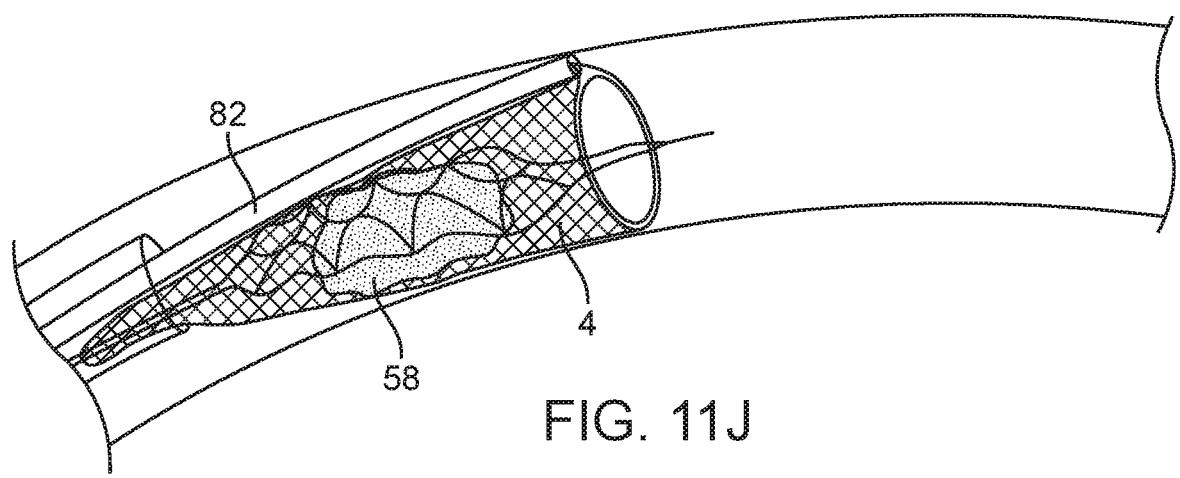
FIG. 11J illustrates the stent retriever and clot pulled within the container element.

In FIG. 11J, the stent retriever and clot 78 are pulled through the distal opening 20 and into the container element 4. Since the filament perimeter 48 may approximate the diameter of the target vessel 80, it acts like a funnel that the stent retriever and clot 78 are pulled into. The clot 78 is fully within the container element 4. In some embodiments, the container element 4 is connected to the filament catheter 82 along some portion of its length. For example, the proximal end of the container element 4 may be connected to the filament catheter 82 so it is not free floating. Alternatively, the entire length of the container element 4 may be connected or integrated into the filament catheter 82.

Figure 11K:
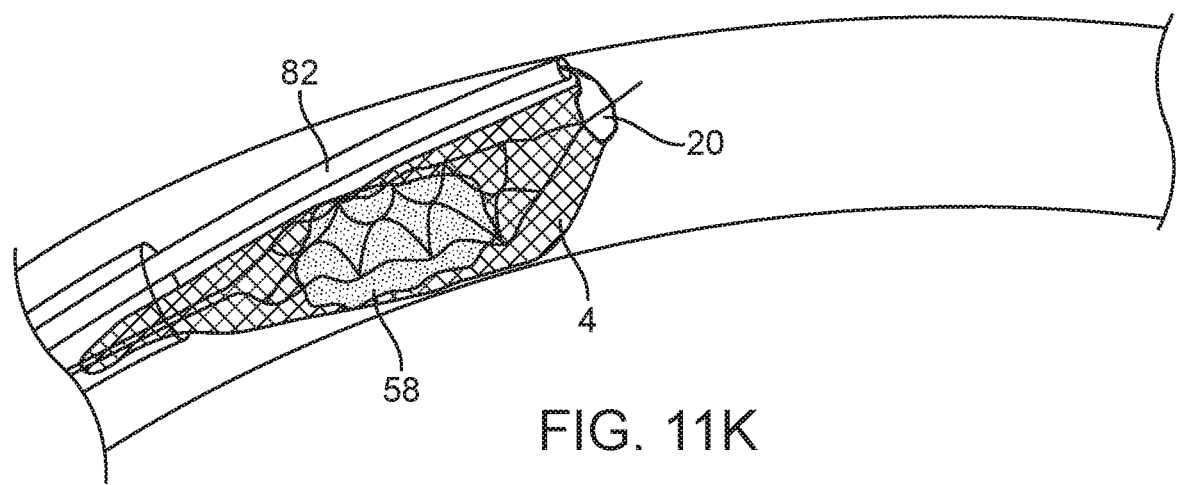
FIG. 11K illustrates the container element in a closed configuration.

In FIG. 11K, the filament perimeter 48 at the end of the device 2 is closed by pulling the arms 28, 30. The distal opening 20 of the container element 4 is therefore approximated and clot 78 is fully contained within the container element 4. At this point the device 2 with the clot 78 can be pulled from the vessel 80 and there may be a reduced likelihood of distal embolization since the clot is contained. The device 2 may then be withdrawn from the patient.

In FIGS. 12A and 12B, alternative embodiments of the device 2 are shown. The filaments 6 are on the outside of the container element 4 in these embodiments and additionally are routed within a filament catheter 82. The filament catheter 82 can hold the distal end 16 of the container element 4 in place as the tension is applied to the filaments 6 and the distal opening 20 is closed. Additionally, the filament catheter 82 can provide tension on the distal end 16 of the container element 4 such that the container element 4 can be stretched by pulling the proximal end of the container element 4 while holding the filament catheter 82 stationary or by pushing the distal end 16 of the container element 4 with the filament catheter 82 while holding the proximal end stationary or some combination therein. The filament catheter 82 may be comprised of any suitable catheter or tube material, such as nitinol, stainless steel, Pebax, PEEK, braided polyimide composite, or any other suitable construction. In some embodiments the filament catheter 82 can be a closed wound coil. In some embodiments there is a filament catheter 82 for each arm 28, 30. While the filament catheter 82 is shown on the outside of the container element 4 in FIGS. 12A and 12B, it can also be within the inner diameter of the container element 4.

FIGS. 10-11 and FIG. 12 show similar devices having features which are incorporated for each other. For example, both show the containing element 4 being free of attachments to the constraining catheter 8 and that the intermediate catheter 72 has the secondary lumen with the first filament 6 extending through the secondary lumen. Further still, both devices show the intermediate catheter 72 positioned in the lumen 24 of the constraining catheter 8 with the intermediate catheter 72 being movable relative to the constraining catheter 8 so that relative motion can move the containing element 4 to the released position (such as moving the intermediate catheter 72 distally relative to the constraining catheter 8). The devices 2 do differ in some respects in that the device 2 of FIGS. 10 and 11 is free of attachments to the intermediate catheter 72 while in FIG. 12 the containing element 4 is coupled to the intermediate catheter 72 for a length of at least 5 mm.

FIGS. 10-12 show embodiments where the filament 6 may include the features of any of the other embodiments described herein. For example, the filament 6 may having the leading portion which will still emerge from the constraining catheter 8 in the manner describe above even though the container element 4 is not attached to the constraining catheter 8. Of course, a feature such as the inverted portion is not implicitly included in the embodiment of FIG. 10A-10C while the features of the closed position would be implicitly included in the embodiments of FIGS. 10-12. It is also understood that in the interest of brevity that some claims are omitted when considering method claims similar to device claims and vice versa. Thus, either method or device claims so missing still form part of the present invention even when not specifically claimed.

Figure 13A:
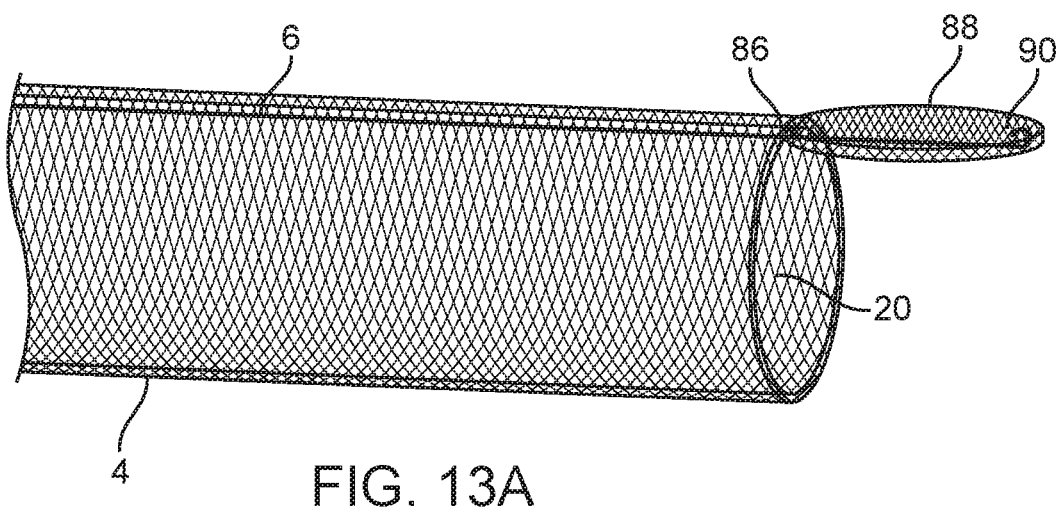
FIG. 13A illustrates an embodiment of the device with a flap in the open position.
Figure 13B:
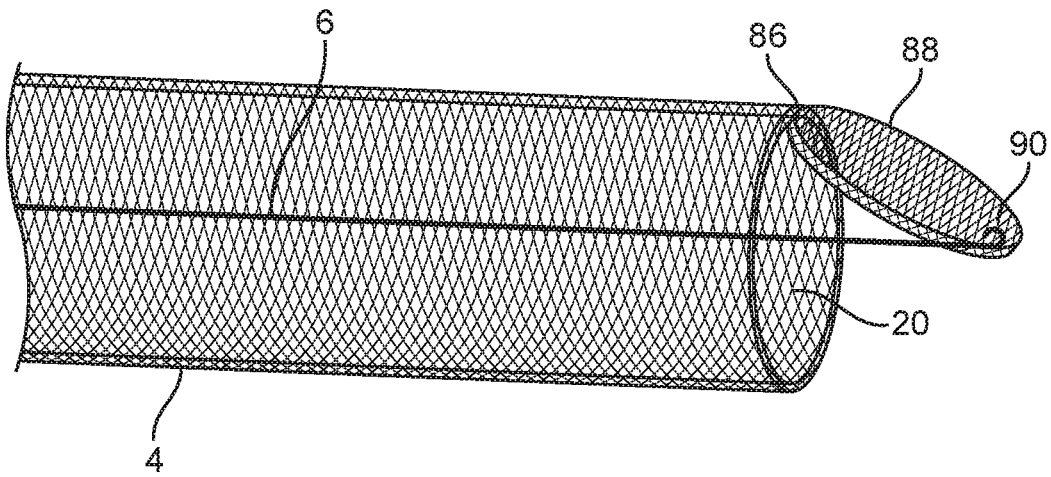
FIG. 13B illustrates an embodiment of the device with a flap in the partially closed position.
Figure 13C:
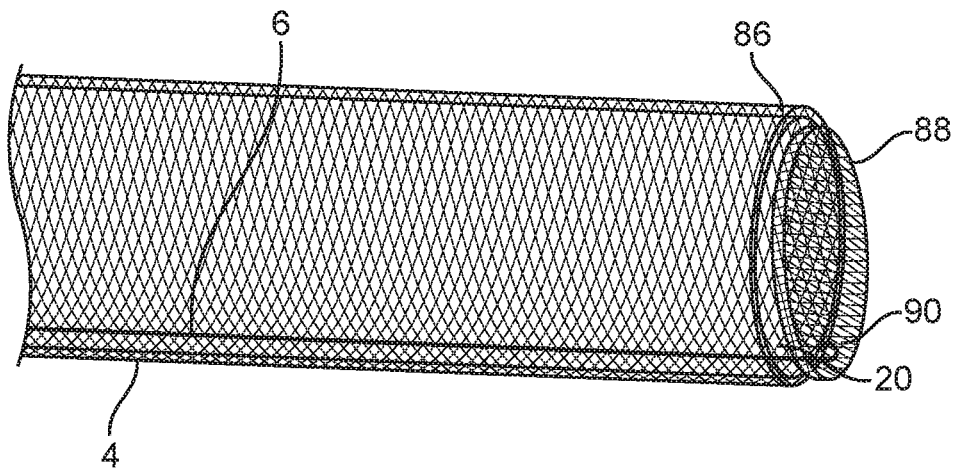
FIG. 13C illustrates an embodiment of the device with a flap in the closed position.
Figure 13D:
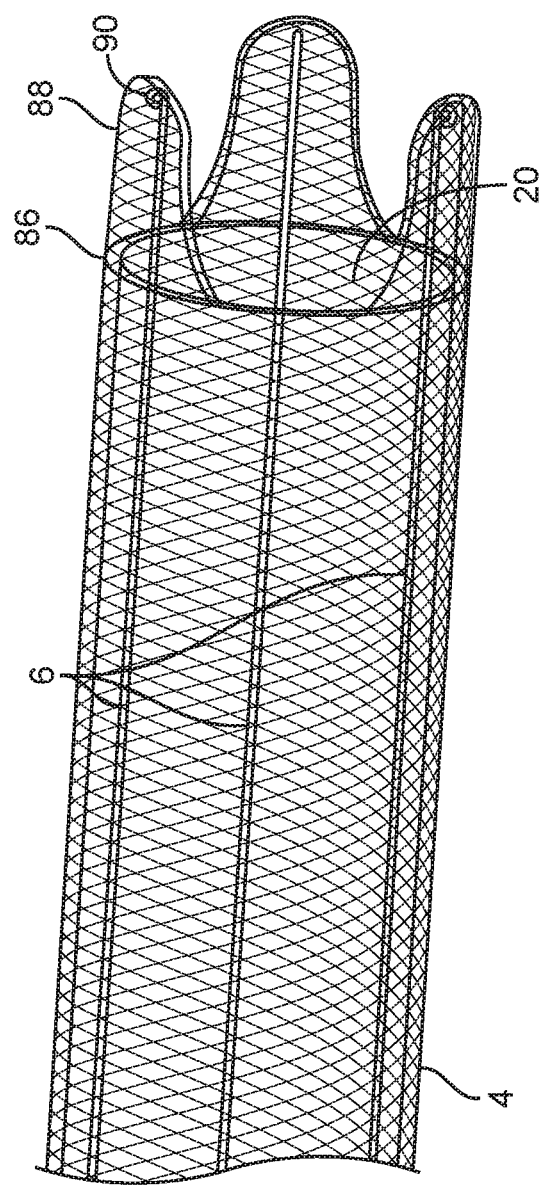
FIG. 13D illustrates an embodiment of the device with multiple flaps in the open position.

In FIG. 13A-13B, an embodiment of the device 2 and method are shown. In FIG. 13A, a container element 4 is shown with a distal opening 20. The container element 4 may be braided construction, stent construction, framed cage construction, or any other suitable structure. The container element 4 is generally tubular and has a distal end with a distal opening 20 as well as at least one flap 88. The flap 88 is a piece which extends distally past the distal opening 20 and has a flexing area 86. A filament 6 is attached to the flap 88 at the filament 6 connection. The filament 6 may be a wire such as a stainless steel, nitinol, plastic, or suture. The filament 6 may be connected to the flap 88 by a connection 90 as shown or by welding, heat bonding, mechanical swaging, or any other suitable process. In FIG. 13A, the flap 88 is in an unactuated state and there is minimal tension on the arm 28. Therefore, the distal opening 20 is generally open and may receive clots 78 or other material through the distal opening 20. When the user is ready to contain the materials in the container element 4, tension may be applied to the arm 28. The tension creates a force on the flap 88 that causes it to bend about the flexing area 86. In FIG. 13B, the flap 88 is rotated about 30 degrees and is thereby partially closing the distal opening 20. In FIG. 13C, additional tension is applied to the arm 28 and the distal opening 20 is primarily covered by the flap 88 that has been rotated and flexed into position. In some embodiments, the flap 88 may be comprised of the same material as the container element 4 (integrally formed). Alternatively, the flap 88 may be a separate component that is connected to the container element 4 at the flexing area 86. The connection may be a hinged connection (such as a living hinge) such that the flap 88 is primarily free to rotate about the flexing area 86. In some embodiments, a more rigid material may be applied to the flap 88 so that it does not crumple when the arm 28 is in tension. This may include adding fabric or plastic to the flap 88. In FIG. 13D, an alternative embodiment is shown with more than one flap 88. Three flaps 88 are shown each with their own filament 6 but any number of other flaps 88 may be contemplated such as between 1 to 10 flaps or 2 to 4 flaps. The filaments 6 may be tensioned at the same time or individually. Thus, any number of folding patterns may be contemplated. The flaps 88 may act like anatomical valve flaps which meet at the longitudinal axis LA of the container element 4. The flaps 88 do not need to be symmetric necessarily and can each be unique shapes. The shape of the flap 88 may be designed so that when all the flaps 88 are closed, the distal opening 20 of the container element 4 is mostly covered and materials within the container element 4 are trapped in place.

In any of the embodiments described herein aspiration may additionally be applied within the device 2 to further assist in capturing the clot 78. The aspiration may be connected to the intermediate catheter 72, constraining catheter 8, container element 4, or filament 6 catheter. In embodiments where aspiration is applied to the container element 4, the pieces of the clot 78 may be sucked into the container element 4. The aspiration reverses the blood flow so that it goes proximally. This may be useful especially in embodiments where the device 2 provides local flow arrest so that the suction only comes from the distal side of the clot 78 and ensures that even if the clot 78 breaks apart it will not distally embolize. The aspiration could be applied during certain steps in the procedure outlined above such as when the clot engagement element 58 is being deployed and then retracted into the container element 4. Alternatively, the use of aspiration may obviate the need for the clot engagement element 58. Aspiration may be used to suck the clot 78 into the container element 4 without using a separate retriever. In still other embodiments an agitator mechanism may be used to break up the clot and the aspiration then sucks the broken up pieces into the container element 4. The agitator may be mechanical such as a spinning or axially sliding element that contacts the clot and breaks it into smaller pieces that can be sucked up. Alternatively, the agitator may be vibratory or ultrasonic such that the clot breaks apart. Aspiration may be achieved with the use of a syringe or a vacuum source connected to the device 2. In some embodiments, the aspiration catheter 76 has a connected morcellating tip that is capable of breaking up clots 78. The aspiration catheter 76 can pull the clot 78 into the container element 4 and then the distal opening 20 can be closed. The morcellating tip can be used to emulsify or break down the clot into smaller pieces which can be sucked through the aspiration catheter 76. Once the clot 78 material is no longer within the container element 4, the distal opening 20 can be opened and the aspiration catheter 76 can be advanced to engage with still more clot 78. This process can be repeated any number of times. In some embodiments the same procedure is used for a stent retriever.

In still other embodiments, the container element 4 may not have an active closing element such as the filament 6 described herein but instead may be passively closed. The container element 4 may be shape set such that it is a long tube as shown in the figures but at the distal end 16 the container element 4 may funnel back to a constricted shape when it is deployed. A separate frame element may be used to actively hold the container element 4 open when it is ready to accept the clot engagement element 58 being retracted within the container element 4. Once it is within the container element 4, the frame can be moved axially to allow the container element 4 to constrict back to its shape set profile. This may allow the opening and closing of the distal end 16 of the container element 4 by sliding a frame element distally and proximally.

In some embodiments, the device 2 may contain all or only a portion of the devices described herein. For example, the device 2 may include a clot engagement element 58 such as a stent retriever or aspiration catheter. Alternatively, the device 2 may only include the container element 4 and filament 6 and the device 2 may be used with an existing off-the-shelf available stent retriever. In such an embodiment, the container element 4 and filament 6 may be sized to accept such a retriever. The device 2 may be inserted into the body after the stent retriever has been deployed and captured the clot. In this way it is a stand-alone system for capturing the clot that includes using other clot engagement elements. Any number of other configurations of the devices described herein are contemplated.

The device 2 can have a variety of shapes and sizes serving as a platform for any type of thrombectomy, embolectomy, or foreign body, calculi or tissue removal in any part of the body or vessel. The device 2 may provide proximal support for placement of distal devices such as rheolytic catheters, suction devices, graspers, balloons such as a Fogarty balloon, wire snares, stent retrievers, etc. for any size tube or vessel including arteries, veins, ureters, airways, bile ducts, and hollow viscous for retrieval of material.

The devices and methods described within may be used in any number of other surgical procedure. For example, peripheral blood clots may be likewise removed with such a system. Any number of other suitable applications may use such a device 2 for contained removal of a tissue, foreign body, calculi or other objects within a tubular contained space or even within non-tubular or non-contained spaces.

The names and labels applied to the various components and parts should not be considered limiting to the scope of the invented device and method. For example, the term filament used herein may be interchangeably used with snare, wire, ribbon, coil, elongate member, or any other suitable term. The term catheter is used to describe an elongate member with a distal and proximal end with a lumen extending there through. The terms intermediate catheter, constraining catheter, filament catheter, guide catheter, and micro catheter may often be used interchangeably. The term container element may often be interchangeably used with bag, containing element, container element, pouch, or any other suitable term. When referring to the opening of the distal opening, the terms releasing, deploying, opening, and expanding may be used interchangeably. When referring to the closure of the distal opening the terms cinching, closing, constraining, collapsing, constricting, snaring, or any other suitable term may often be used interchangeably. When referring to the radial constraining of the container element by catheters, vessels, or filaments, the terms constraining, restricting, containing, or constricting may also often be used interchangeably. The term filament perimeter may be used interchangeably with concave portion.

Although embodiments of various methods and devices are described herein in detail with reference to certain versions, it should be appreciated that other versions, embodiments, methods of use, and combinations thereof are also possible. Therefore, the spirit and scope of the appended claims should not be limited to the description of the embodiments contained herein.

The invention claimed is:

1. A device for removing occlusive material from a blood vessel, the device comprising:
a constraining catheter;
a containing element configurable into each of a collapsed configuration and an expanded configuration, said containing element at least partially encompassed by said constraining catheter when in said collapsed configuration, said containing element further comprising an expandable interior chamber for containing said occlusive material and an outer wall portion adapted to restrict antegrade flow in said blood vessel when in use, wherein a distal portion of said containing element in said collapsed configuration comprises a filament extending distal of said outer wall portion,
wherein, as said containing element expands towards said expanded configuration when released from said constraining catheter, said filament biases towards an unbiased shape that causes said filament to retract proximally into said distal portion and opens said distal portion; and
an actuator operatively coupled to said distal portion for reducing an area of a distal opening of said distal portion after capturing said occlusive material within said chamber.

2. The device of claim 1, wherein said distal portion of the containing element further comprises a braided structure, wherein said filament engages said braided structure, and further wherein tensioning a proximal portion of said filament causes said distal opening to reduce in area.

3. The device of claim 2, wherein said filament engages the braided structure by interweaving through at least a portion of the braided structure.

4. The device of claim 2, wherein said filament comprises a proximal filament portion within said expandable interior chamber and a distal filament portion coupled to said proximal filament portion, said distal filament portion engaging the braided structure with said containing element in said expanded configuration.

5. The device of claim 4, wherein said proximal filament portion is coupled to said distal filament portion with at least one arm.

6. The device of claim 1, wherein said actuator for reducing said area of said distal opening is configured to move said distal portion of said containing element proximally relative to the constraining catheter to reduce said area of said distal opening.

7. The device of claim 6, wherein said moving said distal portion of said containing element proximally further comprises inverting a portion of the containing element such that an outer wall of the distal portion of the containing element prior to said reducing said area transitions into an inner wall portion of the distal portion of the containing element.

8. The device of claim 7, wherein said inverting the portion of the containing element reduces said area of said distal opening to restrict escape of the occlusive material from the device.

9. The device of claim 1, wherein said reducing the area of said distal opening of the containing element comprises transitioning the distal portion of said containing element from a tubular shape comprising the distal opening to an inverted shape comprising a reduced area of the distal opening.

10. The device of claim 1, wherein, with said containing element in said collapsed configuration, said filament comprises one or more loops extending distally beyond said outer wall portion.

11. The device of claim 10, wherein a distal most portion of said containing element consists of a portion of said one or more loops.

12. The device of claim 10, wherein retraction of said one or more loops into said distal portion of said containing element assists the distal portion of the containing element to expand when the containing element is released from the constraining catheter.

13. The device of claim 1, wherein, with said containing element in said collapsed configuration, a distal most portion of said containing element consists of a portion of said filament.

14. The device of claim 1, wherein said filament comprises nitinol.

15. The device of claim 1, wherein the containing element further comprises a lumen adapted to receive at least one of an aspiration catheter and a stentriever.

16. The device of claim 1, wherein the outer wall portion of said containing element comprises an impermeable material to restrict said antegrade flow when said outer wall portion contacts a wall of said blood vessel during use.

17. The device of claim 1, wherein the outer wall portion of said containing element further comprises a braided structure, wherein said outer wall portion forms a tubular structure in said expanded configuration.

18. The device of claim 17, wherein said braided structure is capable of being longitudinally tensioned to increase a length of said braided structure and to decrease a diameter of said containing element.

19. The device of claim 1, wherein, when the containing element is in the constrained configuration, the filament comprises a first shape that is unique to the constrained configuration, and wherein the filament lacks the first shape both when the containing element is in the expanded configuration and when said area of said distal opening has been reduced.

20. The device of claim 19, wherein, when the containing element is in the expanded configuration, the filament comprises a second shape;
 wherein when the containing element comprises said reduced area of said distal opening, the filament comprises a third shape; and
 wherein said second shape is different from said third shape.

* * * * *